(12) United States Patent
Fitzsimons et al.

(10) Patent No.: US 8,071,563 B2
(45) Date of Patent: Dec. 6, 2011

(54) GLUTAMIC ACID DECARBOXYLASE (GAD) CHIMERA AND METHODS OF USE

(75) Inventors: Helen Fitzsimons, Bronx, NY (US); Ross Bland, Bronx, NY (US)

(73) Assignee: Neurologix, Inc., Fort Lee, NJ (US)

( * ) Notice: Subject to any disclaimer, the term of this patent is extended or adjusted under 35 U.S.C. 154(b) by 102 days.

(21) Appl. No.: 12/409,837

(22) Filed: Mar. 24, 2009

(65) Prior Publication Data

US 2009/0233994 A1 Sep. 17, 2009

Related U.S. Application Data

(63) Continuation of application No. 11/443,600, filed on May 31, 2006, now Pat. No. 7,527,785.

(60) Provisional application No. 60/685,764, filed on May 31, 2005.

(51) Int. Cl.
*A61K 48/00* (2006.01)
*A61K 38/43* (2006.01)
*A61K 38/00* (2006.01)
*C12P 21/06* (2006.01)
*C12N 9/88* (2006.01)
*C12N 15/00* (2006.01)
*C07H 21/04* (2006.01)

(52) U.S. Cl. ............... 514/44 R; 435/69.1; 435/232; 435/320.1; 424/94.1; 424/94.5; 436/23.1; 436/23.2; 436/23.4

(58) Field of Classification Search ............... 514/44 R; 435/69.1, 232, 320.1; 536/23.1, 23.2, 23.4; 424/94.1, 94.5

See application file for complete search history.

(56) References Cited

U.S. PATENT DOCUMENTS

| | | | |
|---|---|---|---|
| 4,579,770 | A | 4/1986 | Matsushita et al. |
| 4,596,792 | A | 6/1986 | Vyas |
| 4,599,230 | A | 7/1986 | Milich et al. |
| 4,599,231 | A | 7/1986 | Milich et al. |
| 4,601,903 | A | 7/1986 | Frasch |
| 4,608,251 | A | 8/1986 | Mia |
| 5,139,941 | A | 8/1992 | Muzyczka et al. |
| 5,968,757 | A | 10/1999 | Powers |
| 6,211,352 | B1 | 4/2001 | Harrison et al. |

OTHER PUBLICATIONS

Acsadi et al., "Human Dystrophin Expression in MDX Mice After Intramuscular Injection of DNA Constructs", Nature, vol. 352, pp. 815-818, 1991.
Aiello et al., "Adenovirus 5 DNA Sequences Present and RNA Sequences Transcribed In Transformed Human Embryo Kidney Cells (HEK-Ad-5 or 293)", Virology, vol. 94, pp. 460-469, 1979.
Andersson, "Genes and Obesity", Annals of Medicine, vol. 28, pp. 5-7, 1996.
Asada et al., "Cleft Palate and Decreased Brain γ-Aminobutyric Acid in Mice Lacking The 67-kDa Isoform of Glutamic Acid Decarboxylase", Proc. Natl. Acad. Sci, vol. 94, pp. 6496-6499, 1997.
Asada et al., "Mice Lacking The 65 kDa Isoform of Glutamic Acid Decarboxylase (GAD65) Maintain Normal Levels of GAD67 and GABA In Their Brains But Are Susceptible to Seizures", Biochemical and Biophysical Research Communications, vol. 229, pp. 891-895 (1996.
Baekkeskov et al., "Identification of the 64K Autoantigen in Insulin-Dependent Diabetes As the GABA-Synthesizing Enzyme Glutamic Acid Decarboxylase", Nature, vo. 347, pp. 151-166, 1990.
Bergman et al., "Reversal of Experimental Parkinsonism by Lesions of the Subthalamic Nucleus", Science, vol. 249, pp. 1436-1438, 1990.
Berkner, "Development of Adenovirus Vectors for the Expression of Heterologous Genes", BioTechniques, vol. 6, p. 616, 1988.
Bormann, "Electrophysiology of GABAA and GABABB Receptor Subtypes", TINS, vol. 11, pp. 112-116, 1988.
Boshart et al., "A Very Strong Enhancer Is Located Upstream of an Immediate Early Gene of Human Cytomegalovirus", Cell, vol. 41, pp. 521-530, 1985.
Boulis et al., "Stereotactic Gene Based Hypothalamic Neuromodulation", AANS Meeting, Abstract, 2002.
Braun et al., "Particle-Mediated DNA Immunization of Cattle Confers Long-Lasting Immunity Against Bovine Herpesvirus-1", Virology, vol. 265, pp. 46-56, 1999.
Bu et al., "Two Human Glutamate Decarboxylases, 65-kDa GAD and 67-kDa GAD, Are Each Encoded by a Single Gene", Proc. Natl. Acad. Sci., vol. 89, pp. 2115-2119, 1992.
Butterworth et al., "Phosphate-Activated Glutaminase in Relation to Huntington's Disease and Agonal State", Journal of Neurochemistry, vol. 41, pp. 440-447, 1983.
Byrne et al., "Multiplex Gene Regulation: A two-Tiered Approach to Transgene Regulation in Transgenic Mice", Proc. Natl. Acad. Sci., vol. 86, pp. 5473-5477, 1989.
Muramatsu et al., "In Vivo Electroporation: A Powerful and Convenient Means of Nonviral Gene Transfer to Tissues of Living Animals", International Journal of Molecular Medicine, vol. 1, pp. 55-62, 1998.
Capecchi, "High Efficiency Transformation by Direct Microinjection of DNA Into Cultured Mammalian Cells", Cell, vol. 22, pp. 479-488, 1980.

(Continued)

*Primary Examiner* — Ganapathirama Raghu
(74) *Attorney, Agent, or Firm* — Nutter McClennen & Fish LLP; George A. Xixis

(57) ABSTRACT

The invention relates to a novel Glutamic Acid Decarboxylase (GAD). More specifically, novel DNA and protein sequences relating to GAD. Additionally, the invention discloses a novel composition and related methods for treating neurodegenerative diseases such as Parkinson's disease, Alzheimer's disease, epilepsy, and the like, using viral and non-viral delivery systems that deliver therapeutic agents to specific regions of the brain. More specifically, using an adeno-associated viral vector to deliver a nucleotide sequence encoding a novel glutamic acid decarboxylase (GAD) to specific regions of the brain that are over stimulated or disinhibited in various diseases, including neurodegenerative diseases.

23 Claims, 12 Drawing Sheets

OTHER PUBLICATIONS

Carter, "Adeno-Associated Virus Vectors", Current Opinion in Biotechnology, vol. 3, pp. 533-539, 1992.

Chu et al., "SV40 DNA Transfection of Cells in Suspension: Analysis of the Efficiency of Transcription and Translation of T-Antigen", Gene, vol. 13, pp. 197-202, 1981.

Clark et al., "Highly Purified Recombinant Adeno-Associated Virus Vectors Are Biologically Active and Free of Detectable Helper and Wild-Type Viruses", Human Gene Therapy, vol. 10, pp. 1031-1039, 1999.

Collins et al., "Pharmacologic Manipulation of Ob Expression in a Dietary Model of Obesity", The Journal of Biological Chemistry, vol. 271, pp. 9437-9440, 1996.

Darling, "Mice As Models of Human Development Disorders: Natural and Artificial Mutants", Current Opinion in Genetics & Development, vol. 6, pp. 289-294, 1996.

Degano et al., "Gene Gun Intradermal DNA Immunization Followed by Boosting With Modified Vaccinia Virus Ankara: Enhanced CD8 + T Cell Immunogenicity and Protective Efficacy In the Influenza and Malaria Models", Vaccine, vol. 18, pp. 623-632, 2000.

Depaulis et al., "Endogenous Control of Epilepsy: The Nigral Inhibitory System", Progress in Neurology, vol. 42, pp. 33-52, 1994.

Dirkx et al., "Targeting of the 67-kDA Isoform of Glutamic Acid Decarboxylase to Intracellular Organelles Is Mediated by Its Interaction With the NH2-Terminal Region of the 65-kDa Isoform of Glutamic Acid Decarboxylase", The Journal of Biological Chemistry, vol. 270, pp. 2241-2246,1995.

Drew et al., "Vaccination With Plasmid DNA Expression Antigen From Genomic or cDNA Gene Forms Induces Eqivalent Humoral Immune Responses", Vaccine, vol. 18, pp. 692-702, 2000.

During et al., "Peroral Gene Therapy of Lactose Intolerance Using an Adeno-Associated Virus Vector", Nature Medicine, vol. 4, pp. 1131-1135, 1998.

Erlander et al., "Two Genes Encode Distinct Glutamate Decarboxylases", Neuron, vol. 7, pp. 91-100, 1991.

Esclapez et al., "Coparative Localization of Two Forms of Glutamic Acid Decarboxylase and Their mRNAs in Rat Brain Support the Concept of Functional Differences Between the Forms", The Journal of Neuroscience, vol. 14, pp. 1834-1835, 1994.

Felgner et al., "Lipofection: A Highly Efficient, Lipid-Mediated DNA-Transfection Procedure", Proc. Natl. Acad. SCI USA, vol. 84, pp. 7413-7417, 1987.

Forss-Petter et al., "Neuron-Specific Enolase: Complete Structure of Rat mRNA, Multiple Transcriptional Start Sites, and Evidence Suggesting Post-Transcriptional Control", Journal of Neuroscience Research, vol. 16, pp. 141-156, 1986.

Galfre et al., "Preparation of Monoclonal Antibodies: Strategies and Procedures", Methods in Enzymology, vol. 73, pp. 1-46, 1981.

Graham et al., "Characteristics of a Human Cell Line Transformed by DNA From human Adenovirus Type 5", J. Gen. Virol., vol. 36, pp. 59-74, 1977.

Graham et al., "A New Technique for the Assay of Infectivity of Human Adenovirus 5 DNA", Virology, vol. 52, pp. 456-467, 1973.

Grimm et al., "Progress in Adeno-Associated Virus Type 2 Vector Productin: Promises and Prospects for Clinical Use", Human Gene Therapy, vol. 10, pp. 2445-2450, 1999.

Jasmin et al., "Analgesia and Hyperalgesia From GABA-Mediated modulation of the Cerebral Cortex", Nature, vol. 424, pp. 316-320, 2003.

Johnston et al., The Use of Microparticle Injection to Introduce Genes Into Animal Cells In Vitro and In Vivo, Genetic Engineering, vol. 15, pp. 225-236, 1993.

Kanaani et al., "A Combination of Three Distinct Trafficking Signals Mediates Axonal Targeting and Presynaptic Clustering of GAD65", The Journal of Cell Biology, vol. 158, pp. 1229-1238, 2002.

Kanaani et al., "The Hydrophilie Isoform of Glutamate Decarboxylase, GAD67, Is Targeted to membranes and Nerve Terminals Independent of Dimerization With the Hydrophobic Membrane-Anchored Isoform, GAD65", The Journal of Biological Chemistry, vol. 274, pp. 37200-37209, 1999.

Kapadia et al., "Simultaneous Lumbar and Intraventricular Manometry to Evaluate the Role and Safety of Lumbar Puncture in Raised Intracranial Pressure Following Subarachnoid Haemorrhage", British Journal of Neurosurgery, vol. 10, pp. 585-587, 1996.

Karlsson et al., "Effect of the Convulsive Agent 3-Mercaptopropionic Acid on the Levels Decarboxylase in Different Regions of the Rat Brain", Biochemical Pharmacology, vol. 21, pp. 3053-3061, 1974.

Kash et al., "Epilepsy in Mice Deficient in the 65-kDa Isoform of Glutamic Acid Decarboxylase", Proc. Natl. Acad. Sci USA, vol. 94, pp. 14060-14065, 1997.

Klein et al., "High-Velocity Microprojectiles for Delivering Nucleic Acids Into Living Cells", Nature, vol. 327, pp. 70-73, 1987.

Kotin, "Prospects for The Use of Adeno-Associated Virus As a Vector for Human Gene Therapy", Human Gene Therapy, vol. 5, pp. 793-801, 1994.

Ladner et al., "Human CSF-1: Gene Structure and Alternative Splicing of mRNA Precursors", The EMBO Journal, vol. 6, pp. 2693-2698, 1987.

Lai et al., "DNA Vaccines", Critical Reviews in Immunology, vol. 18, pp. 449-484, 1998.

Lebkowski et al., "Adeno-Associated Virus: A Vector System for Efficient Introduction and Integration of DNA Into a Variety of Mammalian Cell Types", Molecular and Cellular Biology, vol. 8, pp. 3988-3996, 1988.

Leventhal et al., "GABA and Its Agonists Improved Visual Cortical Function in Senescent Monkeys", Science, vol. 300, p. 812, 2003.

Luo et al., "Subthalmic GAD Gene Therapy in a Parkinson's Disease Rat Model", Science, vol. 298, p. 425, 2002.

Mannino et al., "Liposome Mediated Gene Transfer", BioTechniques, vol. 6, pp. 682-690, 1988.

McCarty et al., "Sequences Required for Coordinate Induction of Adeno-Associated Virus p19 and p40 Promoters by Rep Protein", Journal of Virology, vol. 65, pp. 2936-2945, 1991.

McKnight et al., "The Distal Transcription Signals of the Herpesvirus tk Gene Share a Common Hexanucleotide Control Sequence", Cell, vol. 37, pp. 253-262,1984.

Morii et al., "Structure and Chromosome Assignment of Human S100 ? and ss Subunit Genes", Biochemical and Biophysical Research Communications, vol. 175, pp. 185-191, 1991.

Muramatsu et al., "In Vivo Electroporation: A Powerful and Convenient Means of NonViral Gene Transfer to Tissues of Living Animals (Review)", International Journal O Molecular Medicine, vol. 1, pp. 55-62, 1998.

Muzyczka, "Use of Adeno-Associated Virus As a General Transduction Vector for Mammalian Cells", Current Topics in Microbiology and Immunology, vol. 158, pp. 97-129, 1992.

Namchuk et al., "Phosphorylation of Serine Residues 3, 6, 10, and 13 Distinguishes Membrane Anchored From Soluble Glutamic Acid Decarboxylase 65 and Is Restricted to Glutamic Acid Decarboxylase 65a", The Journal of Biological Chemistry, vol. 272, pp. 1548-1557, 1997.

Ng et al., "Evolution of the Functional Human ss-Actin Gene and Its Multi-Pseudogene Family: Conservation of Noncoding Regions and Chromosomal Dispersion of Pseudogenes", Molecular and Cellular Biology, vol. 5, pp. 2720-2732, 1985.

Oliva et al., "Complete Structure of the Human Gene Encoding Neuron-Specific Enolase", Genomics, vol. 10, pp. 157-165, 1991.

Robinson, "DNA Vaccines: Basic Mechanism and Immune Responses", International Journal of Molecular Medicine, vol. 4, pp. 549-555, 1999.

Rogaev et al., "An Informative Microsatellite Repeat Polymorphism in the Human Neurofilament Light Polypeptide (NEFL) Gene", Human Molecular Genetics, vol. 1, p. 781, 1992.

Rosenfeld et al., "Adenovirus-Mediated Transfer of a Recombinant ?1-Antitrypsin Gene to the Lung", Science, vol. 252, pp. 431-434, 1991.

Rosenfeld et al., "In Vivo Transfer of the Human Cystic Fibrosis Transmembrane Conductance Regulator Gene to the Airway Epithelium", Cell, vol. 68, pp. 143-155, 1992.

Samulski et al., "Helper-Free Stocks of Recombinant Adeno-Associated Viruses: Normal Integration Does Not Require Viral Gene Expression", Journal of Virology, vol. 63, pp. 3822-3828, 1989.

Schwartz et al., "Matrices for Detecting Distant Relationships", Atlas of Protein Sequence and Structure, pp. 353-358, 1978.

Sheikh et al., "Heteromers of Glutamate Decarboxylase Isoforms Occur in Rat Cerebellum", Journal of Neurochemistry, vol. 66, pp. 2082-2090, 1996.

Shelling et al., "Targeted Integration of Transfected and Infected Adeno-Associated Virus Vectors Containing the Neomycin Resistance Gene", Gene Therapy, vol. 1, pp. 165-169, 1994.

Shigekawa et al., "Electroporation of Eukaryotes and Prokaryotes: a General Approach to the Introduction of Macromolecules Into Cells", BioTechniques, vol. 6, pp. 742-751, 1988.

Smith et al., "Comparison of Biosequences", Advances in Applied Mathematics, vol. 2, pp. 482-489, 1981.

Stork et al., "Postnatal Development of a GABA Deficit and Disturbance of Neural Functions in Mice Lacking GAD65", Brain Research, vol. 865, pp. 45-58, 2000.

Urlaub et al., "Isolation of Chinese Hamster Cell Mutants Deficient in Dihydrofolate Reductase Activity", Proc. Natl. Acad. Sci. USA, vol. 77, pp. 4216-4220, 1980.

Wistuba et al., "Subcellular Compartmentalization of Adeno-Associated Virus Type 2 Assembly", Journal of Virology, vol. 71, pp. 1341-1352, 1997.

Wolff et al., "Direct Gene Transfer Into Mouse Muscle In Vivo", Science, vol. 247, pp. 1465-1468, 1990.

Wong et al., "Insulin-Dependent Diabetes Mellitus and Its Animal Models", Current Opinion in Immunology, vol. 11, pp. 643-647, 1999.

Xu et al., "CMV-ss-Actin Promoter Directs Higher Expression From an Adeno-Associated Viral Vector in the Liver Than the Cytomegalovirus or Elongaton Factor 1? Promoter and Results in Therapeutic Levels of Human Factor X in Mice", Human Gene Therapy, vol. 12, pp. 563-573, 2001.

Zhou et al., "Adeno-Associated Virus 2-Mediated High Efficiency Gene Transfer Into Immature and Mature Subsets of Hematopoietic Progenitor Cells in Human Umbilical Cord Blood", J. Exp. Med., vol. 179, pp. 1867-1875, 1994.

Zolotukhin et al., "Recombinant Adeno-Associated Virus Purification Using Novel Methods Improves Infectious Titer and Yield", Gene Therapy, vol. 6, pp. 973-985, 1999.

Powers et al., "Comparative Analysis of Epitope Recognition of Glutamic Acid Decarboxylase (GAD) by Autoantibodies From Different Autoimmune Disorders", Clin Exp Immunil,, vol. 118, pp. 349-356, 1999.

Bonifacio et al., "Maturation of the Humoral Autoimmune Response to Epitopes of GAD in Preclinical Childhood Type 1 Diabetes", Diabetes, vol. 49, pp. 202-208, 2000.

Kobayashi et al., "Unique Epitopes of Glutamic Acid Decarboxylase Autoantibodies in Slowly Progressive Type 1 Diabetes", The Journal of Clinical Endocrinology, vol. 88, pp. 4768-4775, 2003.

European Office Action No. 06 771 671.2-2401 dated Jul. 29, 2010.

```
                              501                                              550
human GAD67            (498) GCAGATCCTGGTTGACTGCAGAGACACCTTGAAGTATGGGGTTCGCACAG
human GAD65            (471) GGAAAATTTGATGCATTGCACTGCAGAGACACAACTCTAAAATATGCAATAAAACAG
human GAD65(1-60)GAD67(66-594) (489) GCAGATCCTGGTTGACTGCAGAGACACCTTGAAGTATGGGGTTCGCACAG
human GAD65(1-72)GAD67(79-594) (486) GCAGATCCTGGTTGACTGCAGAGACACCTTGAAGTATGGGGTTCGCACAG
              Consensus (501) GCAGATCCTGGTTGACTGCAGAGACACCTTGAAGTATGGGGTTCGCACAG
                              551                                              600
human GAD67            (548) GTCATCCTCGATTTTTCAACCAGCTCTCCACTGGATTGGATATTATTGGC
human GAD65            (521) GGCATCCTAGATACTTCAATCAACTTTCTACTGCTTTGCATATGGTTGGA
human GAD65(1-60)GAD67(66-594) (539) GTCATCCTCGATTTTTCAACCAGCTCTCCACTGGATTGGATATTATTGGC
human GAD65(1-72)GAD67(79-594) (536) GTCATCCTCGATTTTTCAACCAGCTCTCCACTGGATTGGATATTATTGGC
              Consensus (551) GTCATCCTCGATTTTTCAACCAGCTCTCCACTGGATTGGATATTATTGGC
                              601                                              650
human GAD67            (598) CTAGCTGGAGAATGGCTGACTGGCTGACATCAAACGGCCAATACCAACATGTTTACATA
human GAD65            (571) TTAGCAGCAGACTGGCTGACATCGCTGACATCAACAGCAAATACTCACCTA
human GAD65(1-60)GAD67(66-594) (589) CTAGCTGGAGAATGGCTGACTGGCTGACATCAACGGCCAATACCAACATGTTTACATA
human GAD65(1-72)GAD67(79-594) (586) CTAGCTGGAGAATGGCTGACTGGCTGACATCAACGGCCAATACCAACATGTTTACATA
              Consensus (601) CTAGCTGGAGAATGGCTGACTGGCTGACATCAACGGCCAATACCAACATGTTTACATA
                              651                                              700
human GAD67            (648) TGAAAATTGCACCAGTGTTTGTCCTCATGGAACAAATAACACTTAAGAAGA
human GAD65            (621) TGAAAATTGCTCCAGTATTTGTGCTTTTGGAATATGTCACACTAAAGAAAA
human GAD65(1-60)GAD67(66-594) (639) TGAAAATTGCACCAGTGTTTGTCCTCATGGAACAAATAACACTTAAGAAGA
human GAD65(1-72)GAD67(79-594) (636) TGAAAATTGCACCAGTGTTTGTCCTCATGGAACAAATAACACTTAAGAAGA
              Consensus (651) TGAAAATTGCACCAGTGTTTGTCCTCATGGAACAAATAACACTTAAGAAGA
                              701                                              750
human GAD67            (698) TGAGAGAGATAGTTGGATGGTCAAGTAAAGATGGTGATGGGATATTTCT
human GAD65            (671) TGAGAGAGAAATCATTGGCTGGCCAGGGGCTCTGGCGATGGGATATTTCT
human GAD65(1-60)GAD67(66-594) (689) TGAGAGAGATAGTTGGATGGTCAAGTAAAGATGGTGATGGGATATTTCT
human GAD65(1-72)GAD67(79-594) (686) TGAGAGAGATAGTTGGATGGTCAAGTAAAGATGGTGATGGGATATTTCT
              Consensus (701) TGAGAGAGATAGTTGGATGGTCAAGTAAAGATGGTGATGGGATATTTCT
```

Figure 1C

```
                                        751                                                          800
human GAD67           (748) CCTGGGGGGCGCCATATCCAACATGTACAGCATCATGGCTGCTCGCTACAA
human GAD65           (721) CCGGTGGGGGCGCCATATCTAACATGTATGCCATGATGATCGACGCTTTAA
human GAD65(1-60)GAD67(66-594) (739) CCTGGGGGGCGCCATATCCAACATGTACAGCATCATGGCTGCTCGCTACAA
human GAD65(1-72)GAD67(79-594) (736) CCTGGGGGGCGCCATATCCAACATGTACAGCATCATGGCTGCTCGCTACAA
            Consensus (751) CCTGGGGGCGCCATATCCAACATGTACAGCATCATGGCTGCTCGCTACAA
                                        801                                                          850
human GAD67           (798) GTACTTCCCGGAAGTTAAGACAAAGGGCATGGCGGCTGTGCCTAAACTGG
human GAD65           (771) GATGTTCCCAGAGTCAAGGAGACAAAGGAAATGGCTGCTCTTCCCAGGCTCA
human GAD65(1-60)GAD67(66-594) (789) GTACTTCCCGGAAGTTAAGACAAAGGGCATGGCGGCTGTGCCTAAACTGG
human GAD65(1-72)GAD67(79-594) (786) GTACTTCCCGGAAGTTAAGACAAAGGGCATGGCGGCTGTGCCTAAACTGG
            Consensus (801) GTACTTCCCGGAAGTTAAGACAAAGGGCATGGCGGCTGTGCCTAAACTGG
                                        851                                                          900
human GAD67           (848) TCCTCTTCACCTCAGAACCAGAGTCACTATTCCATAAAGAAAGCTGGGCT
human GAD65           (821) TTGCCTTCACCTCACGTCTGAACATAGTCACTCATTTTTCTCTCAAGAAGGAGCTGCA
human GAD65(1-60)GAD67(66-594) (839) TCCTCTTCACCTCAGAACCAGAGTCACTATTCCATAAAGAAAGCTGGGCT
human GAD65(1-72)GAD67(79-594) (836) TCCTCTTCACCTCAGAACCAGAGTCACTATTCCATAAAGAAAGCTGGGCT
            Consensus (851) TCCTCTTCACCTCAGAACCAGAGTCACTATTCCATAAAGAAAGCTGGGCT
                                        901                                                          950
human GAD67           (898) GCACTTGGCTTTGGAACTGACAATGTGATTTTGATAAAGTGCAATGAAAG
human GAD65           (871) GCCTTAGGGATTGGAACAGACAGACAATGTCTTGATTCTGATTAAATGATGAGAG
human GAD65(1-60)GAD67(66-594) (889) GCACTTGGCTTTGGAACTGACAATGTGATTTTGATAAAGTGCAATGAAAG
human GAD65(1-72)GAD67(79-594) (886) GCACTTGGCTTTGGAACTGACAATGTGATTTTGATAAAGTGCAATGAAAG
            Consensus (901) GCACTTGGCTTTGGAACTGACAATGTGATTTTGATAAAGTGCAATGAAAG
                                        951                                                         1000
human GAD67           (948) GGGGAAATAATTCCAGCTGATTTTGAGGCAAAATTCTTGAAGCCAAAC
human GAD65           (921) AGGGAAAATGATTCCATTGATCTTGAAAGAAGGATTCTTGAAGCCAAAC
human GAD65(1-60)GAD67(66-594) (939) GGGGAAATAATTCCAGCTGATTTTGAGGCAAAATTCTTGAAGCCAAAC
human GAD65(1-72)GAD67(79-594) (936) GGGGAAATAATTCCAGCTGATTTTGAGGCAAAATTCTTGAAGCCAAAC
            Consensus (951) GGGGAAATAATTCCAGCTGATTTTGAGGCAAAAATTCTTGAAGCCAAAC
```

Figure 1D

```
                                          1050
human GAD67              (998)  AGAAGGGATATGTTCCCTTTTATGTCAATGCAACTGCTGGCACGACTGTT
human GAD65              (971)  AGAAAGGGTTTGTTCCTTTCCCTTTTATGTCAATGCAACTGCTGGCACGACTGTG
human GAD65(1-60)GAD67(66-594) (989)  AGAAGGGATATGTTCCCTTTTATGTCAATGCAACTGCTGGCACGACTGTT
human GAD65(1-72)GAD67(79-594) (986)  AGAAGGGATATGTTCCCTTTTATGTCAATGCAACTGCTGGCACGACTGTT
                Consensus      (1001) AGAAGGGATATGTTCCCTTTTATGTCAATGCAACTGCTGGCACGACTGTT
                                          1100
human GAD67              (1048) TATGGAGCTTTGATCCGATACAAGAGATTGCAGATATATGTGAGAAATA
human GAD65              (1021) TACGGAGCATTTGACCCCCTCTTAGCTGTCGCTGACATTTGCAAAAGTA
human GAD65(1-60)GAD67(66-594) (1039) TATGGAGCTTTTGATCCGATACAAGAGATTGCAGATATATGTGAGAAATA
human GAD65(1-72)GAD67(79-594) (1036) TATGGAGCTTTTGATCCGATACAAGAGATTGCAGATATATGTGAGAAATA
                Consensus      (1051) TATGGAGCTTTGATCCGATACAAGAGATTGCAGATATATGTGAGAAATA
                                          1150
human GAD67              (1098) TAACCTTTGGTTGCATGTCGATGCTGCCTGGGAGGTGGGCTGCTCATGT
human GAD65              (1071) TAAGATCGATGCATGTGGATCGCAGCTGCCTGGGGGTGGGGATTACTGATGT
human GAD65(1-60)GAD67(66-594) (1089) TAACCTTTGGTTGCATGTCGATGCTGCCTGGGAGGTGGGCTGCTCATGT
human GAD65(1-72)GAD67(79-594) (1086) TAACCTTTGGTTGCATGTCGATGCTGCCTGGGAGGTGGGCTGCTCATGT
                Consensus      (1101) TAACCTTTGGTTGCATGTCGATGCTGCCTGGGAGGTGGGCTGCTCATGT
                                          1200
human GAD67              (1148) CCAGGAAGCACCGCCATAAACTCAACGGCATAGAAAGGCCAACTCAGTC
human GAD65              (1121) CCCGAAAACACAAGTGGCACCGCCATAAACTGAAACTGAAACTCAACGGCGTGGGAGGGCCAACTCTGTG
human GAD65(1-60)GAD67(66-594) (1139) CCAGGAAGCACCGCCATAAACTCAACGGCATAGAAAGGCCAACTCAGTC
human GAD65(1-72)GAD67(79-594) (1136) CCAGGAAGCACCGCCATAAACTCAACGGCATAGAAAGGCCAACTCAGTC
                Consensus      (1151) CCAGGAAGCACCGCCATAAACTCAACGGCATAGAAAGGCCAACTCAGTC
                                          1250
human GAD67              (1198) ACCTGGAACCCTCACAAGATGATGGGCGTGCTGTTGCAGTGCTCTGCCAT
human GAD65              (1171) ACGTGGAATCCACACAAGATGATGGAGTCCCTTTGCTGTTGCAGTGCTCTGCTCT
human GAD65(1-60)GAD67(66-594) (1189) ACCTGGAACCCTCACAAGATGATGGGCGTGCTGTTGCAGTGCTCTGCCAT
human GAD65(1-72)GAD67(79-594) (1186) ACCTGGAACCCTCACAAGATGATGGGCGTGCTGTTGCAGTGCTCTGCCAT
                Consensus      (1201) ACCTGGAACCCTCACAAGATGATGGGCGTGCTGTTGCAGTGCTCTGCCAT
```

```
human GAD67    (1748) TCATTGAGGAGATAGAAAGACTGGGCCAGGATCTGTAA
human GAD65    (1721) TGATTGAAGAAATAGAACGCCTTGGACAAGATTTATAA
human GAD67(66-594)   (1739) TCATTGAGGAGATAGAAAGACTGGGCCAGGATCTGTAA
human GAD67(79-594)   (1736) TCATTGAGGAGATAGAAAGACTGGGCCAGGATCTGTAA
human GAD65(1-60)GAD67(66-594) (1739) TCATTGAGGAGATAGAAAGACTGGGCCAGGATCTGTAA
human GAD65(1-72)GAD67(79-594) (1736) TCATTGAGGAGATAGAAAGACTGGGCCAGGATCTGTAA
Consensus      (1751) TCATTGAGGAGATAGAAAGACTGGGCCAGGATCTGTAA
```

Figure 1H

```
                      301                                                                350
human GAD65           LGIGTDSVILIKCDERGKMIPSDLERRILEAKQKGFVPFLVSATAGTTVY
human GAD67           LGFGTDNVILIKCNERGKIIPADFEAKILEAKQKGYVPFYVNATAGTTVY
hGAD65(1-60)hGAD67(66-594)  LGFGTDNVILIKCNERGKIIPADFEAKILEAKQKGYVPFYVNATAGTTVY
hGAD65(1-72)hGAD67(79-594)  LGFGTDNVILIKCNERGKIIPADFEAKILEAKQKGYVPFYVNATAGTTVY
Consensus             LGFGTDNVILIKCNERGKIIPADFEAKILEAKQKGYVPFYVNATAGTTVY 351                                                                400
human GAD65           GAFDPLLAVADICKKYKIWMHVDAAWGGGLLMSRKHKWKLSGVERANSVT
human GAD67           GAFDPIQEIADICEKYNLWLHVDAAWGGGLLMSRKHRHKLNGIERANSVT
hGAD65(1-60)hGAD67(66-594)  GAFDPIQEIADICEKYNLWLHVDAAWGGGLLMSRKHRHKLNGIERANSVT
hGAD65(1-72)hGAD67(79-594)  GAFDPIQEIADICEKYNLWLHVDAAWGGGLLMSRKHRHKLNGIERANSVT
Consensus             GAFDPIQEIADICEKYNLWLHVDAAWGGGLLMSRKHRHKLNGIERANSVT 401                                                                450
human GAD65           WNPHKMMGVPLQCSAILVREEGLMQNCNQMHASYLFQQDKHYDISYDTGD
human GAD67           WNPHKMMGVLLQCSAILVKEKGILQGCNQMCAGYLFQPDKQYDVSYDTGD
hGAD65(1-60)hGAD67(66-594)  WNPHKMMGVLLQCSAILVKEKGILQGCNQMCAGYLFQPDKQYDVSYDTGD
hGAD65(1-72)hGAD67(79-594)  WNPHKMMGVLLQCSAILVKEKGILQGCNQMCAGYLFQPDKQYDVSYDTGD
Consensus             WNPHKMMGVLLQCSAILVKEKGILQGCNQMCAGYLFQPDKQYDVSYDTGD 451                                                                500
human GAD65           KAIQCGRHVDVFKLWLMWRAKGTGFEAHVDKCLELAEYLYNIIKNREGY
human GAD67           KAIQCGRHVDIFKFWLMWKAKGTVGFEANQINKCLELAEYLYAKIKNREEF
hGAD65(1-60)hGAD67(66-594)  KAIQCGRHVDIFKFWLMWKAKGTVGFEANQINKCLELAEYLYAKIKNREEF
hGAD65(1-72)hGAD67(79-594)  KAIQCGRHVDIFKFWLMWKAKGTVGFEANQINKCLELAEYLYAKIKNREEF
Consensus             KAIQCGRHVDIFKFWLMWKAKGTVGFEANQINKCLELAEYLYAKIKNREEF 501                                                                550
human GAD65           EMVFDGKPQHTNVCFWYIPPSLRTLEDNEERMSRLSKVAPVIKARMMEYG
human GAD67           EMVFNGEPEHTNVCFWYIPQSLRGVPDSPQRREKLHKVAPKIKALMMESG
hGAD65(1-60)hGAD67(66-594)  EMVFNGEPEHTNVCFWYIPQSLRGVPDSPQRREKLHKVAPKIKALMMESG
hGAD65(1-72)hGAD67(79-594)  EMVFNGEPEHTNVCFWYIPQSLRGVPDSPQRREKLHKVAPKIKALMMESG
Consensus             EMVFNGEPEHTNVCFWYIPQSLRGVPDSPQRREKLHKVAPKIKALMMESG 551                                    594
human GAD65           TTMVSYQPLGDKVNFFRMVISNPAATHQDIDFLIEEIERLGQDL
human GAD67           TTMVGYQPQGDKANFFRMVISNPAATQSDIDFLIEEIERLGQDL
hGAD65(1-60)hGAD67(66-594)  TTMVGYQPQGDKANFFRMVISNPAATQSDIDFLIEEIERLGQDL
hGAD65(1-72)hGAD67(79-594)  TTMVGYQPQGDKANFFRMVISNPAATQSDIDFLIEEIERLGQDL
Consensus             TTMVGYQPQGDKANFFRMVISNPAATQSDIDFLIEEIERLGQDL
```

FIGURE 2B

GLUTAMIC ACID DECARBOXYLASE (GAD) CHIMERA AND METHODS OF USE

CROSS REFERENCE TO RELATED APPLICATION

The present application claims priority to U.S. Provisional Application Ser. No. 60/685,764 filed May 31, 2005, U.S. application Ser. No. 11/443,600 (issued as U.S. Pat. No. 7,527,785 on May 5, 2009) filed May 31, 2006, both entitled "Novel Glutamic Acid Decarboxylase (GAD) Chimera and Methods of Use", and both of which are herein incorporated by reference.

FIELD OF THE INVENTION

The invention relates to novel Glutamic Acid Decarboxylases (GAD). More specifically, the invention relates to novel DNA and protein sequences relating to GAD. Additionally, the invention contemplates a novel composition and related methods for treating neurodegenerative diseases such as Parkinson's disease, Alzheimer's disease, epilepsy, and the like, using viral and non-viral delivery systems that deliver therapeutic agents to specific regions of the brain. More specifically, the invention contemplates using an adeno-associated viral vector to deliver a nucleotide sequence encoding a novel glutamic acid decarboxylase (GAD) to specific regions of the brain that are over stimulated or disinhibited in various diseases, including neurodegenerative diseases.

BACKGROUND OF THE INVENTION

I. Glutamic Acid Decarboxylase (GAD) and Gamma-aminobutyric Acid (GABA)

The major inhibitory neurotransmitter in the brain is gamma-aminobutyric acid (GABA), (Roberts et al, GABA in Nervous System Function, Raven Press: New York, 1976; McGeer E G, et al, Glutamine, Glutamate, and GABA in the Central Nervous System; Hertz L, Kvamme E, McGeer E G, Schousbal A, eds., Liss: New York, 1983; 3-17). The loss of GABA signaling, by a reduction in GABA release, loss of neurons which synthesize GABA, or antagonism of GABA receptors leads to disinhibition, overexcitation. Depending on the specific brain region involved, this loss of signaling may result in epilepsy, movement disorders or other neurological deficits and symptoms.

Gamma aminobutyric acid (GABA) and glutamic acid are two major neurotransmitters involved in the regulation of brain neuronal activity. GABA is the major inhibitory neurotransmitter and L-glutamic acid is an excitatory transmitter (Roberts et al. GABA in Nervous System Function, Raven Press: New York, 1976; McGeer et al. Glutamine, Glutamate, and GABA in the Central Nervous System; Hertz L, Kvamme E, McGeer E G, Schousbal A, eds., Liss: New York, 1983; 3-17). GABA is released from dopaminergic cells. An imbalance in the concentration of these neurotransmitters can lead to convulsive states. When the concentration of GABA diminishes below a threshold level in the brain, convulsions result (Karlsson et al., (1974) *Biochem. Pharmacol.* 23:3053-3061). When the GABA levels rise in the brain the convulsions terminate (Hayashi (1959) supra). In several convulsive disorders there is concomitant with reduced brain GABA levels, a diminished level of glutamic acid decarboxylase (GAD) activity (McGeer et al., GABA in Nervous System Function; Roberts E, Chase T N, Tower D B, eds., Raven Press: New York 1976:487-495; Butterworth et al., (1983) *Neurochem.* 41:440-447). The concentrations of GAD and GABA vary in parallel (i.e., are positively correlated) because decreased GAD concentration results in lower GABA production.

GABA interacts with a least two receptors, GABA-A and GABA-B. GABA-A receptors have been well characterized and are coupled to chloride channels (Bormann (1988) *Trends Neurosci.* 11: 112-116). GABA-A receptors are related to ligand gated ion channels belonging to the same superfamily as the nicotrinic receptor for acetylcholine. In contrast, GABA-B receptors are less well understood, although reports describe that the GABA-B receptors are coupled to either calcium or potassium channels (Bormann (1988) *Trends Neurosci.* 11:112-116 supra).

The majority of neurons in the striatum (caudate-putamen, dorsal striatum; nucleus accumbens, ventral striatum) and in striatal projection regions (the pallidum, the entopeduncular nucleus and substantia nigra reticulata) use GABA as transmitter and express GAD in the synthesis of GABA.

There are two main forms of GAD present in the vertebrate brain, GAD65 and GAD67, which are the products of two separate genes (Bu et al., 1992). Both forms of the protein are co-expressed throughout the brain but differ in their structure, subcellular localization and regulation. These differences suggest the two GAD isoforms may play differing roles in GABA-mediated neurotransmission.

Human GAD65 and GAD67 have been isolated and cloned by Bu et al. (1992) *Proc Natl Acad Sci* 89:2115-2119. Human GAD65 cDNA encodes a Mr 65,000 polypeptide, with 585 amino acid residues (Genbank Accession No. NM000818; M81882), Human GAD67 encodes a Mr 67,000 polypeptide, with 594 amino acid residues (Genbank Accession No. NM013445; M81883).

The human GAD proteins are comprised of two distinct domains. The C-terminal domain, which contains the catalytic site and cofactor binding site, is relatively conserved between human GAD65 and GAD67 with 73% identity. The N-terminus, which contains a membrane association domain, is highly divergent with only 23% identity (Bu et al., 1992).

Targeting of GAD65 to the golgi is mediated by a 27 amino acid domain in the N-terminus, which is not present in GAD67. In CHO (Chinese Hamster Ovary) and COS cells, membrane association of GAD67 is dependent on the presence of GAD65, presumably through heterodimer formation (Dirkx R, 1995). Targeting to presynaptic clusters is mediated by a palmitoylated 60 amino acid N-terminal domain of GAD65 (Kanaani et al., 2002).

An immunoprecipitation study determined that 33% of GAD protein in rat brain extract is present as GAD65/67 heterodimers (Kanaani et al., 1999). Similarly, in another study 27% of GAD protein isolated from rat cerebellum was in the form of GAD65/67 heterodimers (Sheikh and Martin, 1996). GAD67 has, however, been found to associate with membranes in GAD65−/− mice, suggesting that axonal targeting and membrane association can occur via a mechanism independent of GAD65 (Kanaani et al., 1999).

Both GAD65 and GAD67 require the presence of the cofactor pyridoxal phosphate (PLP) for enzyme activity (Martin et al., 1991). Half of GAD65 protein occurs in the inactive apoenzyme form without bound PLP whereas GAD67 occurs mostly in the active holoenzyme form (Erlander et al., 1991). This inactive pool of "stored" GAD has been postulated to be available for activation at times of high or sudden demand for GABA.

There are marked differences in the amount and activity of GAD protein in different areas of the rat brain. The amount of GAD65 was found by immunoblotting to be 77-89% of total GAD protein in twelve brain areas analyzed which correlated with total GAD activity (Sheikh et al., 1999).

Although GAD65 is the predominant form of GAD present in rat brain, there is evidence from knockout mouse studies that GAD67 synthesizes the majority of GABA in the brain. GAD67$^{-/-}$ mice do not display defects in brain morphology at birth but die soon after due to a cleft palate (Asada et al., 1997; Condie et al., 1997). GAD activity and GABA content in the cerebral cortex is reduced to 20% and 7% respectively in newborn GAD67$^{-/-}$ mice (Asada et al., 1997). GAD65-/- mice are viable but GABA levels are low for the first two months after birth (Stork et al., 2000). Adult rats display abnormal neural activity with spontaneous seizures and paroxysmal discharges (Kash et al., 1997). They also have increased susceptibility to picrotoxin induced seizures than their wild type litter mates (Asada et al., 1996). From these observations, it is obvious that although GAD65 and GAD67 contribute to a metabolic pool of GABA, their roles with respect to inhibitory neurotransmission are different. It is possible that due to its presence throughout the neurons, predominantly in the holoenzyme form, GAD67 may contribute to the basic requirements of inhibitory neurotransmission. The low saturation of GAD65 by PLP, combined with the subcellular distribution in axon terminals and anchoring to synaptic vesicles suggest that GAD65 may be involved in the prevention of hyperexcitability by its rapid activation and loading of GABA into vesicles for rapid secretion.

II. Neurological and Other Disorders

Diseases such as Parkinson's disease, Huntington's disease, Amyotrophic Lateral Sclerosis (ALS or Lou Gehrig's Disease), Epilepsy and Alzheimer's disease, have proved difficult to treat. Few, if any therapies, have proved effective in slowing or arresting the degenerative process associated with these diseases.

In Parkinson's Disease (PD), the primary neurochemical disturbance is believed to be the loss of substantia nigra (SN) dopaminergic (DA) neurons. This loss of DA neurons leads to a profound deficit of DA in the projection areas of the caudate and putamen and results in a loss of signaling through dopamine receptors in the postsynaptic neurons. These neurons, via efferents referred to as the direct and indirect pathways, synapse on other cells in the basal ganglia circuitry. Of most relevance to PD, the loss of dopamine receptors in the basal ganglia circuitry leads to loss of drive in the GABAergic inhibitory input to the subthalamic nucleus.

The loss of inhibitory GABAergic drive to the subthalamic nucleus (STN) results in increased activity of the STN which sends excitatory (glutamatergic) afferents to the ventromedial (VM) thalamus, the substantia nigra pars reticulata (SNPR) and a lesser projection to the pars compacta, as well as other cells within the basal ganglia including the globus pallidus. When the concentration of GABA diminishes below a threshold level in the brain, movement disorders and convulsions may result (See e.g., Karlsson et al, (1974) *Biochem. Pharmacol* 23:3053-3061). GABA synthesis is regulated by glutamic acid decarboxylase (GAD). GAD is present in the brain as two isoforms, GAD65 and GAD67. When the GABA levels rise in the brain the convulsions terminate (See e.g., Hayashi (1959) *Physiol.* 145:570-578). In convulsive disorders, the reduction in brain GABA levels is often paralleled by a diminished level of GAD (McGeer, et al. GABA in Nervous System Function; Roberts E, Chase T N, Tower D B, eds., Raven Press: New York 1976:487-495; Butterworth et al. (1983) *Neurochem.* 41:440-447; Spokes et al. (1978) *Adv. Exp. Med. Biol.* 123:461-473).

Levodopa (L-dopa) has historically been the medication of choice to treat Parkinson's disease. L-dopa is a precursor to dopamine and is able to cross the blood-brain barrier to target the brain. Unfortunately, the response with L-dopa is not sustainable. Most patients develop adverse effects after long-term usage of L-dopa, and often the benefits of treatment wane as the disease progresses.

Other methods for treating Parkinson's disease include transplantation of cells used to repair regions of the brain damaged by neurodegeneration. These cells can be engineered to secrete neuroactive substances such as L-dopa. The procedure typically involves cell transplantation into the striatum. However, cell transplantation is a complicated procedure which requires donor tissue, and there have been reports of mortality associated with this procedure.

Alternative forms of treating Parkinson's disease involve implanting devices for deep-brain stimulation (DBS) in specific regions of the brain. For example, DBS of the STN. These devices are typically electrodes implanted into the STN. The electrode is then stimulated at a desired frequency to reduce the effect of Parkinson's disease. The significance of the STN overactivity is reflected in the success of ablative surgery of the STN in both animal models of Parkinson's disease, as well as in human Parkinson's disease itself. In addition to ablation, implantation of electronic stimulators are commonly employed. The mechanism of the stimulators is believed to be mediated by local inhibition (via GABA signaling), and is replicated by the local infusion of GABA agonists.

Like Parkinson's disease, methods for treating epilepsy include the use of anti-epileptic drugs, such as sodium valporate (Epilim). Available drugs reduce seizure frequency in the majority of patients, but it is estimated that only about forty percent are free of seizures despite optimal treatment. Other forms of treatment include DBS of certain regions of the brain, such as the VIM (ventral intermediate thalamus), subthalamic nucleus, and internal globus pallidus. However, the DBS procedure is not always effective in many patients who require repeated treatment.

Each of these approaches, surgical ablation, electrical stimulation and infusion of pharmacological GABA agonists is effective in disease palliation, but each has significant adverse effects. For example, extensive invasive surgery, a high risk of infection and potential damage to the brain and in the case of drug infusion, very transient efficiency.

Thus, the treatments for neurodegenerative disorders are palliative at best, with limited and transient efficacy. Therefore, a need exists for a therapeutic approach which has advantages in targeting specificity, both short and long-term efficacy, as well as neuroprotection, without extensive surgery or side-effects.

SUMMARY OF THE INVENTION

The invention is drawn to a novel glutamic acid decarboxylase (GAD). More specifically this invention relates to novel chimeric GAD polypeptides and polynucleotides which encode novel GAD polypeptides ("Chimeric GAD"), antibodies and other molecules which bind the polypeptides and/or polynucleotides of the invention, compositions comprising the polypeptides, polynucleotides or antibodies or other binding molecules of the invention as well as methods of use of any of the foregoing.

More specifically, one aspect of the invention provides for novel chimeric polypeptides. The invention also provides polypeptides that have substantial homology to the foregoing novel chimeric polypeptides, modified forms of the novel chimeric polypeptides fragments of the polypeptides. The invention also includes successors or metabolites of the novel chimeric polypeptides in biological pathways. The invention also provides molecules that comprise a novel chimeric polypeptide, homologous polypeptide, a modified novel chimeric polypeptide or a fragment, successor or metabolites polypeptide marker (e.g., a fusion proteins). As used herein, the term "polypeptides of the invention" shall be understood to include all of the foregoing.

Another aspect of the invention provides polynucleotides encoding polypeptides of the invention ("novel chimeric polynucleotides"). The invention also provides polynucleotides that have substantial homology to novel chimeric polynucleotides, modified novel chimeric polynucleotides, and fragments of novel chimeric polynucleotides. The invention also provides molecules that comprise a novel chimeric polynucleotide, homologous polynucleotide, a modified novel chimeric polynucleotide or a fragment of a novel chimeric polynucleotide (e.g., a vector). The novel chimeric polynucleotides of the present invention are intended to include analogs, compounds having a native polypeptide sequence and structure with one or more amino acid additions, substitutions (generally conservative in nature) and/or deletions, relative to the native molecule, so long as the modifications do not alter the differential expression of the marker. As used herein, the term "polynucleotides of the invention" shall be understood to include all of the foregoing.

Another aspect of the invention provides molecules that specifically bind to a polypeptide of the invention, metabolite of the invention or polynucleotide of the invention. The binding molecule may be an antibody, antibody fragment, or other molecule. The invention also provides methods for producing a binding molecule that specifically recognizes a polypeptide of the invention, metabolite of the invention or polynucleotide of the invention.

Another aspect of the invention provides compositions comprising a polypeptide of the invention, metabolite of the invention or polynucleotide of the invention, a binding molecule (e.g., an antibody) that is specific for a polypeptide of the invention, metabolite of the invention or polypeptide of the invention, an inhibitor of a polypeptide of the invention, metabolite of the invention or polynucleotide of the invention, or another molecule that can increase or decrease the level or activity of a polypeptide of the invention, metabolite of the invention or polynucleotide of the invention. Such compositions may be pharmaceutical compositions formulated for use as therapeutics.

Another aspect of the invention provides methods for treating AD by administering a therapeutic agent to a subject that increases or decreases the level or activity of a polypeptide of the invention, metabolite of the invention or polynucleotide of the invention. For polypeptides of the invention, metabolites of the invention or polynucleotides of the invention that are increased in samples obtained from an AD subject, the method comprises administering a therapeutic agent that decreases (i.e., bring toward the normal range) the level or activity of the polypeptide, metabolite or polynucleotide. Similarly, for polypeptides of the invention, metabolites of the invention or polynucleotides of the invention that are decreased in samples obtained from an AD subject, the method comprises administering a therapeutic agent that increases the level or activity of the polypeptide, metabolite or polynucleotide.

Another aspect of the invention provides a method for detecting a polypeptide of the invention, metabolite of the invention or polynucleotide of the invention. In one embodiment, the method comprises contacting a biological sample obtained from a subject with a binding molecule (e.g., an antibody) under conditions that permit the formation of a stable complex, and detecting any stable complexes formed. In another embodiment, the method comprises determining the activity of a polypeptide of the invention, metabolite of the invention or polynucleotide of the invention. In another embodiment, the method comprises determining the level of a polypeptide of the invention in a cell obtained from the subject by detecting the presence of a polynucleotide that encodes the polypeptide.

Another aspect of the invention provides compositions comprising a polypeptide of the invention, metabolite of the invention or polynucleotide of the invention, a binding molecule (e.g., an antibody) that is specific for a polypeptide of the invention, metabolite of the invention or polypeptide of the invention, an inhibitor of a polypeptide of the invention, metabolite of the invention or polynucleotide of the invention, or another molecule that can increase or decrease the level or activity of a polypeptide of the invention, metabolite of the invention or polynucleotide of the invention. Such compositions may be pharmaceutical compositions formulated for use as therapeutics.

The invention is also based, at least in part, on the discovery that localized delivery of a vector comprising a therapeutic agent to a specific region of the brain that is overstimulated or disinhibited in neurodegenerative diseases, can reduce the effect of overstimulation and promote the improvement of the neurodegenerative disease. In particular, the invention pertains to methods and compositions used to deliver a vector, (e.g., an adeno-associated virus vector (AAV)) comprising a nucleotide sequence encoding a chimeric glutamic acid decarboxylase (Chimeric GAD) to target relevant cells, such as the hippocampus or the subthalamic nucleus of the basal ganglia, Particularly preferred methods of delivering the vector to specific regions of the brain are those techniques that are simple, safe, and have a lower risk associated with them than lesioning, electrode implantation or cell transplantation. For example, delivery of the vector using stereotactic microinjection techniques, or delivery of the vector using specialized probes, or percutaneous delivery via disruption of the blood-brain barrier. Delivery of the vector using the method of the invention results in minimal immunological or inflammatory responses within the regions of the brain, thus eliminating the need for immunosuppression. After delivery of the vector to a specific region of the brain, regional dispersion and/or diffusion of vector occurs ensuring local distribution of gene and stable gene expression.

The methods and compositions are particularly useful for treating neurodegenerative diseases, such as Parkinson's disease, Huntington's disease, Amyotrophic Lateral Sclerosis (ALS or Lou Gehrig's Disease), Alzheimer's Disease as well as epilepsy.

Accordingly, the invention is directed to a method for treating a neurodegenerative disease in a subject identifying a target site in the central nervous system that requires modification. A vector comprising a nucleotide sequence encoding a Chimeric GAD is then delivered to the target site in the central nervous system. Chimeric GAD is expressed in the target site to treat or reduce the neurodegenerative disease.

In one embodiment, the vector is a viral vector, and is selected from the group consisting of adenovirus vectors, herpes virus vectors, parvovirus vectors, and lentivirus vectors. In a preferred embodiment, the viral vector is an adeno-associated viral vector.

In another embodiment, the vector is a non-viral vector. In a preferred embodiment, the non-viral vector is a liposome-mediated delivery vector.

In one embodiment, the vector is delivered to a specific target site of the central nervous system. In a preferred embodiment, the vector is delivered using stereotactic delivery, or delivery using specialized probes. In a preferred embodiment, the target site of the central nervous system is a region of the brain. In another preferred embodiment, the region of the brain is selected from the group consisting of basal ganglia, subthalamic nucleus (STN), pedunculopontine nucleus (PPN), substantia nigra (SN), thalamus, hippocampus, amygdala, hypothalamus, cortex and combinations thereof. In a more preferred embodiment, the region of brain is the hippocampus. In one embodiment, the neurodegenerative disease is selected from the group consisting of Parkinson's disease and related movement disorders, Alzheimer's disease, senile dementia, Amyloid Lateral Sclerosis (ALS), and epilepsy.

In another aspect, the invention pertains to a method for treating epilepsy in a subject by identifying one or more regions of the brain that require modification. A vector comprising a nucleotide sequence encoding a Chimeric GAD is then delivered to the region of the brain. Chimeric GAD is expressed in the region of the to treat or reduce epilepsy.

In one embodiment, the region of the brain is selected from the group consisting of basal ganglia, subthalamic nucleus (STN), pedunculopontine nucleus (PPN), substantia nigra (SN), thalamus, hippocampus, amygdala, hypothalamus, cortex, and combinations thereof. In a preferred embodiment, the region of brain is the hippocampus.

In another aspect, the invention pertains to a method for treating epilepsy in a subject by identifying one or more regions of the brain that require modification. An adeno-associated viral (AAV) vector comprising a nucleotide sequence encoding a Chimeric GAD is delivered to the region of the brain, and GAD in expressed the region of the brain to treat or reduce epilepsy.

In yet another aspect, the invention pertains to a vector for expression of Chimeric GAD in cells of the central nervous system comprising a tissue specific promoter operably linked to a nucleotide sequence encoding Chimeric GAD, and a post-transcriptional regulatory element.

In one aspect of the invention, the promoter is specific for central nervous system cells and tissues, such as the cells and tissues of the brain. In a preferred embodiment, the promoter is the neuron specific enolase (NSE) promoter.

The vector also preferably comprises post-transcriptional regulatory elements to enhance expression of the encoded protein. In another aspect of the invention, the post-transcriptional regulatory element is the woodchuck post-transcriptional regulatory element. In a preferred embodiment, the Chimeric GAD is selected from the group consisting of SEQ. I.D. NO:2 and SEQ. I.D. NO:4.

BRIEF DESCRIPTION OF FIGURES

Figure 1F:
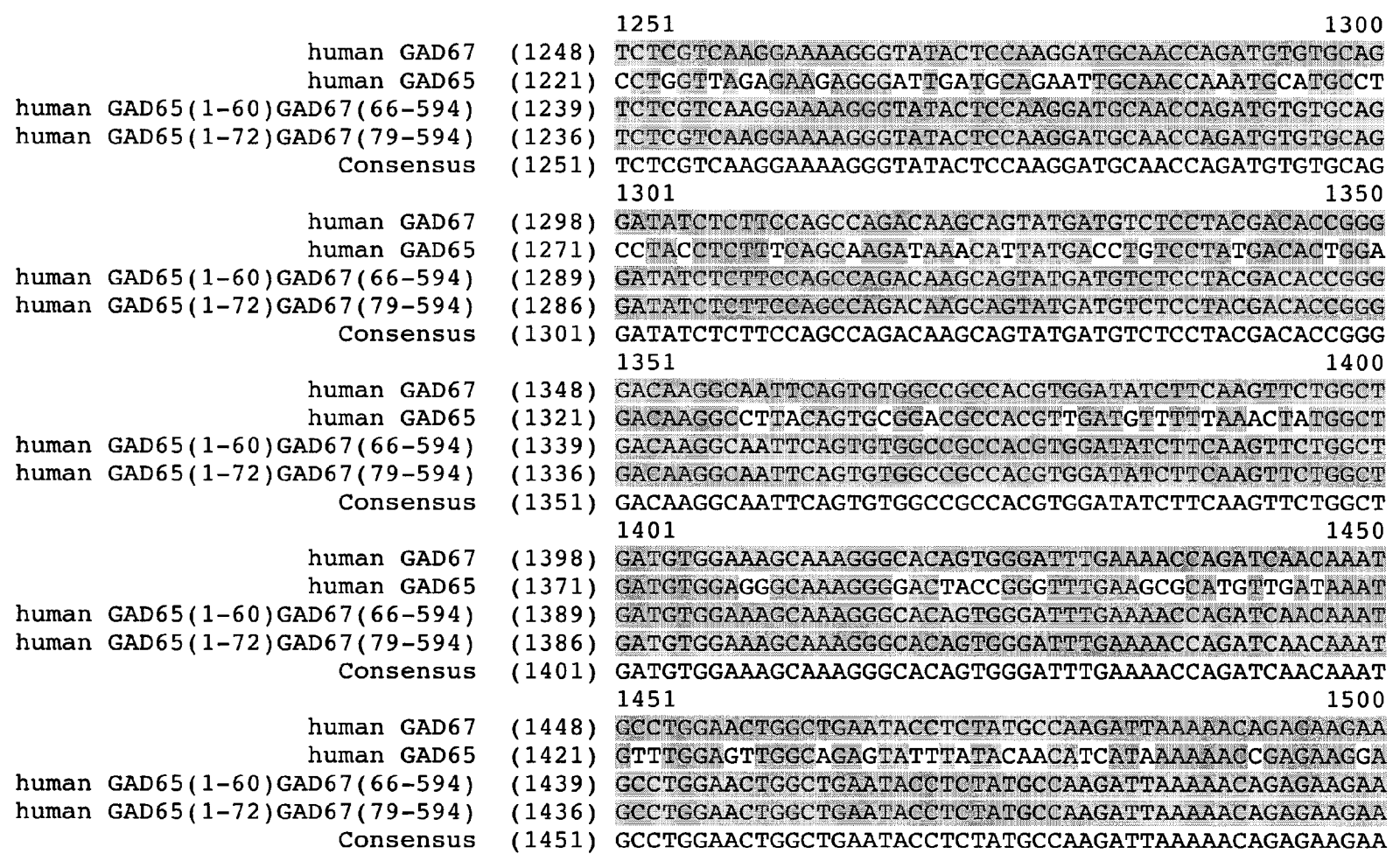
Figure 1G:
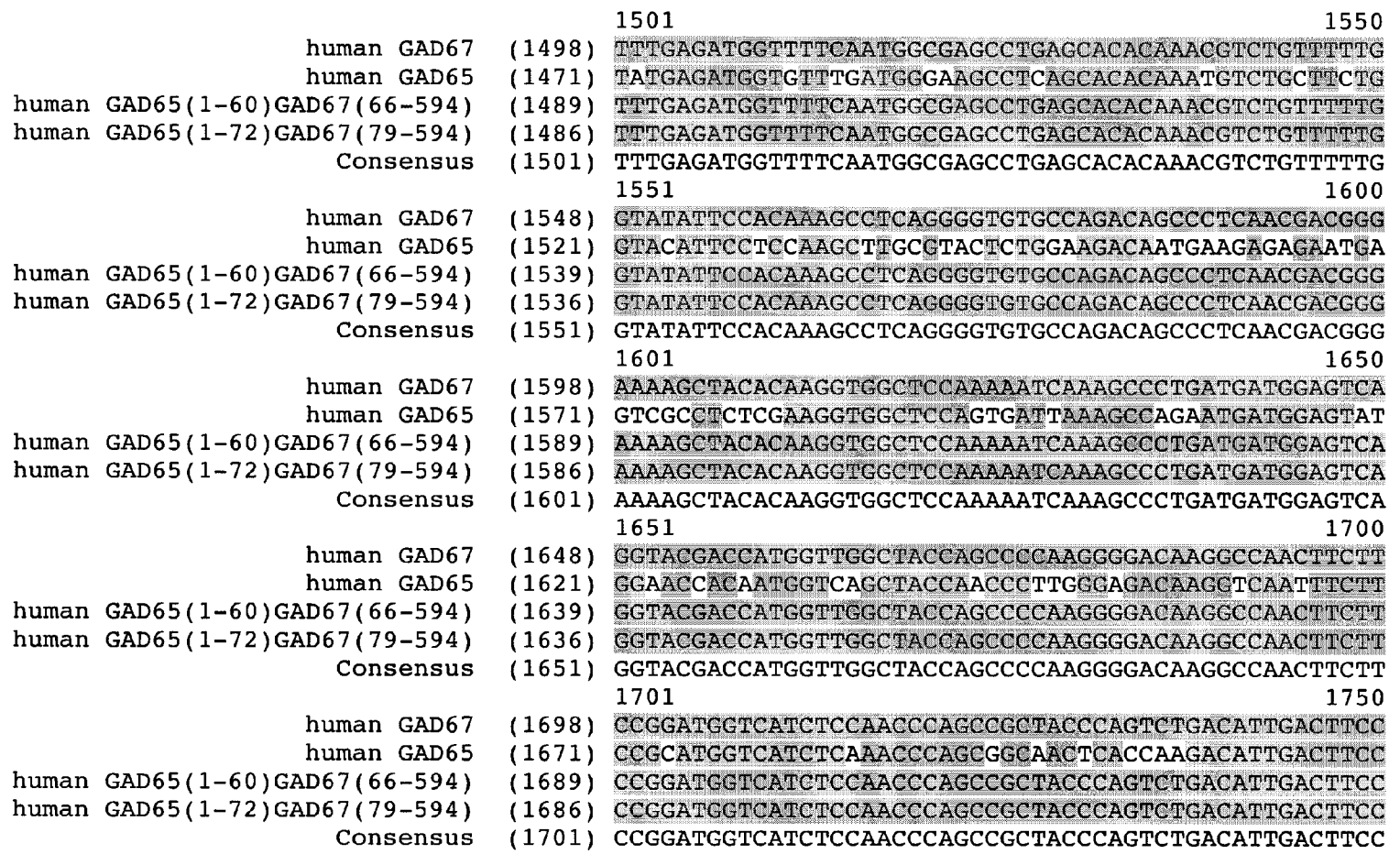

FIG. 1 shows an alignment of the nucleic acid sequences of human GAD67 (SEQ. ID NO. 7), human GAD65 (SEQ. ID NO. 5), Chimeric GAD A (GAD65 (1-60) GAD67(66-594)) (SEQ. ID NO. 1), Chimeric GAD B (GAD65 (1-72) GAD67 (79-594)) (SEQ. ID NO. 3), and a consensus sequence of the foregoing (SEQ. ID NO. 9).

DETAILED DESCRIPTION

Figure 2A:
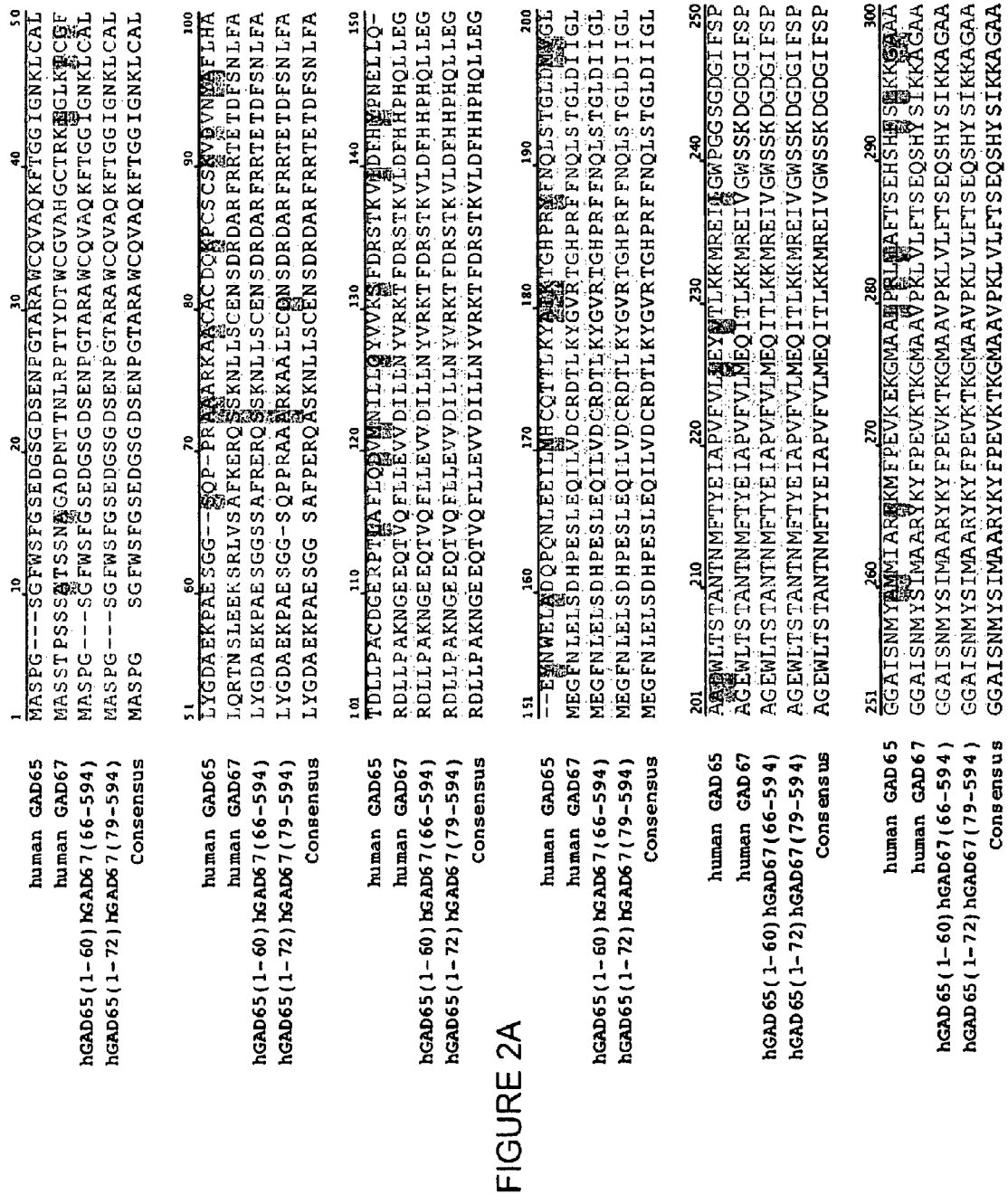
FIG. 2 shows an alignment of the polypeptide sequences of human GAD67 (SEQ. ID NO. 8), human GAD65 (SEQ. ID NO. 6), Chimeric GAD A (GAD65 (1-60) GAD67(66-594)) (SEQ. ID NO. 2), Chimeric GAD B (GAD65 (1-72) GAD67 (79-594)) (SEQ. ID NO. 4), and a consensus sequence of the foregoing (SEQ. ID NO. 10)
Figure 3:
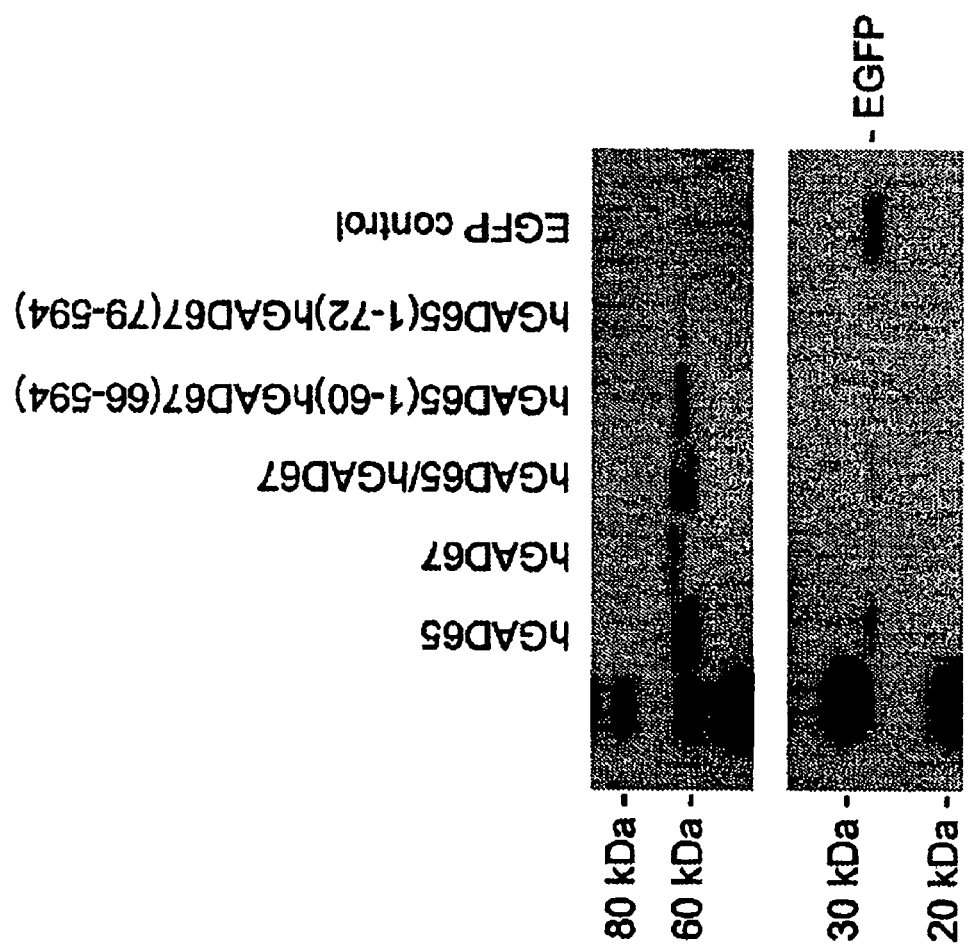
FIG. 3 is a Western Blot of human GAD67, human GAD65, Chimeric GAD A (GAD65 (1-60) GAD67(66-594)), Chimeric GAD B (GAD65 (1-72) GAD67(79-594)) described in Example 1.
Figure 4:
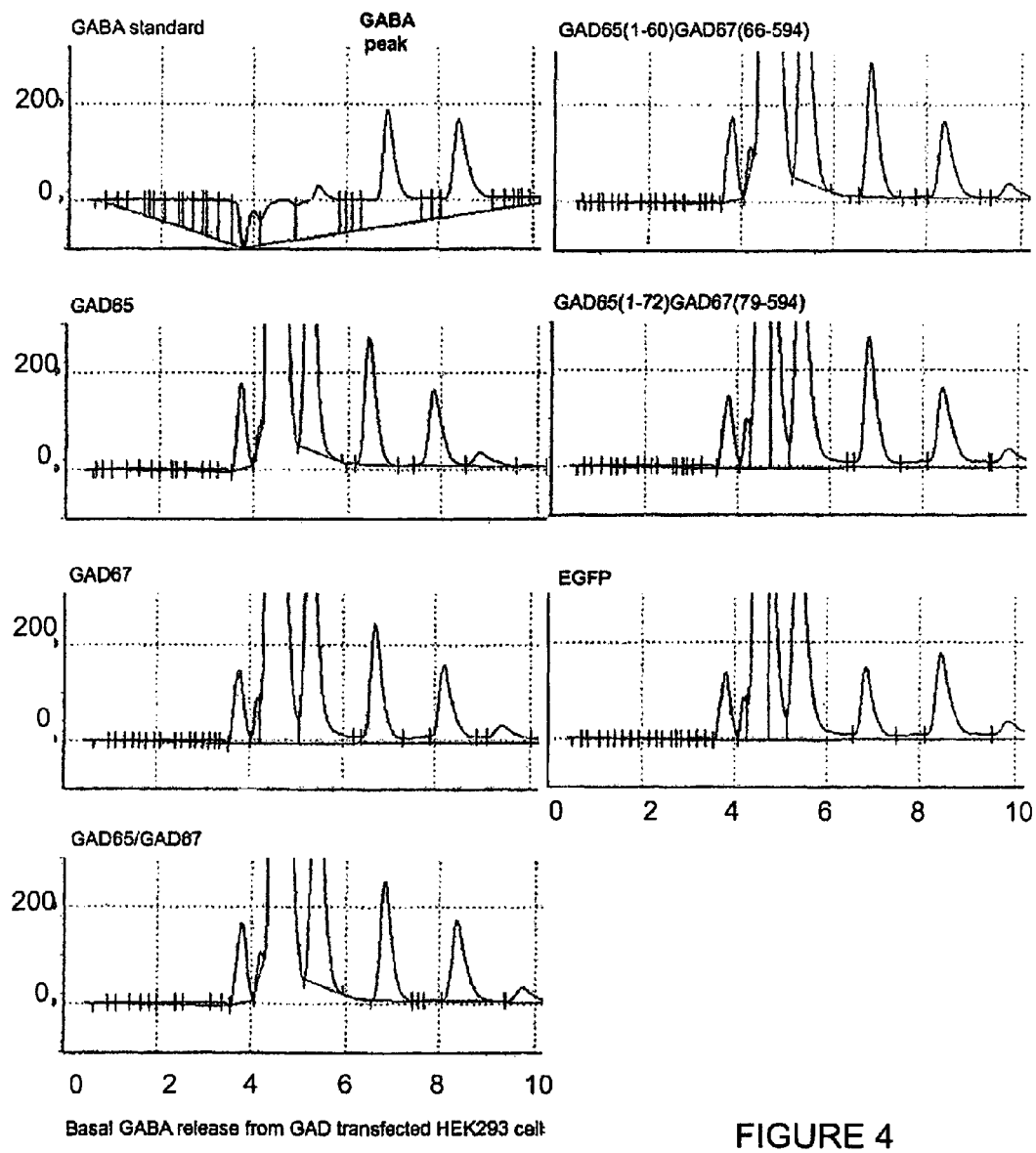
FIG. 4 are HPLC purification results as described in Example 1

The practice of the present invention employs, unless otherwise indicated, conventional methods of virology, microbiology, molecular biology and recombinant DNA techniques within the skill of the art. Such techniques are explained fully in the literature. (See, e.g., Sambrook, et al. Molecular Cloning: A Laboratory Manual (Current Edition); DNA Cloning: A Practical Approach, Vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, Vol. I & II (P. Tijessen, ed.); Fundamental Virology, 2nd Edition, Vol. I & II (B. N. Fields and D. M. Knipe, eds.)).

I. Definitions

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered. The term "central nervous system" or "CNS" as used herein refers to the art recognized use of the term. The CNS pertains to the brain, cranial nerves and spinal cord. The CNS also comprises the cerebrospinal fluid, which fills the ventricles of the brain and the central canal of the spinal cord.

The term "modifies" or "modified" are used interchangeably herein and refer to the up-regulation or down-regulation of a target gene or a target protein. The term modifies or modified also refers to the increase, decrease, elevation, or depression of processes or signal transduction cascades involving a target gene or a target protein. For example, a target protein can be a GABA. Modification to the GABA concentrations may occur when a therapeutic agent, e.g., GAD, alters GABA concentration. For example, modifications that result in an increase in GABA concentration by the expression of GAD in glutaminergic neurons and intrinsic cells of the STN. Modifications can also result from the addition of a therapeutic agent that inactivates GABA aminotransferase. The effect is to block the degradation of GABA and thereby increase its concentration. Numerous mechanism-based inactivators of GABA aminotransferase are known (See e.g., Silverman Mechanism-Based Enzyme Inactivation: Chemistry and Enzymology, Vol. I and II, CRC: Boca Raton 1988). The term modifies also includes increasing, or activating GAD with therapeutic agents that activate GAD, such as sodium valporate. The increase in GAD results in an increase in GABA, which subsequently reduces overstimulation of basal ganglia circuits.

Non-limiting examples of modifications includes modifications of morphological and functional processes, under- or over production or expression of a substance or substances, e.g., a neurotransmitter, by neural cells, failure of neural cells to produce a substance or substances which it normally produces, production of substances, e.g., neurotransmitters, and/or transmission of electrical impulses.

The term "tissue-specific promoter" as used herein refers to a promoter that is operable in cells of the central nervous system (CNS). Examples of promoters for the CNS include but are not limited to, neuron-specific promoters (e.g., the neurofilament promoter; Byrne and Ruddle (1989) *Proc. Natl. Acad. Sci. USA* 86:5473-5477) and glial specific promoters (Morii et al. (1991) *Biochem. Biophys Res. Commun.* 175: 185-191). Preferably, the promoter is tissue specific and is essentially not active outside the central nervous system, or the activity of the promoter is higher in the central nervous system that in other systems. For example, a promoter specific for the spinal cord, brainstem, (medulla, pons, and midbrain), cerebellum, diencephalon (thalamus, hypothalamus), telencephalon (corpus striatum, cerebral cortex, or within the cortex, the occipital, temporal, parietal or frontal lobes), STN, SN, or combinations, thereof. The promoter may also be one that can be used in combination with an AAV to result in higher expression. For example, a cytomegalovirus enhancer/chicken-Actin (CBA) hybrid promoter that functions in cells of the CNS (Xu et al. (2001) *Hum Gene Ther.* 12:563-73).

The terms "neurodegenerative disorder" or a "neurological disorder" as used herein refers to a disorder which causes morphological and/or functional abnormality of a neural cell or a population of neural cells. The neurodegenerative disorder can result in an impairment or absence of a normal neurological function or presence of an abnormal neurological function in a subject. For example, neurodegenerative disorders can be the result of disease, injury, and/or aging. Non-limiting examples of morphological and functional abnormalities include physical deterioration and/or death of neural cells, abnormal growth patterns of neural cells, abnormalities in the physical connection between neural cells, under- or over production of a substance or substances, e.g., a neurotransmitter, by neural cells, failure of neural cells to produce a substance or substances which it normally produces, production of substances, e.g., neurotransmitters, and/or transmission of electrical impulses in abnormal patterns or at abnormal times. Neurodegeneration can occur in any area of the brain of a subject and is seen with many disorders including, for example, head trauma, stroke, ALS, multiple sclerosis, Huntington's disease, Parkinson's disease, and Alzheimer's disease.

As used herein, the terms "Parkinson's subject" and "a subject who has Parkinson's" are intended to refer to subjects who have been diagnosed with Parkinson's or probable Parkinson's. The terms "non-Parkinson's subject" and "a subject who does not have Parkinson's" are intended to refer to a subject who has not been diagnosed with Parkinson's or probable Parkinson's. A non-Parkinson's subject may be healthy and have no other disease, or they may have a disease other than Parkinson's. The term "subject," as used herein, refers to any living organism capable of eliciting an immune response. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, Parkinson's adult and newborn subjects, as well as fetuses, whether male or female, are intended to be covered.

As used herein, the term "antibody" refers to an immunoglobulin molecule capable of binding an epitope present on an antigen. The term is intended to encompasses not only intact immunoglobulin molecules such as monoclonal and polyclonal antibodies, but also bi-specific antibodies, humanized antibodies, chimeric antibodies, anti-idiopathic (anti-ID) antibodies, single-chain antibodies, Fab fragments, F(ab') fragments, fusion proteins and any modifications of the foregoing that comprise an antigen recognition site of the required specificity.

As used herein, the term "biological sample" includes a sample from any body fluid or tissue (e.g., serum, plasma, blood, cerebrospinal fluid, urine, sputum, thin cortical slice, brain tissue homogenate).

As used herein, a component (e.g., a marker) is referred to as "differentially expressed" in one sample as compared to another sample when the method used for detecting the component provides a different level or activity when applied to the two samples. A component is referred to as "increased" in the first sample if the method for detecting the component indicates that the level or activity of the component is higher in the first sample than in the second sample (or if the component is detectable in the first sample but not in the second sample). Conversely, a component is referred to as "decreased" in the first sample if the method for detecting the component indicates that the level or activity of the component is lower in the first sample than in the second sample (or if the component is detectable in the second sample but not in the first sample). In particular, marker is referred to as "increased" or "decreased" in a sample (or set of samples) obtained from an AD subject (or a subject who is suspected of having AD, or is at risk of developing AD) if the level or activity of the marker is higher or lower, respectively, compared to the level of the marker in a sample (or set of samples) obtained from a non-AD subject, or a reference value or range.

As used herein, the term "polypeptide" refers to a single amino acid or a polymer of amino acid residues. A polypeptide may be composed of two or more polypeptide chains. A polypeptide includes a protein, a peptide, an oligopeptide, and an amino acid. A polypeptide can be linear or branched. A polypeptide can comprise modified amino acid residues, amino acid analogs or non-naturally occurring amino acid residues and can be interrupted by non-amino acid residues. Included within the definition are amino acid polymers that have been modified, whether naturally or by intervention, e.g., formation of a disulfide bond, glycosylation, lipidation, methylation, acetylation, phosphorylation, or by manipulation, such as conjugation with a labeling component.

As used herein, a "fragment" of a polypeptide refers to a plurality of amino acid residues comprising an amino acid sequence that has at least 5 contiguous amino acid residues, at least 10 contiguous amino acid residues, at least 20 contiguous amino acid residues or at least 30 contiguous amino acid residues of a sequence of the polypeptide. As used herein, a "fragment" of polynucleotide refers to a single nucleic acid or to a polymer of nucleic acid residues comprising a nucleic acid sequence that has at least 15 contiguous nucleic acid residues, at least 30 contiguous nucleic acid residues, at least 60 contiguous nucleic acid residues, or at least 90% of a sequence of the polynucleotide. In the present invention, the terms "fragments," "analogs," or "derivatives" are used interchangeably to mean a chemical substance that is related to another substance (i.e., marker). The fragment can be, for example, differentially expressed in one sample compared to another sample. In a preferred embodiment, the fragment is differentially expressed in samples from AD subjects when compared to non-AD subjects.

As used herein, a compound is referred to as "isolated" when it has been separated from at least one component with which it is naturally associated. For example, a polypeptide can be considered isolated if it is separated from contaminants including metabolites, polynucleotides and other polypeptides. Isolated molecules can be either prepared synthetically or purified from their natural environment. Standard quantification methodologies known in the art can be employed to obtain and isolate the molecules of the invention.

As used herein, the term "polynucleotide" refers to a single nucleotide or a polymer of nucleic acid residues of any length. The polynucleotide may contain deoxyribonucleotides, ribonucleotides, and/or their analogs and may be double-stranded or single stranded. A polynucleotide can comprise modified nucleic acids (e.g., methylated), nucleic acid analogs or non-naturally occurring nucleic acids and can be interrupted by non-nucleic acid residues. For example a polynucleotide includes a gene, a gene fragment, cDNA, isolated DNA, mRNA, tRNA, rRNA, isolated RNA of any sequence, recombinant polynucleotides, primers, probes, plasmids, and vectors. Included within the definition are nucleic acid polymers that have been modified, whether naturally or by intervention.

In some embodiments, a polypeptide is a member of a biological pathway. As used herein, the term "precursor" or "successor" refers to molecules that precede or follow the polypeptide. Thus, once a polypeptide is identified as a member of one or more biological pathways, the present invention can include additional members of the biological pathway that come before or follow the polypeptide. Such identification of biological pathways and their members is within the skill of one in the art.

As used herein, the term "specifically binding," refers to the interaction between binding pairs (e.g., an antibody and an antigen) with an affinity constant of at most $10^{-6}$ moles/liter, at most $10^{-7}$ moles/liter, or at most $10^{-8}$ moles/liter.

As used herein, two polypeptides are "substantially homologous" when there is at least 70% homology, at least 80% homology, at least 90% homology, at least 95% homology or at least 99% homology between their amino acid sequences, or when polynucleotides encoding the polypeptides are capable of forming a stable duplex with each other. Likewise, two polynucleotides are "substantially homologous" when there is at least 70% homology, at least 80% homology, at least 90% homology, at least 95% homology or at least 99% homology between their amino acid sequences or when the polynucleotides are capable of forming a stable duplex with each other. In general, "homology" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis of similarity and identity, such as ALIGN, Dayhoff, M. O. in Atlas of Protein Sequence and Structure M. O. Dayhoff ed., 5 Suppl. 3:353-358, National biomedical Research Foundation, Washington, D.C., which adapts the local homology algorithm of Smith and Waterman Advances in Appl. Math. 2:482-489, 1981 for peptide analysis. Programs for determining nucleotide sequence similarity and identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent similarity of a particular nucleotide sequence to a reference sequence can be determined using the homology algorithm of Smith and Waterman with a default scoring table and a gap penalty of six nucleotide positions. Alternatively, homology can be determined by hybridization of polynucleotides under conditions that form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art.

The phrase "first phenotypic state" and "second phenotypic state" refers to a cell that displays a particular characteristic typical for that cell. The characteristics can be modified or altered, by genetic intervention, into a second phenotypic state such that the cell displays a characteristic that is different from the original characteristic. For example, delivering GAD to glutamatergic excitatory neurons changes their phenotypic characteristic from excitatory neurons to inhibitory neurons.

The invention is described in more detail in the following subsections:

II. Chimeric GAD65/67

The invention comprises, in part, novel GAD polynucleotide and polypeptide sequences. These novel sequences are chimeric fusions of GAD65 and GAD67). More specifically, they are comprised of an amino-terminal region, derived from GAD65 and an carboxy-terminal region derived from GAD67 ("Chimeric GAD"). Preferably, the GAD chimeras are comprised of an amino-terminal portion that is less than the first 100 amino acids of GAD 65.

In one embodiment, the invention comprises a polypeptide sequence comprised of from about the first 45 amino acids to about the first 99 amino acids of the amino-terminal region of GAD65 and the carboxy-terminal region of GAD 67 beginning at about amino acid 45 to about amino acid 99

In another embodiment, the invention comprises a polynucleotide sequence coding for a GAD Chimeric polypeptide. Preferably, the invention comprises a polynucleotide sequence coding for polypeptide sequence comprised of from about the first 45 amino acids to about the first 99 amino acids of the amino-terminal region of GAD65 and the carboxy-terminal region of GAD 67 beginning at about amino acid 45 to about amino acid 99.

The Chimeric GAD polypeptide and polynucleotide molecules of the invention can be constructed from the GAD65 and GAD67 sequences of any species; preferably from a mammal (including but not limited to simian, feline, murine, canine and bovine forms). In a preferred embodiment, the GAD65 and GAD67 amino acid and nucleotide sequences are those of human GAD65 and GAD67.

Two exemplary constructs were produced. The first construct, Chimeric GAD A, (GAD65(1-60)GAD67(66-594)) (SEQ. ID NO. 1 & SEQ. ID NO. 2), (comprises the first 60 amino acids of GAD65 and amino acids 66-594 of GAD67. The second construct, Chimeric GAD B, comprises the first 72 amino acids of GAD65 and amino acids 79 to 594 of GAD67 (GAD65(1-72)GAD67(79-594)) (SEQ. ID NO. 3 & SEQ. ID NO. 4).

Also contemplated by the invention is a human GAD65/GAD67 consensus chimeric construct. A GAD65/67 consensus chimeric construct was designed by aligning the respective protein sequences of Chimeric GAD A, Chimeric GAD B, human GAD 65 and human GAD 67 and choosing the most prevalent amino acid at a particular position (SEQ. ID NO. 10). A nucleic acid sequence (SEQ. ID NO. 9) which codes for Consensus Chimeric GAD was derived from the amino acid sequence of SEQ. ID NO. 10.

TABLE 1

Chimeric GAD A polynucleotide sequence
(SEQ I.D. NO: 1)

atggcatctccgggctctggcttttggtctttcgggtcggaagatggctc tggggattccgagaatcccggcacagcgcgagcctggtgccaagtggctc agaagttcacgggcggcatcggaaacaaactgtgcgccctgctctacgga gacgccgagaagccggcggagagcggcggctcgagtgccttcaggagag gcaatcctccaagaacctgctttcctgtgaaaacagcgaccgggatgccc gcttccggcgcacagagactgacttctctaatctgtttgctagagatctg cttccggctaagaacggtgaggagcaaaccgtgcaattcctcctggaagt ggtggacatactcctcaactatgtccgcaagacatttgatcgctccacca aggtgctggactttcatcacccacaccagttgctggaaggcatggagggc ttcaacttggagctctctgaccaccccgagtcctggagcagatcctggt tgactgcagagacaccttgaagtatggggttcgcacaggtcatcctcgat ttttcaaccagctctccactggattggatattattggcctagctggagaa tggctgacatcaacggccaataccaacatgtttacatatgaaattgcacc agtgtttgtcctcatggaacaaataacacttaagaagatgagagagatag ttggatggtcaagtaaagatggtgatgggatattttctcctgggggcgcc atatccaacatgtacagcatcatggctgctcgctacaagtacttcccgga agttaagacaaagggcatggcggctgtgcctaaactggtcctcttcacct cagaacagagtcactattccataaagaaagctggggctgcacttggcttt ggaactgacaatgtgattttgataaagtgcaatgaaaggggggaaaataat tccagctgattttgaggcaaaaattcttgaagccaaacagaagggatatg ttccctttatgtcaatgcaactgctggcacgactgtttatggagctttt gatccgatacaagagattgcagatatatgtgagaaatataaccctttggtt gcatgtcgatgctgcctggggaggtgggctgctcatgtccaggaagcacc gccataaactcaacggcatagaaagggccaactcagtcacctggaaccct cacaagatgatgggcgtgctgttgcagtgctctgccattctcgtcaagga aaagggtatactccaaggatgcaaccagatgtgtgcaggatatctcttcc agccagacaagcagtatgatgtctcctacgacaccggggacaaggcaatt cagtgtggccgccacgtggatatcttcaagttctggctgatgtggaaagc aaagggcacagtgggatttgaaaaccagatcaacaaatgcctggaactgg ctgaatacctctatgccaagattaaaaacagagaagaatttgagatggtt ttcaatggcgagcctgagcacacaaacgtctgttttggtatattccaca aagcctcaggggtgtgccagacagccctcaacgacggggaaaagctacaca aggtggctccaaaaatcaaagcctgatgatggagtcaggtacgaccatg gttggctaccagccccaaggggacaaggccaacttcttccggatggtcat ctccaacccagccgctaccagtctgacattgacttcctcattgaggaga tagaaagactggggccaggatctgtaa

TABLE 2

Chimeric GAD A Polypeptide Sequence
(SEQ I.D. NO: 2)

maspgsgfwsfgsedgsgdsenpgtarawcqvaqkftggignklcallyg daekpaesggssafrerqssknllscensdrdarfrrtetdfsnlfardl lpakngeeqtvqfllevvdillnyvrktfdrstkvldfhhphqllegmeg fnlelsdhpesleqilvdcrdtlkygvrtghprffnqlstgldiiglage wltstantnmftyeiapvfvlmeqitlkkmreivgwsskdgdgifspgga isnmysimaarykyfpevktkgmaavpklvlftseqshysikkagaalgf gtdnvilikcnergkiipadfeakileakqkgyvpfyvnatagttvygaf dpiqeiadicekynlwlhvdaawgggllmsrkhrhklngieransvtwnp hkmmgvllqcsailvkekgilqgcnqmcagylfqpdkqydvsydtgdkai qcgrhvdifkfwlmwkakgtvgfenqinkclelaeylyakiknreefemv fngepehtnvcfwyipqslrgvpdspqrreklhkvapkikalmmesgttm vgyqpqgdkanffrmvisnpaatqsdidflieeierlgqdl

TABLE 3

Chimeric GAD B Polynucleotide Sequence
(SEQ I.D. NO: 3)

atggcatctccgggctctggcttttggtctttcgggtcggaagatggctc tggggattccgagaatcccggcacagcgcgagcctggtgccaagtggctc agaagttcacgggcggcatcggaaacaaactgtgcgccctgctctacgga gacgccgagaagccggcggagagcg-
gcgggagccaaccccgcgggccgccgc ccggaaggccgccctcgagtgtgataa-
cagcgaccgggatgcccgcttccggc gcacagagactgacttctctaatct-
gtttgctagagatctgcttccggctaag aacggtgaggagcaaaccgtgcaattc-
ctcctggaagtggtggacatactcct caactatgtccgcaaga-
catttgatcgctccaccaaggtgctggactttcatc acccacaccagttgctggaaggcatg-
gagggcttcaacttggagctctctgac caccccgagtcctggagcagatcctg-
gttgactgcagagacaccttgaagta tggggttcgcacaggtcatcctc-
gattttcaaccagctctccactggattgg atattattggcctagctggagaatggct-
gacatcaacggccaataccaacatg tttacatatgaaattgcaccagt-
gtttgtcctcatggaacaaataacacttaa gaagatgagagagatagttggatggt-
caagtaaagatggtgatgggatatttt ctcctgggggcgccatatccaacatgta-
cagcatcatggctgctcgctacaag tacttcccggaagttaaga-
caaagggcatggcggctgtgcctaaactggtcct cttcacctcagaacagagtcactattc-
cataaagaaagctggggctgcacttg gctttggaactgacaatgt-
gattttgataaagtgcaatgaaaggggggaaaata

TABLE 3-continued

Chimeric GAD B Polynucleotide Sequence
(SEQ I.D. NO: 3)

attccagctgattttgaggcaaaaat-
tcttgaagccaaacagaagggatatgt tcccttttatgtcaatgcaactgctg-
gcacgactgtttatggagcttttgatc cgatacaagagattgcagatatatgt-
gagaaatataacctttggttgcatgtc gatgctgcctggggaggtgggctgct-
catgtccaggaagcaccgccataaact caacggcatagaaagggccaactcagt-
cacctggaaccctcacaagatgatgg gcgtgctgttgcagtgctctgc-
catttctcgtcaaggaaaagggtatactcca aggatgcaaccagatgtgtgcag-
gatatctcttccagccagacaagcagtatg atgtctcctacgacaccggggacaag-
gcaattcagtgtggccgccacgtggat atcttcaagttctggctgatgtggaaag-
caaagggcacagtgggatttgaaaa ccagatcaacaaatgcctggaactggct-
gaatacctctatgccaagattaaaa acagagaagaatttgagatg-
gttttcaatggcgagcctgagcacacaaacgtc tgtttttggtatattccacaaagcct-
caggggtgtgccagacagccctcaacg acgggaaaagctacacaaggtggctc-
caaaaatcaaagccctgatgatggagt caggtacgaccatggttggctaccagc-
cccaaggggacaaggccaacttcttc cggatggtcatctccaaccagccgctac-
ccagtctgacattgacttcctcatt gaggagatagaaagactgggccaggatctgtaa

TABLE 4

Chimeric GAD B Polypeptide Sequence
(SEQ I.D. NO: 4)

maspgsgfwsfgsedgsgdsenpgtarawcqvaqkftggignklcallyg daekpaesggsqppraaarkaalecdnsdrdarfrrtetdfsnlfardll pakngeeqtvqfllevvdillnyvrktfdrstkvldfhhphqllegmegf nlelsdhpesleqilvdcrdtlkygvrtghprffnqlstgldiiglagew ltstantnmftyeiapvfvlmeqitlkkmreivgwsskdgdgifspggai snmysimaarykyfpevktkgmaavpklvlftseqshysikkagaalgfg tdnvilikcnergkiipadfeakileakqkgyvpfyvnatagttvygafd piqeiadicekynlwlhvdaawgggllmsrkhrhklngieransvtwnph kmmgvllqcsailvkekgilqgcnqmcagylfqpdkqydvsydtgdkaiq cgrhvdifkfwlmwkakgtvgfenqinkclelaeylyakiknreefemvf ngepehtnvcfwyipqslrgvpdspqrreklhkvapkikalmmesgttmv gyqpqgdkanffrmvisnpaatqsdidflieeierlgqdl The foregoing are by way of example only. The invention should not limited to the foregoing sequences.

In another embodiment, the invention features a vector comprising a nucleotide sequence encoding a Chimeric GAD.

Also within the scope of the invention is a polypeptide encoded by nucleotide sequence that has at least 60% homology to Chimeric GAD or a fragment thereof. A polypeptide encoded by nucleotide sequence that about 70% homology, about 75% homology, about 80% homology, about 85% homology, about 90% homology, about 95% homology, about 99% homology to GAD65 or a fragment thereof. Also within the scope of the invention is a polypeptide encoded by nucleotide sequence that has at least 60% homology to GAD67 or a fragment thereof. A polypeptide encoded by nucleotide sequence that about 70% homology, about 75% homology, about 80% homology, about 85% homology to Chimeric GAD or a fragment thereof.

III. Binding Molecules

In one aspect, the invention provides molecules that specifically bind to a Chimeric GAD polypeptide or polynucleotide. The binding molecules include antibodies and antibody fragments.

In one aspect, the invention provides antibodies that specifically bind to the polypeptides of SEQ. I.D. NO: 2 or SEQ. I.D. NO: 4, or to a molecule that comprises a foregoing component.

In another embodiment, the invention provides antibodies that specifically bind to a polypeptide having substantial homology with SEQ. I.D. NO:2 or SEQ. I.D. NO:4, or to a molecule that comprises a foregoing polypeptide.

In another embodiment, the invention provides antibodies that specifically bind to a component that is a fragment, modification, precursor or successor of Chimeric GAD.

In another embodiment, the invention provides antibodies that specifically bind to a Chimeric GAD polypeptide or polynucleotide that is structurally different from a what has been described but has the same (or nearly the same) function or properties, or to a molecule that comprises a foregoing component.

Certain antibodies that specifically bind polypeptide markers, metabolite markers or polynucleotide markers of the invention already may be known and/or available for purchase from commercial sources. In any event, the antibodies of the invention may be prepared by any suitable means known in the art. For example, antibodies may be prepared by immunizing an animal host with a marker or an immunogenic fragment thereof (conjugated to a carrier, if necessary). Adjuvants (e.g., Freund's adjuvant) optionally may be used to increase the immunologic response. Sera containing polyclonal antibodies with high affinity for the antigenic determinant can then be isolated from the immunized animal and purified.

Alternatively, antibody-producing tissue from the immunized host can be harvested and a cellular homogenate prepared from the organ can be fused to cultured cancer cells. Hybrid cells which produce monoclonal antibodies specific for a marker can be selected. Alternatively, the antibodies of the invention can be produced by chemical synthesis or by recombinant expression. For example, a polynucleotide that encodes the antibody can be used to construct an expression vector for the production of the antibody. The antibodies of the present invention can also be generated using various phage display methods known in the art.

Antibodies that specifically bind markers of the invention can be used, for example, in methods for detecting Chimeric GAD polypeptides or polynucleotides using methods and techniques well-known in the art. In some embodiments, for example, the antibodies are conjugated to a detection molecule or moiety (e.g., a dye, and enzyme) and can be used in ELISA or sandwich assays to detect markers of the invention.

In another embodiment, antibodies against a polypeptide or polynucleotide of the invention can be used to assay a tissue sample (e.g., a thin cortical slice) for the marker. The antibodies can specifically bind to the marker, if any, present in the tissue sections and allow the localization of the marker in the tissue. Similarly, antibodies labeled with a radioisotope may be used for in vivo imaging or treatment applications.

IV. Methods for Detecting

The polypeptides or polynucleotides of the invention may be detected by any method known to those of skill in the art, including without limitation LC-MS, GC-MS, immunoassays, hybridization and enzyme assays. The detection may be quantitative or qualitative. A wide variety of conventional techniques are available, including mass spectrometry, chromatographic separations, 2-D gel separations, binding assays (e.g., immunoassays), competitive inhibition assays, and so on. Any effective method in the art for measuring the present/absence, level or activity of a metabolite, polypeptide or polynucleotide is included in the invention. It is within the ability of one of ordinary skill in the art to determine which method would be most appropriate for measuring a specific marker. Thus, for example, a ELISA assay may be best suited for use in a physician's office while a measurement requiring more sophisticated instrumentation may be best suited for use in a clinical laboratory. Regardless of the method selected, it is important that the measurements be reproducible.

The polypeptides or polynucleotides of the invention can be measured by mass spectrometry, which allows direct measurements of analytes with high sensitivity and reproducibility. A number of mass spectrometric methods are available. Electrospray ionization (ESI), for example, allows quantification of differences in relative concentration of various species in one sample against another; absolute quantification is possible by normalization techniques (e.g., using an internal standard). Matrix-assisted laser desorption ionization (MALDI) or the related SELDI® technology (Ciphergen, Inc.) also could be used to make a determination of whether a marker was present, and the relative or absolute level of the marker. Mass spectrometers that allow time-of-flight (TOF) measurements have high accuracy and resolution and are able to measure low abundant species, even in complex matrices like serum or CSF.

For protein markers, quantification can be based on derivatization in combination with isotopic labeling, referred to as isotope coded affinity tags ("ICAT"). In this and other related methods, a specific amino acid in two samples is differentially and isotopically labeled and subsequently separated from peptide background by solid phase capture, wash and release. The intensities of the molecules from the two sources with different isotopic labels can then be accurately quantified with respect to one another.

In addition, one- and two-dimensional gels have been used to separate proteins and quantify gels spots by silver staining, fluorescence or radioactive labeling. These differently stained spots have been detected using mass spectrometry, and identified by tandem mass spectrometry techniques.

In a preferred embodiment, the polypeptides or polynucleotides are measured using mass spectrometry in connection with a separation technology, such as liquid chromatography-mass spectrometry or gas chromatography-mass spectrometry. In particular, coupling reverse-phase liquid chromatography to high resolution, high mass accuracy ESI time-of-flight (TOF) mass spectroscopy allows spectral intensity measurement of a large number of biomolecules from a relatively small amount of any complex biological material. Analyzing a sample in this manner allows the marker (characterized by a specific RT and m/z) to be determined and quantified.

As will be appreciated by one of skill in the art, many other separation technologies may be used in connection with mass spectrometry. For example, a wide selection of separation columns is commercially available. In addition, separations may be performed using custom chromatographic surfaces (e.g., a bead on which a marker specific reagent has been immobilized). Molecules retained on the media subsequently may be eluted for analysis by mass spectrometry.

Analysis by liquid chromatography-mass spectrometry produces a mass intensity spectrum, the peaks of which represent various components of the sample, each component having a characteristic mass-to-charge ratio (m/z) and retention time (RT). The presence of a peak with the m/z and RT of a marker indicates that the marker is present. The peak representing a polypeptide o polynucleotide may be compared to a corresponding peak from another spectrum (e.g., from a control sample) to obtain a relative measurement. Any normalization technique in the art (e.g., an internal standard) may be used when a quantitative measurement is desired. "Deconvoluting" software is available to separate overlapping peaks. The retention time depends to some degree on the conditions employed in performing the liquid chromatography separation. The preferred conditions, those used to obtain the retention times that appear in the Tables, are set forth in the Example. The mass spectrometer preferably provides high mass accuracy and high mass resolution. The mass accuracy of a well-calibrated Micromass TOF instrument, for example, is reported to be approximately 2 mDa, with resolution m/$\Delta$m exceeding 5000.

In other preferred embodiments, the level of the polypeptides or polynucleotides may be determined using a standard immunoassay, such as sandwiched ELISA using matched antibody pairs and chemiluminescent detection. Commercially available or custom monoclonal or polyclonal antibodies are typically used. However, the assay can be adapted for use with other reagents that specifically bind to the molecule. Standard protocols and data analysis are used to determine the marker concentrations from the assay data.

A number of the assays discussed above employ a reagent that specifically binds to the polypeptide or polynucleotide of the invention. Any molecule that is capable of specifically binding to a molecule of the invention is included within the invention. In some embodiments, the binding molecules are antibodies or antibody fragments. In other embodiments, the binding molecules are non-antibody species. Thus, for example, the binding molecule may be an enzyme for which the marker is a substrate. The binding molecules may recognize any epitope of the targeted markers.

As described above, the binding molecules may be identified and produced by any method accepted in the art. Methods for identifying and producing antibodies and antibody fragments specific for an analyte are well known. Examples of other methods used to identify the binding molecules include binding assays with random peptide libraries (e.g., phage display) and design methods based on an analysis of the structure of the marker.

Finally, the chromatographic separation techniques described above also may be coupled to an analytical technique other than mass spectrometry such as fluorescence detection of tagged molecules, NMR, capillary UV, evaporative light scattering or electrochemical detection.

Measurement of the relative amount of an RNA or protein molecule of the invention may be by any method known in the art (see, e.g., Sambrook, J., Fritsh, E. F., and Maniatis, T.

Molecular Cloning: A Laboratory Manual. 2nd, ed., Cold Spring Harbor Laboratory, Cold Spring Harbor Laboratory Press, Cold Spring Harbor, N.Y., 1989; and Current Protocols in Molecular Biology, eds. Ausubel et al. John Wiley & Sons: 1992). Typical methodologies for RNA detection include RNA extraction from a cell or tissue sample, followed by hybridization of a labeled probe (e.g., a complementary polynucleotide) specific for the target RNA to the extracted RNA, and detection of the probe (e.g., Northern blotting). Typical methodologies for protein detection include protein extraction from a cell or tissue sample, followed by hybridization of a labeled probe (e.g., an antibody) specific for the target protein to the protein sample, and detection of the probe. The label group can be a radioisotope, a fluorescent compound, an enzyme, or an enzyme co-factor. Detection of specific protein and polynucleotides may also be assessed by gel electrophoresis, column chromatography, direct sequencing, or quantitative PCR (in the case of polynucleotides) among many other techniques well known to those skilled in the art.

Detection of the presence or number of copies of all or a part of a gene of the invention may be performed using any method known in the art. Typically, it is convenient to assess the presence and/or quantity of a DNA or cDNA by Southern analysis, in which total DNA from a cell or tissue sample is extracted, is hybridized with a labeled probe (e.g., a complementary DNA molecule), and the probe is detected. The label group can be a radioisotope, a fluorescent compound, an enzyme, or an enzyme co-factor. Other useful methods of DNA detection and/or quantification include direct sequencing, gel electrophoresis, column chromatography, and quantitative PCR, as is known by one skilled in the art.

Polynucleotide similarity can be evaluated by hybridization between single stranded nucleic acids with complementary or partially complementary sequences. Such experiments are well known in the art.

V. Neurodegenerative Diseases

Generally, the methods and compositions of the invention can be used to change cells from a first phenotypic state to second phenotypic state. The invention also pertains to delivering Chimeric GAD to regions of the brain associated with a particular disease or disorder. These regions vary according to the neurodegenerative disease, but are well know to the skilled artisan. For example, the region of the brain associated with PD can be the STN, while the region of the brain associated with epilepsy can be the hippocampus. it is also to be understood that the various regions of the brain treated with DBS can also be treated with the methods and compositions of the invention.

In particular, the invention pertains to GAD gene transfer into glutamatergic excitatory neurons which leads to an inhibitory bias with altered network activity. This phenotypic shift provides strong neuroprotection and demonstrates there is plasticity between excitatory and inhibitory neurotransmission in the mammalian brain that results in a therapeutic effect. This alteration form a first state to a second state can be used in a umber of neurodegenerative disorders such as those described below.

(a) Parkinson's Disease

Parkinson's disease is associated with a disturbances of posture, locomotion, facial expression or speech. The manifestations may be asymmetric, e.g., a slight tremor of the fingers on one hand at rest, and then become bilateral. Symptoms of Parkinson's disease are caused by loss of nerve cells in the pigmented substantia nigra pars compacta (SNPC) and the locus ceruleus in the midbrain. The striatum or corpus striatum is a structure in the cerebral hemispheres consisting of two basal ganglia (the caudate nucleus and the putamen) and the fiber of the internal capsule that separate them. Parkinson's disease in humans primarily effects the subcortical structures, especially the substantia nigra and the locus ceruleus. It is characterized by the loss of dopamine neurons in the substantia nigra, which have the basal ganglia as their major target organ. Cell loss also occurs in the globus pallidus and putamen.

Parkinson's disease is also associated with eosinophilic intraneural inclusion granules (Lewy bodies) which are present in the basal ganglia, brainstem, spinal cord, and sympathetic ganglia. The pars compacta neurons of the substantia nigra (SN) provide dopaminergic input into the striatum, which is part of the basal ganglia. These dopaminergic neurons modulate a monosynaptic gamma-aminobutyric acid (GABA) inhibitory output in the globus pallidus interna and pars reticulata of the substantia nigra. In Parkinson's disease, loss of dopaminergic cells in the substantia nigra leads to striatal dopamine depletion. This loss of dopamine alters the activity of neurons within the basal ganglia circuitry, including excessive firing and activity of these cells.

The motor abnormalities of Parkinson's disease (PD) are caused by alterations in basal ganglia network activity, including disinhibition of the subthalamic nucleus (STN), and excessive activity of the major output nuclei. Using adeno-associated viral vector-mediated somatic cell gene transfer, glutamic acid decarboxylase (GAD) was expressed, the enzyme that catalyzes synthesis of the neurotransmitter GABA, in excitatory glutamatergic neurons of the STN in an in vivo animal model. The transduced neurons, when driven by electrical stimulation, produced mixed inhibitory responses associated with GABA release. This phenotypic shift resulted in strong neuroprotection of nigral dopamine neurons and rescue of the parkinsonian behavioral phenotype. This strategy suggests that there is plasticity between excitatory and inhibitory neurotransmission in the mammalian brain that could be exploited for therapeutic benefit (See Luo et al., (2002) *Science* 298: 425-429).

Accordingly, a region of the brain associated with Parkinson's disease can be inhibited, reduced, treated, or altered from a first phenotypic state to a second phenotypic state using the methods and compositions of the invention. In particular, a vector comprising a therapeutic agent, e.g., a nucleotide sequence encoding GAD, can be delivered to the site of dopaminergic cell loss or other regions of the basal ganglia and output nuclei. In one embodiment, the vector comprising a therapeutic agent can be delivered to the subthalamic nucleus (SN). In another embodiment, the vector comprising a therapeutic agent can be delivered to the substantia nigra pars reticulata (SNPR).

(b) Alzheimer's Disease

Alzheimer's disease is characterized by the gradual loss of intellectual capabilities. Post-mortem examination of the brain shows a generalized atrophy. There are extensive histological changes in Alzheimer's disease dominated by the presence of intracellular amyloid plaques and neurofibrillary tangles. Plaques and tangles are rare, however, in the basal ganglia and substantia nigra. Many specimens from Alzheimer's disease patients demonstrate a loss of pigmentation in the area of the locus ceruleus, which is a major source of noradrenergic synthesis in the brain. Accordingly, a region of the brain associated with Alzheimer's disease can be inhibited, reduced, treated, or altered from a first phenotypic state to a second phenotypic state using the methods and compositions of the invention.

(c) Epilepsy

Epileptic seizures are the outward manifestation of excessive and/or hypersynchronous abnormal activity of neurons in the cerebral cortex. Seizures are usually self limiting. Many types of seizures occur. The behavioral features of a seizure reflect function of the portion of the cortex where the hyper activity is occurring. Seizures can be generalized, appearing to involve the entire brain simultaneously. Generalized seizures can result in the loss of conscious awareness only and are then called absence seizures (previously referred to as "petit mal"). Alternatively, the generalized seizure may result in a convulsion with tonic-clonic contractions of the muscles ("grand mal" seizure). Some types of seizures, partial seizures, begin in one part of the brain and remain local. The person may remain conscious throughout the seizure. If the person loses consciousness the seizure is referred to as a complex partial seizure.

Simple partial seizures include autonomic and mental symptoms and sensory symptoms such as olfaction, audition, or vision, sometimes concomitant with symptoms of experiences such as deja-vu and jamais-vu. Complex partial seizures often exhibit motion stopping followed by eating-function automatism, and are divided into amygdala-hippocampus seizures and lateral temporal lobe seizures according to localization. In the case of temporal lobe epilepsy, 70-80% of the seizures are hippocampus seizures, in which aura, motion stopping, lip automatism, and clouding of consciousness are successively developed to result in amnesia. When the focus is in the amygdala, there are caused autonomic symptoms such as dysphoria in the epigastrium; phobia; and olfactory hallucination. Lateral temporal lobe seizures include auditory illusion, hallucination, and a dreamy state, and disturbance of speech when the focus is in the dominant hemisphere. Temporal lobe epilepsy exhibits a long-term psychosis-like state in addition to other symptoms and recognition-and-memory disorder more frequently than do other epilepsies. Treatment of temporal lobe epilepsy is carried out through pharmacotherapy employing a maximum dose of a combination of drugs, or through surgical treatment. A complex partial seizure is a partial seizure with impairment of consciousness, and is similar to a seizure that has conventionally been called a psycho-motor seizure or a seizure associated with temporal lobe epilepsy.

The neuromechanism responsible for seizures includes the amygdala, the hippocampus, the hypothalamus, the parolfactory cortex, etc., in addition to the frontal and temporal lobes. The seizures typically last 1-2 minutes or slightly longer, and the onset and cessation of the seizures are not abrupt but gradual.

The existence of a system which can control the propagation and/or the generation of different kinds of seizures is known. The involvement of the substantia nigra, a particular portion of the brain considered to be part of neural circuitry referred to as the basal ganglia (See e.g., Depaulis, et al. (1994) *Prog. Neurobiology*, 42: 33-52). The inhibition of the substantia nigra will increase the threshold for seizure.

The neural connections that make up the basal ganglia are also important in epilepsy. These connections are reviewed by Alexander et. al. (Alexander, et al. *Prog. Brain Res*. 85: 119-146). The substantia nigra receives input from the subthalamic nucleus (STN) which is excitatory and involves glutamate as the neurotransmitter conveying information at the synapse. Bergman et al. have shown that a lesion of the subthalamic nucleus will reduce the inhibitory output of the internal segment of the globus pallidus and substantia nigra reticulata (SN) (Bergman, et al (1990), *Science,* 249: 1436-1438). The subthalamic nucleus receives input from the external segment of the globus pallidus (GPe). This input is inhibitory using GABA as a transmitter substance. Hence, increased activity of the neurons in GPe will increase inhibition of neurons in the subthalamic nucleus which will reduce the excitation of neurons in the substantia nigra.

Accordingly, a region of the brain associated with epilepsy can be inhibited, reduced, treated, or altered from a first phenotypic state to a second phenotypic state using the methods and compositions of the invention. The invention is intended to include all regions of the brain associated with epilepsy. Such regions of the brain include, but are not limited to, the hippocampus, amygdala, and hypothalamus. In a preferred embodiment, the vector carrying the GAD gene is delivered to the hippocampus. Also within the scope of the invention are regions for treatment of epilepsy via DBS, such as cerebellum, caudate, thalamus, mamillary nuclei, anterior nucleus of the thalamus, centromedian nucleus of the thalamus, and subthalamic nucleus.

The kainate model is an epileptic model in which kainic acid, which is one of the excitatory amino acids found in the brain, is injected to nuclei (amygdala, hippocampus, etc.) in the limbic system in an microamount to induce focal epilepsy. The kainate model serves as a model for an epileptic seizure; more particularly, as a model for status epilepticus induced from the limbic system in an acute phase, and as a model for evolution of a spontaneous limbic seizure to a secondary generalized seizure in a chronic phase. The kainate model may also be used as a cortex epilepsy model through injection of kainic acid to the cortex (sensory motor field).

The methods and compositions of the invention can be used to be used to inhibit, reduce, or treat seizures that include, but are not limited to, tonic seizures, tonic-clonic seizures, atypical absence seizures, atonic seizures, myoclonic seizures, clonic seizures, simple partial seizures, complex partial seizures, and secondary generalized seizures.

(d) Metabolic Disorders (i) Obesity

The methods and composition of the invention can also be used to treat or modify obesity in a subject. Mouse models for obesity are known in that art, for example, obese-diabetic mice (ob/ob), and obese-diabetic (db/db) mice from the Jackson Laboratories (Bar Harbor, Me.). (See e.g., Collins et al. (1996) *J Biol Chem* 271:9437-9440; Darling (1996) *Curr Opin Genet Dev* 6:289-294; Andersson (1996) *Ann. Med*. 28:5-7). These animal models can be used to assess the effect of GAD on weight gain, particularly by delivering GAD to the hypothalamus region of the brain. The hypothalamus plays a significant role in obesity. Augmentation of GABA function from neurons within the hypothalamus can result in alteration of metabolic behavior (Boulis et al. (2002) AANS meeting, Chicago (abstract)). Accordingly, a region of the brain associated with obesity can be inhibited, reduced, treated, or altered from a first phenotypic state to a second phenotypic state using the methods and compositions of the invention.

(ii) Diabetes

A summary of insulin-dependent diabetes mellitus and its animal models is described by Wong et al. (1999) *Curr Opin Immunol* 11:643-647. Glutamic acid decarboxylase (GAD) has been associated with diabetes (Baekkeskov et al. (1990) *Nature* 347:151-156). These models can be used to investigate the effect of GAD on diabetes in a animal. A region of the brain associated with diabetes can be inhibited, reduced, treated, or altered from a first phenotypic state using the methods and compositions of the invention.

(e) Pain

The methods and compositions of the invention can also be used to reduce pain by delivering GAD to a region of the brain associated with pain. For example, in Jasmin et al., GABA neurotransmission in the rostral agranular insular cortex (RAIC) of freely moving rats, was altered by locally increasing GABA using two methods: (a) an enzyme inhibitor; and (b) a double-cassette-defective herpes simplex virus vector. Use of gene transfer mediated by a viral vector produced lasting analgesia in the rats by enhancing the descending inhibition of spinal nociceptive neurons (Jasmin et al. (2003) *Nature*, 424:316-320). A region of the brain associated with pain can be inhibited, reduced, treated, or altered from a first phenotypic state using the methods and compositions of the invention.

(f) Visual Cortical Function

The methods and compositions of the invention can also be used to improve visual cortical function be delivering GAD, and to subsequently alter GABA levels in a region of the brain associated with vision. For example, alteration of GABA levels, in a region of the visual cortex (VI) of aged primates can result in improved acuity, improved orientation and direction selectivity, decreased spontaneous activity and an increased ability to signal visual stimuli (Levanthal et al. (2003) *Science* 300:812-815). Accordingly, a region of the brain associated with vision can be inhibited, reduced, treated, or altered from a first phenotypic state using the methods and compositions of the invention.

(g) Other Degenerative Diseases

This invention also relates to compositions and methods of treatment of other degenerative disorders. These include, but are not limited to the following: head and spinal cord trauma; cardiac cell death due to ischemia; tissue and organ death due to transplant rejection; and hearing loss due to autotoxicity.

VI. Vectors

The vectors of the invention can be delivered to the cells of the central nervous system by using viral vectors or by using non-viral vectors. In a preferred embodiment, the invention uses adeno-associated viral vectors comprising the a nucleotide sequence encoding GAD for gene delivery. AAV vectors can be constructed using known techniques to provide at least the operatively linked components of control elements including a transcriptional initiation region, a exogenous nucleic acid molecule, a transcriptional termination region and at least one post-transcriptional regulatory sequence. The control elements are selected to be functional in the targeted cell. The resulting construct which contains the operatively linked components is flanked at the 5' and 3' region with functional AAV ITR sequences.

The nucleotide sequences of AAV ITR regions are known. The ITR sequences for AAV-2 are described, for example by Kotin et al. (1994) *Human Gene Therapy* 5:793-801; Berns "Parvoviridae and their Replication" in Fundamental Virology, 2nd Edition, (B. N. Fields and D. M. Knipe, eds.) The skilled artisan will appreciate that AAV ITR's can be modified using standard molecular biology techniques. Accordingly, AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including but not limited to, AAV-1, AAV-2, AAV-3, AAV-4, AAV-5, AAVX7, AAV-8 and the like. Furthermore, 5' and 3' ITRs which flank a selected nucleotide sequence in an AAV expression vector need not necessarily be identical or derived from the same AAV serotype or isolate, so long as the ITR's function as intended, i.e., to allow for excision and replication of the bounded nucleotide sequence of interest when AAV rep gene products are present in the cell.

The skilled artisan can appreciate that regulatory sequences can often be provided from commonly used promoters derived from viruses such as, polyoma, Adenovirus 2, cytomegalovirus and Simian Virus 40. Use of viral regulatory elements to direct expression of the protein can allow for high level constitutive expression of the protein in a variety of host cells. Ubiquitously expressing promoters can also be used include, for example, the early cytomegalovirus promoter Boshart et al. (1985) *Cell* 41:521-530, herpesvirus thymidine kinase (HSV-TK) promoter (McKnight et al. (1984) *Cell* 37: 253-262), beta-actin promoters (e.g., the human beta-actin promoter as described by Ng et al. (1985) *Mol. Cell. Biol.* 5: 2720-2732) and colony stimulating factor-1 (CSF-1) promoter (Ladner et al. (1987) *EMBO J.* 6: 2693-2698).

Alternatively, the regulatory sequences of the AAV vector can direct expression of the gene preferentially in a particular cell type, i.e., tissue-specific regulatory elements can be used. Non-limiting examples of tissue-specific promoters which can be used include, central nervous system (CNS) specific promoters such as, neuron-specific promoters (e.g., the neurofilament promoter; Byrne and Ruddle (1989) *Proc. Natl. Acad. Sci. USA* 86:5473-5477) and glial specific promoters (Morii et al. (1991) *Biochem. Biophys Res. Commun.* 175: 185-191). Preferably, the promoter is tissue specific and is essentially not active outside the central nervous system, or the activity of the promoter is higher in the central nervous system that in other systems. For example, a promoter specific for the spinal cord, brainstem, (medulla, pons, and midbrain), cerebellum, diencephalon (thalamus, hypothalamus), telencephalon (corpus stratium, cerebral cortex, or within the cortex, the occipital, temporal, parietal or frontal lobes), or combinations, thereof. The promoter may be specific for particular cell types, such as neurons or glial cells in the CNS. If it is active in glial cells, it may be specific for astrocytes, oligodentrocytes, ependymal cells, Schwann cells, or microglia. If it is active in neurons, it may be specific for particular types of neurons, e.g., motor neurons, sensory neurons, or interneurons. Preferably, the promoter is specific for cells in particular regions of the brain, for example, the cortex, stratium, nigra and hippocampus.

Suitable neuronal specific promoters include, but are not limited to, neuron specific enolase (NSE) (Olivia et al. (1991) *Genomics* 10: 157-165, GenBank Accession No: X51956), and human neurofilament light chain promoter (NEFL) (Rogaev et al. (1992) *Hum. Mol. Genet.* 1: 781, GenBank Accession No: L04147). Glial specific promoters include, but are not limited to, glial fibrillary acidic protein (GFAP) promoter (Morii et al. (1991) *Biochem. Biophys. Res. Commun.* 175: 185-191, GenBank Accession No: M65210), S100 promoter (Morii et al. (1991) *Biochem. Biophys. Res. Commun.* 175: 185-191, GenBank Accession No: M65210) and glutamine synthase promoter (Van den et al. (1991) *Biochem. Biophys. Acta.* 2: 249-251, GenBank Accession No: X59834). In a preferred embodiment, the gene is flanked upstream (i.e., 5') by the neuron specific enolase (NSE) promoter. In another preferred embodiment, the gene of interest is flanked upstream (i.e., 5') by the elongation factor 1 alpha (EF) promoter.

The AAV vector harboring the nucleotide sequence encoding a protein of interest, e.g., GAD, and a post-transcriptional regulatory sequence (PRE) flanked by AAV ITRs, can be constructed by directly inserting the nucleotide sequence encoding the protein of interest and the PRE into an AAV genome which has had the major AAV open reading frames ("ORFs") excised therefrom. Other portions of the AAV genome can also be deleted, as long as a sufficient portion of the ITRs remain to allow for replication and packaging functions. These constructs can be designed using techniques well known in the art. (See, e.g., Lebkowski et al. (1988) *Molec. Cell. Biol.* 8:3988-3996; Vincent et al. (1990) *Vaccines* 90 (Cold Spring Harbor Laboratory Press); Carter (1992) *Current Opinion in Biotechnology* 3:533-539; Muzyczka (1992)

*Current Topics in Microbiol. and Immunol.* 158:97-129; Kotin (1994) *Human Gene Therapy* 5:793-801; Shelling et al. (1994) *Gene Therapy* 1: 165-169; and Zhou et al. (1994) *J. Exp. Med.* 179:1867-1875).

Alternatively, AAV ITRs can be excised from the viral genome or from an AAV vector containing the same and fused 5' and 3' of a selected nucleic acid construct that is present in another vector using standard ligation techniques, such as those described in Sambrook et al, Supra. Several AAV vectors are available from the American Type Culture Collection ("ATCC") under Accession Numbers 53222, 53223, 53224, 53225 and 53226.

In order to produce recombinant AAV particles, an AAV vector can be introduced into a suitable host cell using known techniques, such as by transfection. A number of transfection techniques are generally known in the art. See, e.g., Graham et al. (1973) *Virology,* 52:456, Sambrook et al. (1989) Molecular Cloning, a laboratory manual, Cold Spring Harbor Laboratories, N.Y., Davis et al. (1986) *Basic Methods in Molecular Biology*, Elsevier, and Chu et al. (1981) *Gene* 13:197. Particularly suitable transfection methods include calcium phosphate co-precipitation (Graham et al. (1973) *Virol.* 52:456-467), direct micro-injection into cultured cells (Capecchi (1980) *Cell* 22:479-488), electroporation (Shigekawa et al. (1988) *BioTechniques* 6:742-751), liposome mediated gene transfer (Mannino et al. (1988) *BioTechniques* 6:682-690), lipid-mediated transduction (Felgner et al. (1987) *Proc. Natl. Acad. Sci. USA* 84:7413-7417), and nucleic acid delivery using high-velocity microprojectiles (Klein et al. (1987) *Nature* 327:70-73).

Suitable host cells for producing recombinant AAV particles include, but are not limited to, microorganisms, yeast cells, insect cells, and mammalian cells, that can be, or have been, used as recipients of a exogenous nucleic acid molecule. Thus, a "host cell" as used herein generally refers to a cell which has been transfected with an exogenous nucleic acid molecule. The host cell includes any eukaryotic cell or cell line so long as the cell or cell line is not incompatible with the protein to be expressed, the selection system chosen or the fermentation system employed. Non-limiting examples include CHO dhfr-cells (Urlaub and Chasin (1980) *Proc. Natl. Acad. Sci. USA* 77:4216-4220), 293 cells (Graham et al. (1977) *J. Gen. Virol.* 36: 59) or myeloma cells like SP2 or NS0 (Galfre and Milstein (1981) *Meth. Enzymol.* 73(B):3-46).

In one embodiment, cells from the stable human cell line, 293 (readily available through, e.g., the ATCC under Accession No. ATCC CRL1573) are preferred in the practice of the present invention. Particularly, the human cell line 293, which is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce rAAV virions.

Host cells containing the above-described AAV vectors must be rendered capable of providing AAV helper functions in order to replicate and encapsidate the expression cassette flanked by the AAV ITRs to produce recombinant AAV particles. AAV helper functions are generally AAV-derived coding sequences which can be expressed to provide AAV gene products that, in turn, function in trans for productive AAV replication. AAV helper functions are used herein to complement necessary AAV functions that are missing from the AAV vectors. Thus, AAV helper functions include one, or both of the major AAV open reading frames (ORFs), namely the rep and cap coding regions, or functional homologues thereof.

The AAV rep coding region of the AAV genome encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other exogenous) promoters. The Rep expression products are collectively required for replicating the AAV genome. The AAV cap coding region of the AAV genome encodes the capsid proteins VP1, VP2, and VP3, or functional homologues thereof. AAV helper functions can be introduced into the host cell by transfecting the host cell with an AAV helper construct either prior to, or concurrently with, the transfection of the AAV vector comprising the expression cassette, AAV helper constructs are thus used to provide at least transient expression of AAV rep and/or cap genes to complement missing AAV functions that are necessary for productive AAV infection. AAV helper constructs lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. (See, e.g., Samulski et al. (1989) *J. Virol.* 63:3822-3828; and McCarty et al. (1991) *J. Virol.* 65:2936-2945). A number of other vectors have been described which encode Rep and/or Cap expression products. See, e.g., U.S. Pat. No. 5,139,941.

As a consequence of the infection of the host cell with a helper virus, the AAV Rep and/or Cap proteins are produced. The Rep proteins also serve to duplicate the AAV genome. The expressed Cap proteins assemble into capsids, and the AAV genome is packaged into the capsids. This results the AAV being packaged into recombinant AAV particles comprising the expression cassette. Following recombinant AAV replication, recombinant AAV particles can be purified from the host cell using a variety of conventional purification methods, such as CsCl gradients. The resulting recombinant AAV particles are then ready for use for gene delivery to various cell types.

Alternatively, a vector of the invention is a recombinant AAV pseudotypes wherein the capsids consist of, but are not limited to, combinations of any of the following serotypes: AAV-1 AAV-2, AAV-3, AAV-4, AAV-5, AAV-7, and AAV-8. Such vectors and methods of their production are more completely described in U.S. application Ser. No. 09/804,898, which is hereby incorporated by reference. In a preferred embodiment, the AAV pseudotype is an AAV1/2 pseudotype with a 1:1 ratio of AAV1 and AAV2 VP1,2 and 3 proteins.

Alternatively, a vector of the invention can be a virus other than the adeno-associated virus, or portion thereof, which allows for expression of a nucleic acid molecule introduced into the viral nucleic acid. For example, replication defective retroviruses, adenoviruses, herpes simplex virus, and lentivirus can be used. Protocols for producing recombinant retroviruses and for infecting cells in vitro or in vivo with such viruses can be found in Current Protocols in Molecular Biology, Ausubel et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include Crip, Cre, 2 and Am. The genome of adenovirus can be manipulated such that it encodes and expresses the protein of interest but is inactivated in terms of its ability to replicate in a normal lytic viral life cycle. See e.g., Berkner et al. (1988) *BioTechniques* 6:616; Rosenfeld et al. (1991) *Science* 252: 431-434; and Rosenfeld et al. (1992) *Cell* 68: 143-155. Suitable adenoviral vectors derived from the adenovirus strain Ad type 5 dl324 or other strains of adenovirus (e.g., Ad2, Ad3, Ad7 etc.) are well known to those skilled in the art.

Alternatively, the vector can be delivered using a non-viral delivery system. This includes delivery of the vector to the desired tissues in colloidal dispersion systems that include, for example, macromolecule complexes, nanocapsules, microspheres, beads, and lipid-based systems including oil-in-water emulsions, micelles, mixed micelles, and liposomes.

Liposomes are artificial membrane vesicles which are useful as delivery vehicles in vitro and in vivo. In order for a liposome to be an efficient gene transfer vehicle, the following characteristics should be present: (1) encapsulation of the genetic material at high efficiency while not compromising the biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al. (1988) *Biotechniques*, 6:682). Examples of suitable lipids liposomes production include phosphatidyl compounds, such as phosphatidylglycerol, phosphatidylcholine, phosphatidylserine, phosphatidylethanolamine, sphingolipids, cerebrosides, and gangliosides. Additional examples of lipids include, but are not limited to, polylysine, protamine, sulfate and 3b-[N—(N',N' dimethylaminoethane) carbamoyl]cholesterol.

Alternatively, the vector can be coupled with a carrier for delivery Exemplary and preferred carriers are keyhole limpet hemocyanin (KLH) and human serum albumin. Other carriers may include a variety of lymphokines and adjuvants such as INF, IL-2, IL-4, IL-8 and others. Means for conjugating a peptide to a carrier protein are well known in the art and include glutaraldehyde, m-maleimidobenzoyl-N-hydroxysuccinimide ester, carbodiimyde and bis-biazotized benzidine. The vector can be conjugated to a carrier by genetic engineering techniques that are well known in the art. (See e.g., U.S. Pat. Nos. 4,608,251; 4,601,903; 4,599,231; 4,599,230; 4,596,792; and 4,578,770).

In one embodiment, particle-mediated delivery using a gene-gun can be used as a method to deliver the vector. Suitable particles for gene gun-based delivery of include gold particles. In one embodiment, the vector can be delivered as naked DNA. Gene gun based delivery is described, for example by, Braun et al. (1999) *Virology* 265:46-56; Drew et al. (1999) *Vaccine* 18:692-702; Degano et al. (1999) *Vaccine* 18:623-632; and Robinson (1999) *Int Mol Med* 4:549-555; Lai et al. (1998) *Crit. Rev Immunol.* 18:449-84; See e.g., Accede et al. (1991) *Nature* 332: 815-818; and Wolff et al. (1990) *Science* 247:1465-1468 Murashatsu et al., (1998) *Int. J. Mol. Med.* 1: 55-62; Agracetus et al. (1996) *J. Biotechnol.* 26: 37-42; Johnson et al. (1993) *Genet. Eng.* 15: 225-236). Also within the scope of the invention is the delivery of the vector in one or more combinations of the above delivery methods.

VII. Vector Delivery Systems

Delivery systems include methods of in vitro, in vivo and ex vivo delivery of the vector. For in vivo delivery, the vector can be administered to a subject in a pharmaceutically acceptable carrier. The term "pharmaceutically acceptable carrier", as used herein, refers to any physiologically acceptable carrier for in vivo administration of the vectors of the present invention. Such carriers do not induce an immune response harmful to the individual receiving the composition.

In one embodiment, vector can be distributed throughout a wide region of the CNS, by injecting the vector into the cerebrospinal fluid, e.g., by lumbar puncture (See e.g., Kapadia et al. (1996) *Neurosurg* 10: 585-587).

Alternatively, precise delivery of the vector into specific sites of the brain, can be conducted using stereotactic microinjection techniques. For example, the subject being treated can be placed within a stereotactic frame base (MRI-compatible) and then imaged using high resolution MRI to determine the three-dimensional positioning of the particular region to be treated. The MRI images can then be transferred to a computer having the appropriate stereotactic software, and a number of images are used to determine a target site and trajectory for antibody microinjection. The software translates the trajectory into three-dimensional coordinates that are precisely registered for the stereotactic frame. In the case of intracranial delivery, the skull will be exposed, burr holes will be drilled above the entry site, and the stereotactic apparatus used to position the needle and ensure implantation at a predetermined depth. The vector can be delivered to regions, such as the cells of the spinal cord, brainstem, (medulla, pons, and midbrain), cerebellum, diencephalon (thalamus, hypothalamus), telencephalon (corpus striatum, cerebral cortex, or within the cortex, the occipital, temporal, parietal or frontal lobes), or combinations, thereof. In another preferred embodiment, the vector is delivered using other delivery methods suitable for localized delivery, such as localized permeation of the blood-brain barrier. Particularly preferred delivery methods are those that deliver the vector to regions of the brain that require modification.

Modification as used herein refers to a change in the cellular activity in the region of the brain injected with the vector. The change in cellular activity can result from changing the expression, or production of genes responsible for stimulating a cell. For example, delivery of a vector comprising a nucleotide sequence encoding GAD, to a region of the brain that is overstimulated, such as the basal ganglia. In particular, delivery of the vector to the STN which are overactive in diseases such as Parkinson's, will result in expression of GAD in this region. While not being required to provide a mechanism of action, the expression of GAD in the STN results in production of GABA within the STN cells, the STN cells release GABA locally such that the released GABA binds to GABA-A and GABA-B receptors on the STN cell surface. GABA binding to the GABA receptors results in a reduction in cell stimulation, thereby reducing overactivity in the STN cells and prevent neuronal destruction.

VIII. Pharmaceutical Compositions and Pharmaceutical Administration

Another aspect of the invention provides compositions comprising a polypeptide, or polynucleotide of the invention, a binding molecule that is specific for a Chimeric GAD polypeptide or polynucleotide (e.g., an antibody), an inhibitor of a Chimeric GAD polypeptide or polynucleotide, or other molecule that can increase or decrease the level or activity of a Chimeric GAD polypeptide or polynucleotide marker. Such compositions may be pharmaceutical compositions formulated for use as a therapeutic.

In one embodiment, the invention provides a composition that comprises a Chimeric GAD polypeptide or polynucleotide of the invention, such as those described in SEQ. I.D. NO:1, SEQ. I.D. NO:2, SEQ. I.D. NO:3, or SEQ. I.D. NO:4, or polypeptides having substantial homology with one of the aforementioned Chimeric GAD polypeptides.

Alternatively, the invention provides a composition that comprises a component that is a fragment, modification, precursor or successor of a Chimeric GAD polynucleotide or polypeptide SEQ. I.D. NO:1, SEQ. I.D. NO:2, SEQ. I.D. NO:3, or SEQ. I.D. NO:4 or to a molecule that comprises a foregoing component.

In another embodiment, the invention provides a composition that comprises a polypeptide or polynucleotide that is structurally different from a component specifically identified in SEQ. I.D. NO:1, SEQ. I.D. NO:2, SEQ. I.D. NO:3, or SEQ. I.D. NO:4, but has the same function or properties, or a molecule that comprises a foregoing component.

In another embodiment, the invention provides a composition that comprises a polynucleotide that binds to a Chimeric GAD polypeptide of the invention or a molecule that comprises a foregoing polynucleotide.

In another embodiment, the invention provides a composition that comprises an antibody that specifically binds to a Chimeric GAD polypeptide, or a molecule that comprises a foregoing antibody.

In another embodiment, the invention provides a composition that comprises a modulator of the level or activity of a Chimeric GAD polypeptide (e.g., an inhibitor of a Chimeric GAD polypeptide, an antisense polynucleotide which is complementary to a polynucleotide that encodes a Chimeric GAD polypeptide), or a molecule that comprises a foregoing modulator.

Such compositions may be pharmaceutical compositions. Typically, a pharmaceutical composition comprises a therapeutically effective amount of an active agent and is formulated with a suitable excipient or carrier. The invention also provides pharmaceutical compositions for the treatment of various disorders including neurological disorders. These compositions may include a protein and/or nucleic acid of the invention, and can be formulated as described herein. Alternately, these compositions may include an antibody which specifically binds to a protein of the invention and/or an antisense polynucleotide which is complementary to a polynucleotide of the invention and can be formulated as described herein.

The pharmaceutical compositions of the invention can be prepared in any suitable manner known in the pharmaceutical art. The carrier or excipient may be a solid, semisolid, or liquid material that can serve as a vehicle or medium for the active ingredient. Suitable carriers or excipients are well known in the art and include, but are not limited to saline, buffered saline, dextrose, water, glycerol, ethanol, and combinations thereof. The pharmaceutical compositions may be adapted for oral, inhalation, parenteral, or topical use and may be administered to the patient in the form of tablets, capsules, aerosols, inhalants, suppositories, solutions, suspensions, powders, syrups, and the like. As used herein, the term "pharmaceutical carrier" may encompass one or more excipients. In preparing formulations of the compounds of the invention, care should be taken to ensure bioavailability of an effective amount of the agent. Suitable pharmaceutical carriers and formulation techniques are found in standard texts, such as Remington's Pharmaceutical Sciences, Mack Publishing Co., Easton, Pa.

The vector of the invention can also be incorporated into pharmaceutical compositions suitable for administration to a subject. A pharmaceutical composition may comprise the vector of the invention and a pharmaceutically acceptable vector carrier. As used herein, "pharmaceutically acceptable vector carrier" includes any and all solvents, dispersion media, coatings, antibacterial and antifungal agents, isotonic and absorption delaying agents, and the like that are physiologically compatible. Examples of pharmaceutically acceptable vector carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In one embodiment, the vector is administered by intravenous infusion or injection. In another embodiment, the vector is administered by intramuscular or subcutaneous injection. In another embodiment, the vector is administered perorally. In the most preferred embodiment, the vector is delivered to a specific location using stereotactic delivery.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antigen, antibody or antibody portion) in the required amount in an appropriate solvent with one or a combination of ingredients enumerated above, as required, followed by filtered sterilization.

Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The vector of the present invention can be administered by a variety of methods known in the art. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978. The pharmaceutical compositions of the invention may include a "therapeutically effective amount" or a "prophylactically effective amount" of the vectors of the invention. A "therapeutically effective amount" refers to an amount effective, at dosages and for periods of time necessary, to achieve the desired therapeutic result.

A therapeutically effective amount of the vector may vary according to factors such as the disease state, age, sex, and weight of the individual, and the ability of the vector to elicit a desired response in the individual. A therapeutically effective amount is also one in which any toxic or detrimental effects of the vector are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

IX. Kits

In another aspect, the invention provides a kit for detecting a Chimeric GAD polypeptides or polynucleotides.

The kits of the invention may comprise one or more of the following: an antibody, wherein the antibody specifically binds with a Chimeric GAD polypeptide, a labeled binding partner to the antibody, a solid phase upon which is immobilized the antibody or its binding partner, a polynucleotide probe that can hybridize to a Chimeric GAD polynucleotide, pairs of primers that under appropriate reaction conditions can prime amplification of at least a portion of a Chimeric GAD polynucleotide or a polynucleotide encoding a Chimeric GAD polypeptide (e.g., by PCR), instructions on how to use the kit, and a label or insert indicating regulatory approval for diagnostic or therapeutic use, about 90% homology, about 95% homology, about 99% homology to Chimeric GAD.

EXAMPLES

Example 1

Methods and Materials (i) Construction of Chimeric GAD65/67

Plasmids The plasmids pAM/CBA-GAD65(1-60)GAD67 (66-594)-WPRE-BGH and pAM/CBA-GAD65(1-72) GAD67(79-594)-WPRE-BGH were both constructed from pAM/CBA-GAD65-WPRE-BGH and pAM/CBA-GAD67-WPRE-BGH, which contain DNA sequence corresponding to the open reading frames of human GAD65 and human GAD67, respectively.

Plasmid pAM/CBA-GAD65(1-60)GAD67(66-594)-WPRE-BGH contains a sequence of human glutamate decarboxylase derived from the N-terminal 60 amino acids of GAD65 and amino acids 66 to 594 of GAD67

To construct this plasmid, firstly the N-terminal 65 amino acids were deleted from pAM/CBA-GAD67-WPRE-BGH. The primers GAD67 for 5' aat aat ctc gag tgc ctt cag gga gag 3' (SEQ. ID NO. 11), and GAD67rev 5' ata tat tct gca gtc aac cag gat ctg 3' (SEQ. ID NO. 12), were used to amplify a 330 bp portion of GAD67. This was digested with PstI and Xho I and inserted into pAM/CBA-GAD67-WPRE-BGH also digested with PstI and XhoI, which resulted in the removal of amino acids 1-65 of GAD67.

The primers GAD651-60for 5' aat aat ctc gag atg gca tct ccg gcc tct g 3' (SEQ. ID NO. 13), and GAD651-60rev 5' ata tat act cga gcc gcc gct ctc cgc c 3' (SEQ. ID NO. 14), were used to amplify a 200 bp fragment containing amino acids 1-60 of GAD65. This was digested with Xho I and inserted into the pAM/CBA-GAD67(A1-65)-WPRE-BGH plasmid to create pAM/CBA-GAD65(1-60)GAD67(66-594)-WPRE-BGH. Sequencing of the plasmid revealed no PCR-induced errors.

The amino acid sequence flanking the junction between the two serotypes is as follows:
AESSGGSSAFRERQ. AESSG is derived from GAD65 amino acids 57 to 60. SS is derived partially from the XhoI restriction site (which forms the junction between the two isoforms) and amino acid 65 of GAD67. AFRERQ is derived from GAD67 amino acids 66 to 71.

Plasmid pAM/CBA-GAD65(1-72)GAD67(79-594)-WPRE-BGH contains a sequence of human glutamate decarboxylase derived from the N-terminal 72 amino acids of GAD65 and amino acids 79 to 594 of GAD67.

To construct this plasmid, firstly the N-terminal 78 amino acids were deleted from pAM/CBA-GAD67-WPRE-BGH. The primers GAD67A1-78for 5' aat aat ctc gag tgt gaa aac agc gac cgg ga 3' (SEQ. ID NO. 15), and GAD67A1-78rev 5' ata tat tct gca gtc aac cag gat ctg 3' (SEQ. ID NO. 16), were used to amplify a 295 bp portion of GAD67. This was digested with PstI and Xho I and inserted into pAM/CBA-GAD67-WPRE-BGH also digested with PstI and XhoI, which resulted in the removal of amino acids 1-78 of GAD67.

The primers GAD651-72for 5' aat aat ctc gag atg gca tct ccg gcc tct g 3' (SEQ. ID NO. 17), and GAD651-60rev 5' ata tct cga ggc ggc ctt ccg ggc g 3' (SEQ. ID NO. 18), were used to amplify a 230 bp fragment containing amino acids 1-72 of GAD65. This was digested with Xho I and inserted into the pAM/CBA-GAD67(A1-78)-WPRE-BGH plasmid to create pAM/CBA-GAD65(1-60)GAD67(66-594)-WPRE-BGH. Sequencing of the plasmid revealed one PCR-induced error which was an A to T nucleotide substitution of alanine to thymidine at nt 227. This resulted in an amino acid change from glutamic acid (E) to aspartic acid (D).

The amino acid sequence flanking the junction between the two serotypes is as follows: RKAALECEN. RKAA is derived from GAD65 amino acids 69-72. LE is derived from the XhoI restriction site, which forms the junction between the two isoforms. CDNSDRD is derived from CENSDRD, which are amino acids 79 to 85 of GAD67. A point mutation in the DNA sequence resulted in a substitution of glutamic acid (E) with aspartic acid (D).

(ii) Plasmid Transfection of HEK293 Cells

HEK 293 cells were plated at $5 \times 10^4$ cells/well onto collagen-coated plates, 24 hours prior to transfection. The following day, 1 µg of the appropriate plasmid DNA spiked with 0.1 µg of EGFP plasmid was mixed with 50 µl OptiMEM (Invitrogen) in a sterile tube. Three microlitres of Optifect (Invitrogen) was mixed with 50 µl OptiMEM in a separate tube, then the contents of the tubes were mixed and incubated at room temperature for 30 min. The plasmid/Optifect solution was then added to a well and mixed by gently pipetting up and down.

(iii) GABA Release

Forty-eight hours following transfection, each well of cells was washed 5× with 1 ml of 1× phosphate buffered saline, then incubated in 1 ml artificial CSF (144 mM NaCl, 1.5 mM $CaCl_2$, 1 mM $MgCl_2$, and 5 mM glucose in 10 mM MOPS, pH 7.5) for 10 minutes at 37° C. The supernatant was removed and stored at −80° C.

(iv) Extraction of Cytoplasmic Proteins

200 µl of Mammalian Cell Lysis Reagent (Sigma) was added to each well and incubated at room temperature for 10 mins. The lysates were then transferred to 1.5 ml microfuge tubes and centrifuged at 10,000 g for 10 mins at 4° C. The supernatants were transferred to fresh microfuge tubes and stored at −80° C. for analysis by Western blot.

(v) Western Blot

The amount of protein in each lysate was quantified using the Total Protein Microassay (Biorad) with BSA from 0 to 25 ng/ml as a standard. Three micrograms of each sample were processed for SDS-PAGE and Western Blotting analysis according to the Novex NuPage western blotting protocol (Invitrogen), using a 4-12% Novex Bis-Tris gel and PVDF membrane. The membrane was transferred into 0.1% Ponceau S stain (Sigma) to check that the protein had transferred, and it was cut at the level of the 40 kDa protein standard to allow simultaneous detection of the GAD proteins (65-67 kDa) and the EGFP control (27 kDa).

The membrane was blocked by incubating in 5% skim milk powder in TBST on a shaker overnight at 4° C. then was washed three times with TBST (5 minutes per washing) prior to addition of the anti-GAD65/67 antibody (1:2000, AB1511 Chemicon) to the top half of the membrane, and the anti-GFP antibody (1:2000, A290, Abcam) to the bottom half of the membrane. Both antibodies were diluted in 1% milk powder/TBST. Following an overnight incubation, the membranes were washed three times with TBST (5 minutes per washing) then incubated at room temperature for one hour in goat anti-rabbit secondary antibody (1:30000, Sigma A6158) diluted in 1% milk powder/TBST. The membranes were washed three times with TBST (5 minutes per washing) prior to detection using the ECL Plus detection kit (Amersham Biosciences) according to the manufacturer's instructions. The membrane was exposed against Xray film (Kodak) for two minutes, then developed.

(vi) HPLC.

The samples were thawed and filtered (4 mm 0.22 µm syringe filter unit; millipore) and δ-aminovaleric acid (2 nmol/l stock; ICN) was added as an internal standard (2 µl to 98 µl of sample; or 2 µl to 96 µl of aCSF plus 2 µl of 20 pmol/µl GABA standard; Sigma). One hundred microliters of sample was derivatized with an equal volume of o-parathaldialdehyde (Sigma). The derivatized sample was then injected (10 µl) into a Premium reversed phase C18 5-mm column (250× 4.6 mm i.d.; Shimadzu). GABA was eluted using a two-solvent gradient with 0.1M potassium acetate (pH 5.7) and methanol over 20 minutes. The elution gradient (in percent methanol) was as follows: 4 minutes isocratic at 55%, 2 minutes linear to 70%, 2 minutes isocratic at 70%, followed by 1 minute linear to 100%, 1 minute linear at 100%, and then step to 55% for 10 minutes to reequilibrate the column, at a constant flow rate of 1.0 ml/minute. Derivatized GABA was detected by fluorescence (Shimadzu RF-10Ax1) with excitation at 233 nm and emission at 450. The GABA peak was identified by comparison to the standard (GABA, Sigma) and internal standard (δ-aminovaleric acid).

Example 2

Vectors and Delivery Systems

This series of prophetic examples describes methods of construction and use of various adeno-associated virus delivery systems for Chimeric GAD i) Vector Construction This example describes a method for construction of an adeno-associated virus vector with a Chimeric GAD cDNA. Chimeric GAD can be subcloned into an AAV plasmid under the control of a 1.8 kb rat NSE (neuron specific enolase) promoter (Foress-petter et al. (1986) *J. Neurosci. Res.* 16, 141-156 (1998)) 5' of the GAD cDNA followed by the Woodchuck Hepatitis Post-Transcriptional Regulatory Element (WPRE) and a bovine growth hormone (BGH) polyadenylation site between the AAV inverted terminal repeats, as previously described (During et al. (1998) *Nature Med.* 4:1131-1135).

Plasmids can be packaged to generate high titer rAAV-Chimeric GAD viral particles using an optimized protocol based on the original helper-free transient transfection method described by Samulski et al. (1989) *J. Virol.* 63:3822-3828), but modified by using an improved 4th generation helper plasmid, pDG as described by Grimm et al. (1999) *Hum Gene Ther* 10, 2445-2450. The helper plasmid would contain both the rep and cap open reading frames, as well the minimal set of adenoviral genes necessary for helper functions. The vectors can generated using calcium phosphate transfection of both plasmids into 293 cells. Vector stocks can be purified using ammonium sulfate followed by double cesium banding. The bands containing the viral particle can then be isolated from the cesium chloride preparation and dialysis into suitable buffer.

Particle titers can be determined using an ELISA assay kit available (Progen, Inc.) which uses an A20 monoclonal antibody that recognizes intact particles. Purification of the viral particles can be performed as described by Clark et al., (1999) *Hum. Gene. Ther.* 10: 1031-1039 and Zolutkhin et al. (1999) *Gene Therapy* 9: 973-985.

(ii) Packaging Protocol

To package the recombinant vectors, human embryonic kidney cells, 293 cells (from American Type Culture Collection (ATCC # CRL-1573)), passage 4-12 can be used. The 293 kidney cells ($1.5 \times 10^7$ cells) can be seeded into forty 15 cm dishes in complete DMEM (Gibco) containing 10% fetal bovine serum (Hyclone), 0.1 mM MEM non-essential amino acids solution (Gibco), 1 mM MEM sodium pyruvate (Gibco), 0.05% Penicillin-Streptomycin (5,000 units/ml, Gibco), and incubated overnight at 37° C. When the cells are 70% confluent and 2-3 hours prior to transfection, the cells should be fed fresh Iscove modified Dulbecco medium (IMDM, Gibco) containing 10% fetal bovine serum (Hyclone) without antibiotics.

Plasmids can be isolated from the cells by the alkaline lysis method (Sambrook et al, supra), and were further purified by HPLC (BioCAD, Sprint, PerSeptive Biosystems), and concentrated with 2 volumes of 100% ethanol (AR grade, BDH).

All HPLC elute buffers (Buffer A: 250 mM TrisHCl, 10 mM EDTA, pH 8.0; Buffer B: 25 mM TrisHCl, 1 mM EDTA, 2M NaCl, pH, 8.0; Buffer C: Milli Q water) used for purification should be autoclaved and filter sterilized prior to use. For each 15 cm tissue culture plate, a total of 60 µg of plasmid DNA should be dissolved in 3.0 ml of 0.25M $CaCl_2$ and then quickly mixed with 3.0 ml of HEPES-buffered saline (50 mM HEPES, 280 mM NaCl, 1.5 mM $Na_2HPO_4$ [pH 7.05-7.10]), incubated for 2 min and then added to the cells. 6-8 hours after transfection, the medium is to be aspirated and cells washed with IMDM supplemented with 10% fetal bovine serum without antibiotics. The washing medium is to then aspirated and replaced with fresh IMDM (Gibco) containing 10% fetal bovine serum with trace pen/strep. The cells are to be harvested at 48 hours after transfection. After low-speed centrifugation on a tabletop centrifuge, the cell pellets are resuspended in 20 ml of Opti-MEM (Gibco) and subjected to sonication using 15-20% energy for 50 bursts lasting 1 min. Cell debris is removed with low speed centrifugation. The clarified supernatant is collected into a 50 ml polypropylene tube, the cell pellets are resuspended in 20 ml of Opti-MEM for reextraction. The supernatants are then combined.

One-third volume of ice-cold saturated $(NH_4)_2SO_4$ is added to the supernatant, mixed and placed on ice for 10 minutes. The sample is then centrifuged at 8,000 rpm at 4° C. for 10 min, supernatant is transferred to a polypropylene centrifuge tube, ⅔volume of the initial lysate of saturated $(NH_4)_2SO_4$ is added and mixed well, then placed on ice for 20 min prior to centrifugation at 12,000 rpm for 20 min at 4° C. The pellet is redissolved in CsCl-phosphate-buffered saline (PBS) (pH 7.4) solution (density 1.37 g/l) and centrifuged in an SW41 rotor Beckman at 80,000 rpm (for 24 hours with a 0.5 ml CsCl-PBS cushion (density, 1.5 g/ml).

The band containing recombinant AAV particle (rAAV) is collected and re-centrifuged as described above for a further 24 hours. Finally, the rAAV band is collected following the second CsCl centrifugation and dialyzed against one liter sterile dialysis buffer containing 50 mM NaCl, 5 mM Tris-HCl and 0.5 mM $MgCl_2$ (pH 7.4) for an initial 4 hours. Dialysis is repeated using one liter of fresh cold sterile dialysis buffer for another 4 hours and finally overnight dialysis using a 50,000 molecular weight cut off dialysis membrane (Spectrapor) and fresh sterile dialysis buffer. The AAV virus particle titer can determined using an ELISA method described by Wistuba et al. ((1997) *J. Virol.* 71: 1341-1352). Briefly, a monoclonal antibody specific for AAV assembled capsids is coated onto microtiter strips and is used to capture AAV particles. A biotin-conjugated monoclonal antibody to AAV is bound to the immune complex, streptavidin peroxidase conjugate reacts with the biotin molecules. Addition of substrate solution results in a color reaction which is proportional to specifically bound virus particles, and allows the quantitative determination of an unknown particle titer.

Viral particle titre can also determined by the AAV titration ELISA kit provided by Progen (Germany). One hundred microliter of ready-to-use wash buffer, positive, negative controls, and dilutions of standard and samples are pipetted into appropriate wells of the microtiter strips which were sealed with adhesion foil. After incubation for 1 hour at 37° C., the solution is removed and each well is rinsed 3 times with 200 µl of washing buffer for 30 seconds. The washing buffer is removed and 100 µl of ready to use biotin conjugate is added. The strips are sealed with adhesion foil and incubated for one hour at 37° C. The strips are washed as described above. A volume of 100 µl of ready-to-use streptavidin conjugate is added, and the strips are sealed with adhesion foil and incubated for one hour at 37° C. The washing steps are then repeated as described above. Substrate at a volume of 100 µl are pipetted into each well and incubated at room temperature for 10 min. The reaction is stopped by adding 100 µl of stop solution into each well. Absorbance of each well can be measured photometrically at 450 nm wavelength.

(iii) Transduction of Neurons

Target cells for vectors of the invention include, among other, the intrinsic neurons of the subthalamic nucleus (STN). The vector of the invention can be administered at a dose of $3.5\times10^9$ virions in a volume of 35 microliters (based on genomic titer of rAAV stocks of $10^{11}$/ml) with an additional 15 µl of USP 25% mannitol as a flush. Based on the extensive analysis of vector distribution using AAV in the rodent brain, it has been shown that if rAAV is delivered at low infusion rates (<1.0 µl/min), the best transduction levels were obtained. Moreover the vector is delivered with high efficiency to cells immediately surrounding the injection tract, with an exponential fall off in gene expression extending from the tip of the injection cannula. Using volumes of 3 microliters delivering ~$5\times10^9$ virions, 80% of transduced cells lie within 1 mm of the injection site with less than 5% of transduced cells lying greater than 2 mm from the injection site. In the study using a 35 µl volume of vector (12 fold greater volume) but a titer approximately 15-20 fold lower (i.e. roughly equivalent number of vector genomes delivered), gene expression was restricted to a volume of several millimeters. This would confine the vector to the STN whose dimensions are approximately 4.8 mm×5 mm×6 mm or ~140 mm. Similar techniques can be used to confine the virion to any specified region.

(iv) Efficiency of Transduction

Transduction efficiencies can reach 100% in permissive cell-lines and permissive target cells in vivo if sufficient MOI are used. Based on rodent data it is expected that an injection volume of 35 microliters into a human STN with the absolute number of virion genomic particles of ~$3.5\times10^9$ is likely to transduce from 70-175,000 cells. This represents approximately 25-60% of target cells transduced.

Those skilled in the art will recognize, or be able to ascertain using no more than routine experimentation, many equivalents to the specific embodiments of the invention described herein. Such equivalents are intended to be encompassed by the following claims.

REFERENCES

Asada et al., 1996. Mice lacking the 65 kDA isoform of glutamic acid decarboxylase (GAD65) maintain normal levels of GAD67 and GABA in their brains but are susceptible to seizures. BBRC 229, 891-895.

Asada et al., 1997. Cleft palate and decreased brain gamma-aminobutyric acid in mice lacking the 67-kDa isoform of glutamic acid decarboxylase. PNAS 94, 6469-6499.

Erlander M G et al., 1991 Two genes encode distinct glutamate decarboxylases. Neuron 7, 91-100.

Bu D-F et al., 1992. Two human glutamate decarboxylases, 65-kDa GAD and 67-kDa GAD are each encoded by a single gene. PNAS 89, 2115-2119.

Dirkx R et al., 1995. Targeting of the 67-kDa isoform of glutamic acid decarboxylase to intracellular organelles is mediated by its interaction with the $NH_2$-terminal region of the 64-kDa isoform of glutamic acid decarboxylase. J Biol Chem 270, 2241-2246.

Esclapez M et al., 1994. Comparative localization of two forms of glutamic acid decarboxylase and their mRNAs in rat brain supports the concept of functional differences between the forms. J Neurosci 14, 1834-1855.

Kanaani et al., 1999. The hydrophilic isoform of glutamate decarboxylase, GAD67, is targeted to membranes and nerve terminals independent of dimerization with the hydrophobic membrane anchored isoform, GAD65. J Biol Chem 274, 37200-37209.

Kanaani et al., 2002. A combination of three distinct trafficking signals mediates axonal targeting and presynaptic clustering of GAD65. J. Cell Biol. 158, 1229-1238.

Kash S F et al., 1997. Epilepsy in mice deficient in the 65-kDa isoform of glutamic acid decarboxylase. PNAS 94, 14060-14065.

Namchuk M et al., 1997. Phosphorylation of serine residues 3, 6, 10 and 13 distinguishes membrane anchored from soluble glutamic acid decarboxylase 65 and is restricted to glutamic acid decarboxylase65alpha. J. Biol Chem 272, 1548-1557.

Sheikh SN and Martin DL. 1996. Heteromers of glutamate decarboxylase isoforms occur in rat cerebellum. J Neurochem 66, 2082-2090.

Stork, O et al., 2000. Postnatal development of a GABA deficit and disturbance of neural functions in mice lacking GAD65. Brain Res 865, 45-58.

What is claimed is:

1. A chimeric nucleic acid comprising a nucleic acid sequence encoding a polypeptide with glutamic acid decarboxylase (GAD) activity having an amino-terminal portion of GAD65 and a carboxy-terminal portion of GAD67, wherein the polypeptide has a 99% or more homology with SEQ ID NO: 4.

2. A chimeric nucleic acid comprising a nucleic acid sequence encoding a polypeptide with glutamic acid decarboxylase (GAD) activity having an amino-terminal portion of GAD65 and a carboxy-terminal portion of GAD67, wherein the nucleic acid sequence has a 95% or more identity with SEQ ID NO: 3.

3. The chimeric nucleic acid of claim 2, wherein the nucleic acid sequence has a 99% or more identity with SEQ ID NO: 3.

4. The chimeric nucleic acid of claim 1, wherein the encoded GAD polypeptide comprises the amino acid sequence of SEQ. ID NO: 4.

5. A vector comprising the chimeric nucleic acid sequence of claim 1.

6. A vector, comprising the chimeric nucleic acid sequence of claim 1.

7. The vector of claim 5, wherein the vector is a viral vector selected from the group consisting of adenovirus vectors, adeno-associated virus vectors, herpes virus vectors, parvovirus vectors, and lentivirus vectors.

8. A medicament comprising the chimeric nucleic acid according to claim 1, or the vector according to claim 5.

9. A pharmaceutical composition comprising:
the chimeric nucleic acid according to claim 1, or the vector according to claim 5; and
a pharmaceutically or veterinary acceptable carrier or diluent.

10. A method of altering expression of glutamic acid decarboxylase (GAD) in a region of the central nervous system (CNS) of a subject with a neurodegenerative disease comprising:
identifying a target site in the CNS that requires modification;
delivering the chimeric nucleic acid of claim 1 to the target site in the CNS; and
expressing a polypeptide encoded by said chimeric nucleic acid in the target site, thereby altering GAD expression in the region of the CNS.

11. The method of claim 10, wherein the target site in the central nervous system is a region of a brain.

12. The method of claim 11, wherein the region of the brain is selected from the group consisting of basal ganglia, subthalamic nucleus (STN), pedunculopontine nucleus (PPN), substantia nigra (SN), thalamus, hippocampus, amygdala, hypothalamus, cortex, and combinations thereof.

13. The method of claim 10, wherein the neurodegenerative disease is selected from the group consisting of Parkinson's disease, Alzheimer's disease, senile dementia, Amyloid Lateral Schlerosis (ALS), and epilepsy.

14. The method of claim 10, wherein the step of delivering the chimeric nucleic acid comprises administering the pharmaceutical composition of claim 9.

15. The method of claim 10, wherein step of expressing the polypeptide comprises treating the neurodegenerative disease in the subject by altering GAD expression in the region of the CNS to improve the neurodegenerative disease.

16. A method of altering expression of glutamic acid decarboxylase (GAD) in a region of the central nervous system (CNS) of a subject with a neurodegenerative disease comprising:
identifying a target site in the CNS that requires modification;
delivering the chimeric nucleic acid of claim 2 to the target site in the CNS; and
expressing a polypeptide encoded by said chimeric nucleic acid in the target site, thereby altering GAD expression in the region of the CNS.

17. The method of claim 16, wherein the target site in the central nervous system is a region of a brain.

18. The method of claim 17, wherein the region of the brain is selected from the group consisting of basal ganglia, subthalamic nucleus (STN), pedunculopontine nucleus (PPN), substantia nigra (SN), thalamus, hippocampus, amygdala, hypothalamus, cortex, and combinations thereof.

19. The method of claim 16, wherein the neurodegenerative disease is selected from the group consisting of Parkinson's disease, Alzheimer's disease, senile dementia, Amyloid Lateral Schlerosis (ALS), and epilepsy.

20. The method of claim 16, wherein step of expressing the polypeptide comprises treating the neurodegenerative disease in the subject by altering GAD expression in the region of the CNS to improve the neurodegenerative disease.

21. The vector of claim 6, wherein the vector is a viral vector selected from the group consisting of adenovirus vectors, adeno-associated virus vectors, herpes virus vectors, parvovirus vectors, and lentivirus vectors.

22. A medicament comprising the chimeric nucleic acid according to claim 2, or the vector according to claim 6.

23. A pharmaceutical composition comprising:
the chimeric nucleic acid according to claim 2, or the vector according to claim 6; and
a pharmaceutically or veterinary acceptable carrier or diluent.

* * * * *

```
                            SEQUENCE LISTING

<160> NUMBER OF SEQ ID NOS: 18

<210> SEQ ID NO 1
<211> LENGTH: 1776
<212> TYPE: DNA
<213> ORGANISM: Artificial
<220> FEATURE:
<223> OTHER INFORMATION: chimeric nucleic acid construct of GAD65 and
      GAD67

<400> SEQUENCE: 1
atggcatctc cgggctctgg cttttggtct ttcgggtcgg aagatggctc tggggattcc      60
gagaatcccg gcacagcgcg agcctggtgc caagtggctc agaagttcac gggcggcatc     120
ggaaacaaac tgtgcgccct gctctacgga gacgccgaga agccggcgga gagcggcggc     180
tcgagtgcct tcagggagag gcaatcctcc aagaacctgc tttcctgtga aaacagcgac     240
cgggatgccc gcttccggcg cacagagact gacttctcta atctgtttgc tagagatctg     300
cttccggcta agaacggtga ggagcaaacc gtgcaattcc tcctggaagt ggtggacata     360
ctcctcaact atgtccgcaa gacatttgat cgctccacca aggtgctgga ctttcatcac     420
ccacaccagt tgctggaagg catggagggc ttcaacttgg agctctctga ccaccccgag     480
tccctggagc agatcctggt tgactgcaga gacaccttga agtatgggt tcgcacaggt      540 catcctcgat ttttcaacca gctctccact ggattggata ttattggcct agctggagaa     600
tggctgacat caacggccaa taccaacatg tttacatatg aaattgcacc agtgtttgtc     660
ctcatggaac aaataacact taagaagatg agagagatag ttggatggtc aagtaaagat     720
ggtgatggga tattttctcc tggggcgcc atatccaaca tgtacagcat catggctgct      780
cgctacaagt acttcccgga agttaagaca aagggcatgg cggctgtgcc taaactggtc     840
ctcttcacct cagaacagag tcactattcc ataaagaaag ctggggctgc acttggcttt     900
ggaactgaca atgtgatttt gataaagtgc aatgaaaggg ggaaaataat tccagctgat     960
tttgaggcaa aaattcttga agccaaacag aagggatatg ttccctttta tgtcaatgca    1020
actgctggca cgactgttta tggagctttt gatccgatac aagagattgc agatatatgt    1080
gagaaatata acctttggtt gcatgtcgat gctgcctggg gaggtgggct gctcatgtcc    1140
aggaagcacc gccataaact caacggcata gaaagggcca actcagtcac ctggaaccct    1200
cacaagatga tgggcgtgct gttgcagtgc tctgccattc tcgtcaagga aaagggtata    1260
ctccaaggat gcaaccagat gtgtgcagga tatctcttcc agccagacaa gcagtatgat    1320
gtctcctacg acaccgggga caaggcaatt cagtgtggcc gccacgtgga tatcttcaag    1380
ttctggctga tgtggaaagc aaagggcaca gtgggatttg aaaaccagat caacaaatgc    1440
ctggaactgg ctgaatacct ctatgccaag attaaaaaca gagaagaatt tgagatggtt    1500
```

```
ttcaatggcg agcctgagca cacaaacgtc tgtttttggt atattccaca aagcctcagg    1560
ggtgtgccag acagccctca acgacgggaa aagctacaca aggtggctcc aaaaatcaaa    1620
gccctgatga tggagtcagg tacgaccatg gttggctacc agccccaagg ggacaaggcc    1680
aacttcttcc ggatggtcat ctccaaccca gccgctaccc agtctgacat tgacttcctc    1740
attgaggaga tagaaagact gggccaggat ctgtaa                              1776
```

<210> SEQ ID NO 2
<211> LENGTH: 591
<212> TYPE: PRT
<213> ORGANISM: Artificial
<220> FEATURE:
<223> OTHER INFORMATION: chimeric amino acid construct of GAD65 and
      GAD67

<400> SEQUENCE: 2

```
Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ala Glu Lys Pro Ala Glu Ser Gly Gly Ser Ser Ala Phe
    50                  55                  60

Arg Glu Arg Gln Ser Ser Lys Asn Leu Leu Ser Cys Glu Asn Ser Asp
65                  70                  75                  80

Arg Asp Ala Arg Phe Arg Arg Thr Glu Thr Asp Phe Ser Asn Leu Phe
                85                  90                  95

Ala Arg Asp Leu Leu Pro Ala Lys Asn Gly Glu Glu Gln Thr Val Gln
            100                 105                 110

Phe Leu Leu Glu Val Val Asp Ile Leu Leu Asn Tyr Val Arg Lys Thr
        115                 120                 125

Phe Asp Arg Ser Thr Lys Val Leu Asp Phe His His Pro His Gln Leu
    130                 135                 140

Leu Glu Gly Met Glu Gly Phe Asn Leu Glu Leu Ser Asp His Pro Glu
145                 150                 155                 160

Ser Leu Glu Gln Ile Leu Val Asp Cys Arg Asp Thr Leu Lys Tyr Gly
                165                 170                 175

Val Arg Thr Gly His Pro Arg Phe Phe Asn Gln Leu Ser Thr Gly Leu
            180                 185                 190

Asp Ile Ile Gly Leu Ala Gly Glu Trp Leu Thr Ser Thr Ala Asn Thr
        195                 200                 205

Asn Met Phe Thr Tyr Glu Ile Ala Pro Val Phe Val Leu Met Glu Gln
    210                 215                 220

Ile Thr Leu Lys Lys Met Arg Glu Ile Val Gly Trp Ser Ser Lys Asp
225                 230                 235                 240

Gly Asp Gly Ile Phe Ser Pro Gly Gly Ala Ile Ser Asn Met Tyr Ser
                245                 250                 255

Ile Met Ala Ala Arg Tyr Lys Tyr Phe Pro Glu Val Lys Thr Lys Gly
            260                 265                 270

Met Ala Ala Val Pro Lys Leu Val Leu Phe Thr Ser Glu Gln Ser His
        275                 280                 285

Tyr Ser Ile Lys Lys Ala Gly Ala Ala Leu Gly Phe Gly Thr Asp Asn
    290                 295                 300

Val Ile Leu Ile Lys Cys Asn Glu Arg Gly Lys Ile Ile Pro Ala Asp
305                 310                 315                 320
```

Phe Glu Ala Lys Ile Leu Glu Ala Lys Gln Lys Gly Tyr Val Pro Phe
                325                 330                 335

Tyr Val Asn Ala Thr Ala Gly Thr Thr Val Tyr Gly Ala Phe Asp Pro
            340                 345                 350

Ile Gln Glu Ile Ala Asp Ile Cys Glu Lys Tyr Asn Leu Trp Leu His
        355                 360                 365

Val Asp Ala Ala Trp Gly Gly Gly Leu Leu Met Ser Arg Lys His Arg
    370                 375                 380

His Lys Leu Asn Gly Ile Glu Arg Ala Asn Ser Val Thr Trp Asn Pro
385                 390                 395                 400

His Lys Met Met Gly Val Leu Leu Gln Cys Ser Ala Ile Leu Val Lys
                405                 410                 415

Glu Lys Gly Ile Leu Gln Gly Cys Asn Gln Met Cys Ala Gly Tyr Leu
            420                 425                 430

Phe Gln Pro Asp Lys Gln Tyr Asp Val Ser Tyr Asp Thr Gly Asp Lys
        435                 440                 445

Ala Ile Gln Cys Gly Arg His Val Asp Ile Phe Lys Phe Trp Leu Met
    450                 455                 460

Trp Lys Ala Lys Gly Thr Val Gly Phe Glu Asn Gln Ile Asn Lys Cys
465                 470                 475                 480

Leu Glu Leu Ala Glu Tyr Leu Tyr Ala Lys Ile Lys Asn Arg Glu Glu
                485                 490                 495

Phe Glu Met Val Phe Asn Gly Glu Pro Glu His Thr Asn Val Cys Phe
            500                 505                 510

Trp Tyr Ile Pro Gln Ser Leu Arg Gly Val Pro Asp Ser Pro Gln Arg
        515                 520                 525

Arg Glu Lys Leu His Lys Val Ala Pro Lys Ile Lys Ala Leu Met Met
    530                 535                 540

Glu Ser Gly Thr Thr Met Val Gly Tyr Gln Pro Gln Gly Asp Lys Ala
545                 550                 555                 560

Asn Phe Phe Arg Met Val Ile Ser Asn Pro Ala Ala Thr Gln Ser Asp
                565                 570                 575

Ile Asp Phe Leu Ile Glu Glu Ile Glu Arg Leu Gly Gln Asp Leu
            580                 585                 590

<210> SEQ ID NO 3
<211> LENGTH: 1773
<212> TYPE: DNA
<213> ORGANISM: Artificial
<220> FEATURE:
<223> OTHER INFORMATION: chimeric nucleic acid construct of GAD65 and
      GAD67

<400> SEQUENCE: 3
atggcatctc cgggctctgg cttttggtct ttcgggtcgg aagatggctc tggggattcc      60
gagaatcccg gcacagcgcg agcctggtgc caagtggctc agaagttcac gggcggcatc     120
ggaaacaaac tgtgcgccct gctctacgga gacgccgaga gccggcggga gagcggcggg     180
agccaacccc gcgggccgc cgcccggaag gccgccctcg agtgtgataa cagcgaccgg     240
gatgcccgct ccggcgcac agagactgac ttctctaatc tgtttgctag agatctgctt     300
ccggctaaga cggtgagga gcaaaccgtg caattcctcc tggaagtggt ggacatactc     360
ctcaactatg tccgcaagac atttgatcgc tccaccaagg tgctggactt tcatcaccca     420
caccagttgc tggaaggcat ggagggcttc aacttggagc tctctgacca ccccgagtcc     480
ctggagcaga tcctggttga ctgcagagac accttgaagt atggggttcg cacaggtcat     540

```
cctcgatttt tcaaccagct ctccactgga ttggatatta ttggcctagc tggagaatgg    600
ctgacatcaa cggccaatac caacatgttt acatatgaaa ttgcaccagt gtttgtcctc    660
atggaacaaa taacacttaa gaagatgaga gagatagttg atggtcaagt aaagatggt     720
gatgggatat tttctcctgg ggcgccata tccaacatgt acagcatcat ggctgctcgc    780
tacaagtact ccccggaagt taagacaaag ggcatggcgg ctgtgcctaa actggtcctc    840
ttcacctcag aacagagtca ctattccata agaaagctg gggctgcact tggctttgga    900
actgacaatg tgattttgat aaagtgcaat gaaggggga aaataattcc agctgatttt    960
gaggcaaaaa ttcttgaagc caaacagaag ggatatgttc ccttttatgt caatgcaact   1020
gctggcacga ctgtttatgg agcttttgat ccgatacaag agattgcaga tatatgtgag   1080
aaatataacc tttggttgca tgtcgatgct gcctggggag gtgggctgct catgtccagg   1140
aagcaccgcc ataaactcaa cggcatagaa agggccaact cagtcacctg gaaccctcac   1200
aagatgatgg gcgtgctgtt gcagtgctct gccattctcg tcaaggaaaa gggtatactc   1260
caaggatgca accagatgtg tgcaggatat ctcttccagc agacaagca gtatgatgtc   1320
tcctacgaca ccggggacaa ggcaattcag tgtggccgcc acgtggatat cttcaagttc   1380
tggctgatgt ggaaagcaaa gggcacagtg ggatttgaaa accagatcaa caaatgcctg   1440
gaactggctg aatacctcta tgccaagatt aaaaacagag aagaatttga gatggttttc   1500
aatggcgagc tgagcacac aaacgtctgt ttttggtata ttccacaaag cctcaggggt   1560
gtgccagaca gccctcaacg acgggaaaag ctacacaagg tggctccaaa aatcaaagcc   1620
ctgatgatgg agtcaggtac gaccatggtt ggctaccagc cccaaggga caaggccaac   1680
ttcttccgga tggtcatctc caacccagcc gctacccagt ctgacattga cttcctcatt   1740
gaggagatag aaagactggg ccaggatctg taa                                1773
```

<210> SEQ ID NO 4
<211> LENGTH: 590
<212> TYPE: PRT
<213> ORGANISM: Artificial
<220> FEATURE:
<223> OTHER INFORMATION: chimeric amino acid construct of GAD65 and
      GAD67

<400> SEQUENCE: 4

```
Met Ala Ser Pro Gly Ser Gly Phe Trp Ser Phe Gly Ser Glu Asp Gly
1               5                   10                  15
Ser Gly Asp Ser Glu Asn Pro Gly Thr Ala Arg Ala Trp Cys Gln Val
            20                  25                  30
Ala Gln Lys Phe Thr Gly Gly Ile Gly Asn Lys Leu Cys Ala Leu Leu
        35                  40                  45
Tyr Gly Asp Ala Glu Lys Pro Ala Glu Ser Gly Gly Ser Gln Pro Pro
    50                  55                  60
Arg Ala Ala Ala Arg Lys Ala Ala Leu Glu Cys Asp Asn Ser Asp Arg
65                  70                  75                  80
Asp Ala Arg Phe Arg Arg Thr Glu Thr Asp Phe Ser Asn Leu Phe Ala
                85                  90                  95
Arg Asp Leu Leu Pro Ala Lys Asn Gly Glu Glu Gln Thr Val Gln Phe
            100                 105                 110
Leu Leu Glu Val Val Asp Ile Leu Leu Asn Tyr Val Arg Lys Thr Phe
        115                 120                 125
Asp Arg Ser Thr Lys Val Leu Asp Phe His His Pro His Gln Leu Leu
    130                 135                 140
```

```
Glu Gly Met Glu Gly Phe Asn Leu Glu Leu Ser Asp His Pro Glu Ser
145                 150                 155                 160

Leu Glu Gln Ile Leu Val Asp Cys Arg Asp Thr Leu Lys Tyr Gly Val
            165                 170                 175

Arg Thr Gly His Pro Arg Phe Phe Asn Gln Leu Ser Thr Gly Leu Asp
        180                 185                 190

Ile Ile Gly Leu Ala Gly Glu Trp Leu Thr Ser Thr Ala Asn Thr Asn
    195                 200                 205

Met Phe Thr Tyr Glu Ile Ala Pro Val Phe Val Leu Met Glu Gln Ile
210                 215                 220

Thr Leu Lys Lys Met Arg Glu Ile Val Gly Trp Ser Ser Lys Asp Gly
225                 230                 235                 240

Asp Gly Ile Phe Ser Pro Gly Ala Ile Ser Asn Met Tyr Ser Ile
            245                 250                 255

Met Ala Ala Arg Tyr Lys Tyr Phe Pro Glu Val Lys Thr Lys Gly Met
            260                 265                 270

Ala Ala Val Pro Lys Leu Val Leu Phe Thr Ser Glu Gln Ser His Tyr
        275                 280                 285

Ser Ile Lys Lys Ala Gly Ala Leu Gly Phe Gly Thr Asp Asn Val
290                 295                 300

Ile Leu Ile Lys Cys Asn Glu Arg Gly Lys Ile Ile Pro Ala Asp Phe
305                 310                 315                 320

Glu Ala Lys Ile Leu Glu Ala Lys Gln Lys Gly Tyr Val Pro Phe Tyr
            325                 330                 335

Val Asn Ala Thr Ala Gly Thr Thr Val Tyr Gly Ala Phe Asp Pro Ile
            340                 345                 350

Gln Glu Ile Ala Asp Ile Cys Glu Lys Tyr Asn Leu Trp Leu His Val
        355                 360                 365

Asp Ala Ala Trp Gly Gly Gly Leu Leu Met Ser Arg Lys His Arg His
    370                 375                 380

Lys Leu Asn Gly Ile Glu Arg Ala Asn Ser Val Thr Trp Asn Pro His
385                 390                 395                 400

Lys Met Met Gly Val Leu Leu Gln Cys Ser Ala Ile Leu Val Lys Glu
            405                 410                 415

Lys Gly Ile Leu Gln Gly Cys Asn Gln Met Cys Ala Gly Tyr Leu Phe
        420                 425                 430

Gln Pro Asp Lys Gln Tyr Asp Val Ser Tyr Asp Thr Gly Asp Lys Ala
    435                 440                 445

Ile Gln Cys Gly Arg His Val Asp Ile Phe Lys Phe Trp Leu Met Trp
450                 455                 460

Lys Ala Lys Gly Thr Val Gly Phe Glu Asn Gln Ile Asn Lys Cys Leu
465                 470                 475                 480

Glu Leu Ala Glu Tyr Leu Tyr Ala Lys Ile Lys Asn Arg Glu Glu Phe
            485                 490                 495

Glu Met Val Phe Asn Gly Glu Pro Glu His Thr Asn Val Cys Phe Trp
            500                 505                 510

Tyr Ile Pro Gln Ser Leu Arg Gly Val Pro Asp Ser Pro Gln Arg Arg
        515                 520                 525

Glu Lys Leu His Lys Val Ala Pro Lys Ile Lys Ala Leu Met Met Glu
        530                 535                 540

Ser Gly Thr Thr Met Val Gly Tyr Gln Pro Gln Gly Asp Lys Ala Asn
545                 550                 555                 560

Phe Phe Arg Met Val Ile Ser Asn Pro Ala Ala Thr Gln Ser Asp Ile
```

```
                            565                 570                 575
Asp Phe Leu Ile Glu Glu Ile Glu Arg Leu Gly Gln Asp Leu
            580                 585                 590

<210> SEQ ID NO 5
<211> LENGTH: 1758
<212> TYPE: DNA
<213> ORGANISM: Homo sapiens

<400> SEQUENCE: 5
atggcatctc cgggctctgg cttttggtct ttcgggtcgg aagatggctc tggggattcc      60
gagaatcccg gcacagcgcg agcctggtgc aagtggctc agaagttcac gggcggcatc     120
ggaaacaaac tgtgcgccct gctctacgga cgccgaga agccggcgga gagcggcggg      180
agccaacccc cgcgggccgc cgcccggaag gccgcctgcg cctgcgacca gaagccctgc     240
agctgctcca agtggatgt caactacgcg tttctccatg caacagacct gctgccggcg     300
tgtgatggag aaaggcccac tttggcgttt ctgcaagatg ttatgaacat tttacttcag     360
tatgtggtga aagtttcga tagatcaacc aaagtgattg atttccatta tcctaatgag     420
cttctccaag aatataattg ggaattggca gaccaaccac aaaatttgga ggaaattttg     480
atgcattgcc aaacaactct aaaatatgca attaaaacag gcatcctag atacttcaat     540 caactttcta ctggtttgga tatggttgga ttagcagcag actggctgac atcaacagca     600
aatactaaca tgttcaccta tgaaattgct ccagtatttg tgcttttgga atatgtcaca     660
ctaaagaaaa tgagagaaat cattggctgg ccagggggct ctggcgatgg gatattttct     720
cccggtggcg ccatatctaa catgtatgcc atgatgatcg cacgctttaa gatgttccca     780
gaagtcaagg agaaaggaat ggctgctctt cccaggctca ttgccttcac gtctgaacat     840
agtcattttt ctctcaagaa gggagctgca gccttaggga ttggaacaga cagcgtgatt     900
ctgattaaat gtgatgagag agggaaaatg attccatctg atcttgaaag aaggattctt     960
gaagccaaac agaaagggtt tgttcctttc ctcgtgagtg ccacagctgg aaccaccgtg    1020
tacggagcat ttgaccccct cttagctgtc gctgacattt gcaaaaagta taagatctgg    1080
atgcatgtgg atgcagcttg gggtggggga ttactgatgt cccgaaaaca caagtggaaa    1140
ctgagtggcg tggagagggc caactctgtg acgtggaatc cacacaagat gatgggagtc    1200
cctttgcagt gctctgctct cctggttaga gaagagggat tgatgcagaa ttgcaaccaa    1260
atgcatgcct cctacctctt tcagcaagat aaacattatg acctgtccta tgacactgga    1320
gacaaggcct acagtgcgg acgccacgtt gatgttttta actatggct gatgtggagg    1380 gcaaagggga ctaccgggtt tgaagcgcat gttgataaat gtttggagtt ggcagagtat    1440
ttatacaaca tcataaaaaa ccgagaagga tatgagatgg tgtttgatgg gaagcctcag    1500
cacacaaatg tctgcttctg gtacattcct ccaagcttgc gtactctgga agacaatgaa    1560
gagagaatga gtcgcctctc gaaggtggct ccagtgatta agccagaat gatggagtat    1620 ggaaccacaa tggtcagcta ccaacccttg ggagacaagg tcaatttctt ccgcatggtc    1680
atctcaaacc cagcggcaac tcaccaagac attgacttcc tgattgaaga aatagaacgc    1740
cttggacaag atttataa                                                   1758

<210> SEQ ID NO 6
<211> LENGTH: 585
<212> TYPE: PRT
<213> ORGANISM: Homo sapiens

<400> SEQUENCE: 6
```

```
Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
            35                  40                  45

Tyr Gly Asp Ala Glu Lys Pro Ala Glu Ser Gly Gly Ser Gln Pro Pro
50                  55                  60

Arg Ala Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
            85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
            115                 120                 125

Ser Thr Lys Val Ile Asp Phe His Tyr Pro Asn Glu Leu Leu Gln Glu
            130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
            165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
            195                 200                 205

Ile Ala Pro Val Phe Val Leu Leu Glu Tyr Val Thr Leu Lys Lys Met
210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
            245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
            275                 280                 285

Ala Ala Ala Leu Gly Ile Gly Thr Asp Ser Val Ile Leu Ile Lys Cys
            290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
            325                 330                 335

Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Ala Ala Trp Gly
            355                 360                 365

Gly Gly Leu Leu Met Ser Arg Lys His Lys Trp Lys Leu Ser Gly Val
            370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
            405                 410                 415

Asn Cys Asn Gln Met His Ala Ser Tyr Leu Phe Gln Gln Asp Lys His
```

```
                420              425              430
Tyr Asp Leu Ser Tyr Asp Thr Gly Asp Lys Ala Leu Gln Cys Gly Arg
            435                  440                 445
His Val Asp Val Phe Lys Leu Trp Leu Met Trp Arg Ala Lys Gly Thr
        450                  455                 460
Thr Gly Phe Glu Ala His Val Asp Lys Cys Leu Glu Leu Ala Glu Tyr
465                  470                  475                 480
Leu Tyr Asn Ile Ile Lys Asn Arg Glu Gly Tyr Glu Met Val Phe Asp
                485                  490                 495
Gly Lys Pro Gln His Thr Asn Val Cys Phe Trp Tyr Ile Pro Pro Ser
            500                  505                 510
Leu Arg Thr Leu Glu Asp Asn Glu Glu Arg Met Ser Arg Leu Ser Lys
        515                  520                 525
Val Ala Pro Val Ile Lys Ala Arg Met Met Glu Tyr Gly Thr Thr Met
        530                  535                 540
Val Ser Tyr Gln Pro Leu Gly Asp Lys Val Asn Phe Phe Arg Met Val
545                  550                  555                 560
Ile Ser Asn Pro Ala Ala Thr His Gln Asp Ile Asp Phe Leu Ile Glu
                565                  570                 575
Glu Ile Glu Arg Leu Gly Gln Asp Leu
            580                  585

<210> SEQ ID NO 7
<211> LENGTH: 1785
<212> TYPE: DNA
<213> ORGANISM: Homo sapiens

<400> SEQUENCE: 7
atggcgtctt cgaccccatc ttcgtccgca acctcctcga acgcgggagc ggaccccaat      60
accactaacc tgcgcccccac aacgtacgat acctggtgcg cgtggcccca tggatgcacc    120
agaaaactgg ggctcaagat ctgcggcttc ttgcaaagga ccaacagcct ggaagagaag    180
agtcgccttg tgagtgcctt cagggagagg caatcctcca gaacctgctt tcctgtgaa     240 aacagcgacc gggatgcccg cttccggcgc acagagacta cttctctaa tctgttttgct   300 agagatctgc ttccggctaa gaacggtgag gagcaaaccg tgcaattcct cctggaagtg    360
gtggacatac tcctcaacta tgtccgcaag acatttgatc gctccaccaa ggtgctggac    420
tttcatcacc acaccagtt gctggaaggc atggagggct tcaacttgga gctctctgac    480 cacccccgagt ccctggagca gatcctggtt gactgcagag acaccttgaa gtatggggtt    540
cgcacaggtc atcctcgatt tttcaaccag ctctccactg gattggatat tattggccta    600
gctggagaat ggctgacatc aacgccaat accaacatgt tacatatga aattgcacca     660 gtgttttgtcc tcatggaaca aataacactt aagaagatga gagagatagt tggatggtca    720
agtaaagatg gtgatgggat attttctcct gggggcgcca tatccaacat gtacagcatc    780
atggctgctc gctacaagta cttcccggaa gttaagacaa agggcatggc ggctgtgcct    840
aaactggtcc tcttcacctc agaacagagt cactattcca taagaaaagc tggggctgca    900
cttggctttg gaactgacaa tgtgattttg ataaagtgca atgaaagggg gaaaataatt    960
ccagctgatt tgaggcaaa aattcttgaa gccaaacaga gggatatgt tccctttat     1020 gtcaatgcaa ctgctggcac gactgtttat ggagcttttg atccgataca agagattgca    1080
gatatatgtg agaaatataa cctttggttt catgtcgatg ctgcctgggg aggtgggctg    1140
ctcatgtcca ggaagcaccg ccataaactc aacggcatag aaagggccaa ctcagtcacc    1200
```

-continued

```
tggaaccctc acaagatgat gggcgtgctg ttgcagtgct ctgccattct cgtcaaggaa    1260
aagggtatac tccaaggatg caaccagatg tgtgcaggat atctcttcca gccagacaag    1320
cagtatgatg tctcctacga caccggggac aaggcaattc agtgtggccg ccacgtggat    1380
atcttcaagt tctggctgat gtggaaagca aagggcacag tgggatttga aaaccagatc    1440
aacaaatgcc tggaactggc tgaatacctc tatgccaaga ttaaaaacag agaagaattt    1500
gagatggttt tcaatggcga gcctgagcac acaaacgtct gttttggta tattccacaa    1560 agcctcaggg gtgtgccaga cagccctcaa cgacgggaaa agctacacaa ggtggctcca    1620
aaaatcaaag ccctgatgat ggagtcaggt acgaccatgg ttggctacca gccccaaggg    1680
gacaaggcca acttcttccg gatggtcatc tccaacccag ccgctaccca gtctgacatt    1740
gacttcctca ttgaggagat agaaagactg ggccaggatc tgtaa                   1785
```

<210> SEQ ID NO 8
<211> LENGTH: 592
<212> TYPE: PRT
<213> ORGANISM: Homo sapiens

<400> SEQUENCE: 8

```
Met Ala Ser Ser Thr Pro Ser Ser Ser Ala Thr Ser Ser Asn Ala Gly
1               5                   10                  15

Ala Asp Pro Asn Thr Thr Asn Leu Arg Pro Thr Thr Tyr Asp Thr Trp
            20                  25                  30

Cys Gly Val Ala His Gly Cys Thr Arg Lys Leu Gly Leu Lys Ile Cys
        35                  40                  45

Gly Phe Leu Gln Arg Thr Asn Ser Leu Glu Glu Lys Ser Arg Leu Val
    50                  55                  60

Ser Ala Phe Lys Glu Arg Gln Ser Lys Asn Leu Leu Ser Cys Glu
65                  70                  75                  80

Asn Ser Asp Arg Asp Ala Arg Phe Arg Arg Thr Glu Thr Asp Phe Ser
                85                  90                  95

Asn Leu Phe Ala Arg Asp Leu Leu Pro Ala Lys Asn Gly Glu Glu Gln
            100                 105                 110

Thr Val Gln Phe Leu Leu Glu Val Val Asp Ile Leu Leu Asn Tyr Val
        115                 120                 125

Arg Lys Thr Phe Asp Arg Ser Thr Lys Val Leu Asp Phe His His Pro
    130                 135                 140

His Gln Leu Leu Glu Gly Met Glu Gly Phe Asn Leu Glu Leu Ser Asp
145                 150                 155                 160

His Pro Glu Ser Leu Glu Gln Ile Leu Val Asp Cys Arg Asp Thr Leu
                165                 170                 175

Lys Tyr Gly Val Arg Thr Gly His Pro Arg Phe Phe Asn Gln Leu Ser
            180                 185                 190

Thr Gly Leu Asp Ile Ile Gly Leu Ala Gly Glu Trp Leu Thr Ser Thr
        195                 200                 205

Ala Asn Thr Asn Met Phe Thr Tyr Glu Ile Ala Pro Val Phe Val Leu
    210                 215                 220

Met Glu Gln Ile Thr Leu Lys Lys Met Arg Glu Ile Val Gly Trp Ser
225                 230                 235                 240

Ser Lys Asp Gly Asp Gly Ile Phe Ser Pro Gly Gly Ala Ile Ser Asn
                245                 250                 255

Met Tyr Ser Ile Met Ala Ala Arg Tyr Lys Tyr Phe Pro Glu Val Lys
            260                 265                 270

Thr Lys Gly Met Ala Ala Val Pro Lys Leu Val Leu Phe Thr Ser Glu
```

```
                 275                 280                 285
Gln Ser His Tyr Ser Ile Lys Lys Ala Gly Ala Leu Gly Phe Gly
    290                 295                 300
Thr Asp Asn Val Ile Leu Ile Lys Cys Asn Glu Arg Gly Lys Ile Ile
305                 310                 315                 320
Pro Ala Asp Phe Glu Ala Lys Ile Leu Glu Ala Lys Gln Lys Gly Tyr
                325                 330                 335
Val Pro Phe Tyr Val Asn Ala Thr Ala Gly Thr Thr Tyr Gly Ala
                340                 345                 350
Phe Asp Pro Ile Gln Glu Ile Ala Asp Ile Cys Glu Lys Tyr Asn Leu
            355                 360                 365
Trp Leu His Val Asp Ala Ala Trp Gly Gly Gly Leu Leu Met Ser Arg
    370                 375                 380
Lys His Arg His Lys Leu Asn Gly Ile Glu Arg Ala Asn Ser Val Thr
385                 390                 395                 400
Trp Asn Pro His Lys Met Met Gly Val Leu Leu Gln Cys Ser Ala Ile
                405                 410                 415
Leu Val Lys Glu Lys Gly Ile Leu Gln Gly Cys Asn Gln Met Cys Ala
                420                 425                 430
Gly Tyr Leu Phe Gln Pro Asp Lys Gln Tyr Asp Val Ser Tyr Asp Thr
            435                 440                 445
Gly Asp Lys Ala Ile Gln Cys Gly Arg His Val Asp Ile Phe Lys Phe
    450                 455                 460
Trp Leu Met Trp Lys Ala Lys Gly Thr Val Gly Phe Glu Asn Gln Ile
465                 470                 475                 480
Asn Lys Cys Leu Glu Leu Ala Glu Tyr Leu Tyr Ala Lys Ile Lys Asn
                485                 490                 495
Arg Glu Glu Phe Glu Met Val Phe Asn Gly Glu Pro Glu His Thr Asn
                500                 505                 510
Val Cys Phe Trp Tyr Ile Pro Gln Ser Leu Arg Gly Val Pro Asp Ser
            515                 520                 525
Pro Gln Arg Arg Glu Lys Leu His Lys Val Ala Pro Lys Ile Lys Ala
    530                 535                 540
Leu Met Met Glu Ser Gly Thr Thr Met Val Gly Tyr Gln Pro Gln Gly
545                 550                 555                 560
Asp Lys Ala Asn Phe Phe Arg Met Val Ile Ser Asn Pro Ala Ala Thr
                565                 570                 575
Gln Ser Asp Ile Asp Phe Leu Ile Glu Glu Ile Glu Arg Leu Gly Gln
            580                 585                 590

<210> SEQ ID NO 9
<211> LENGTH: 1774
<212> TYPE: DNA
<213> ORGANISM: Artificial
<220> FEATURE:
<223> OTHER INFORMATION: consensus nucleic acid sequence from chimeric
      nucleic acid s

<400> SEQUENCE: 9
atggcatctc cgggctctgg cttttggtct ttcgggtcgg aagatggctc tgggattccg      60
agaatcccgg cacagcgcga gcctggtgcc aagtggctca gaagttcacg ggcggcatcg     120
gaaacaaact gtgcgccctg ctctacggag acgccgagaa gccggcggag agcggcggga     180
gcgtgccttc gggggcggc gatcctggaa ggccctgctt tcctgtgaaa acagcgaccg     240
ggatgcccgc ttccggcgca cagagactga cttctctaat ctgtttgcta gagatctgct     300
```

```
tccggctaag aacggtgagg agcaaaccgt gcaattcctc ctggaagtgg tggacatact    360
cctcaactat gtccgcaaga catttgatcg ctccaccaag gtgctggact ttcatcaccc    420
acaccagttg ctggaaggca tggagggctt caacttggag ctctctgacc accccgagtc    480
cctggagcag atcctggttg actgcagaga caccttgaag tatggggttc gcacaggtca    540
tcctcgattt ttcaaccagc tctccactgg attggatatt attggcctag ctggagaatg    600
gctgacatca acggccaata ccaacatgtt tacatatgaa attgcaccag tgtttgtcct    660
catggaacaa ataacactta agaagatgag agagatagtt ggatggtcaa gtaaagatgg    720
tgatgggata ttttctcctg ggggcgccat atccaacatg tacagcatca tggctgctcg    780
ctacaagtac ttcccggaag ttaagacaaa gggcatggcg gctgtgccta aactggtcct    840
cttcacctca gaacagagtc actattccat aaagaaagct ggggctgcac ttggctttgg    900
aactgacaat gtgattttga taaagtgcaa tgaaggggg aaaataattc cagctgattt    960
tgaggcaaaa attcttgaag ccaaacagaa gggatatgtt ccctttatg tcaatgcaac    1020
tgctggcacg actgtttatg agcttttga tccgatacaa gagattgcag atatatgtga    1080
gaaatataac ctttggttgc atgtcgatgc tgcctgggga ggtgggctgc tcatgtccag    1140
gaagcaccgc cataaactca acggcataga aagggccaac tcagtcacct ggaaccctca    1200
caagatgatg ggcgtgctgt tgcagtgctc tgccattctc gtcaaggaaa agggtatact    1260
ccaaggatgc aaccagatgt gtgcaggata tctcttccag ccagacaagc agtatgatgt    1320
ctcctacgac accggggaca aggcaattca gtgtggccgc cacgtggata tcttcaagtt    1380
ctggctgatg tggaaagcaa agggcacagt gggatttgaa aaccagatca acaaatgcct    1440
ggaactggct gaatacctct atgccaagat taaaaacaga gaagaatttg agatggtttt    1500
caatggcgag cctgagcaca caaacgtctg ttttttggtat attccacaaa gcctcagggg    1560
tgtgccagac agccctcaac gacgggaaaa gctacacaag gtggctccaa aaatcaaagc    1620
cctgatgatg gagtcaggta cgaccatggt tggctaccag ccccaagggg acaaggccaa    1680
cttcttccgg atggtcatct ccaacccagc cgctacccag tctgacattg acttcctcat    1740
tgaggagata gaaagactgg gccaggatct gtaa                               1774
```

<210> SEQ ID NO 10
<211> LENGTH: 590
<212> TYPE: PRT
<213> ORGANISM: Artificial
<220> FEATURE:
<223> OTHER INFORMATION: consensus amino acid sequence from chimeric
      amino acid sequences

<400> SEQUENCE: 10

```
Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ala Glu Lys Pro Ala Glu Ser Gly Gly Ser Ala Phe Pro
    50                  55                  60

Glu Arg Gln Ala Ser Lys Asn Leu Leu Ser Cys Glu Asn Ser Asp Arg
65                  70                  75                  80

Asp Ala Arg Phe Arg Arg Thr Glu Thr Asp Phe Ser Asn Leu Phe Ala
                85                  90                  95

Arg Asp Leu Leu Pro Ala Lys Asn Gly Glu Glu Gln Thr Val Gln Phe
```

```
                100             105             110
Leu Leu Glu Val Val Asp Ile Leu Leu Asn Tyr Val Arg Lys Thr Phe
            115                 120             125

Asp Arg Ser Thr Lys Val Leu Asp Phe His His Pro His Gln Leu Leu
130                 135                 140

Glu Gly Met Glu Gly Phe Asn Leu Glu Leu Ser Asp His Pro Glu Ser
145                 150                 155                 160

Leu Glu Gln Ile Leu Val Asp Cys Arg Asp Thr Leu Lys Tyr Gly Val
                165                 170                 175

Arg Thr Gly His Pro Arg Phe Phe Asn Gln Leu Ser Thr Gly Leu Asp
                180                 185                 190

Ile Ile Gly Leu Ala Gly Glu Trp Leu Thr Ser Thr Ala Asn Thr Asn
                195                 200                 205

Met Phe Thr Tyr Glu Ile Ala Pro Val Phe Val Leu Met Glu Gln Ile
210                 215                 220

Thr Leu Lys Lys Met Arg Glu Ile Val Gly Trp Ser Ser Lys Asp Gly
225                 230                 235                 240

Asp Gly Ile Phe Ser Pro Gly Gly Ala Ile Ser Asn Met Tyr Ser Ile
                245                 250                 255

Met Ala Ala Arg Tyr Lys Tyr Phe Pro Glu Val Lys Thr Lys Gly Met
                260                 265                 270

Ala Ala Val Pro Lys Leu Val Leu Phe Thr Ser Glu Gln Ser His Tyr
                275                 280                 285

Ser Ile Lys Lys Ala Gly Ala Ala Leu Gly Phe Gly Thr Asp Asn Val
                290                 295                 300

Ile Leu Ile Lys Cys Asn Glu Arg Gly Lys Ile Ile Pro Ala Asp Phe
305                 310                 315                 320

Glu Ala Lys Ile Leu Glu Ala Lys Gln Lys Gly Tyr Val Pro Phe Tyr
                325                 330                 335

Val Asn Ala Thr Ala Gly Thr Thr Val Tyr Gly Ala Phe Asp Pro Ile
                340                 345                 350

Gln Glu Ile Ala Asp Ile Cys Glu Lys Tyr Asn Leu Trp Leu His Val
                355                 360                 365

Asp Ala Ala Trp Gly Gly Gly Leu Leu Met Ser Arg Lys His Arg His
370                 375                 380

Lys Leu Asn Gly Ile Glu Arg Ala Asn Ser Val Thr Trp Asn Pro His
385                 390                 395                 400

Lys Met Met Gly Val Leu Leu Gln Cys Ser Ala Ile Leu Val Lys Glu
                405                 410                 415

Lys Gly Ile Leu Gln Gly Cys Asn Gln Met Cys Ala Gly Tyr Leu Phe
                420                 425                 430

Gln Pro Asp Lys Gln Tyr Asp Val Ser Tyr Asp Thr Gly Asp Lys Ala
                435                 440                 445

Ile Gln Cys Gly Arg His Val Asp Ile Phe Lys Phe Trp Leu Met Trp
                450                 455                 460

Lys Ala Lys Gly Thr Val Gly Phe Glu Asn Gln Ile Asn Lys Cys Leu
465                 470                 475                 480

Glu Leu Ala Glu Tyr Leu Tyr Ala Lys Ile Lys Asn Arg Glu Glu Phe
                485                 490                 495

Glu Met Val Phe Asn Gly Glu Pro Glu His Thr Asn Val Cys Phe Trp
                500                 505                 510

Tyr Ile Pro Gln Ser Leu Arg Gly Val Pro Asp Ser Pro Gln Arg Arg
                515                 520                 525
```

```
Glu Lys Leu His Lys Val Ala Pro Lys Ile Lys Ala Leu Met Met Glu
            530                 535                 540

Ser Gly Thr Thr Met Val Gly Tyr Gln Pro Gln Gly Asp Lys Ala Asn
545                 550                 555                 560

Phe Phe Arg Met Val Ile Ser Asn Pro Ala Ala Thr Gln Ser Asp Ile
                565                 570                 575

Asp Phe Leu Ile Glu Glu Ile Glu Arg Leu Gly Gln Asp Leu
            580                 585                 590

<210> SEQ ID NO 11
<211> LENGTH: 27
<212> TYPE: DNA
<213> ORGANISM: Artificial
<220> FEATURE:
<223> OTHER INFORMATION: GAD67 forward primer sequence

<400> SEQUENCE: 11
aataatctcg agtgccttca gggagag                                    27

<210> SEQ ID NO 12
<211> LENGTH: 27
<212> TYPE: DNA
<213> ORGANISM: Artificial
<220> FEATURE:
<223> OTHER INFORMATION: GAD67 reverse primer sequence

<400> SEQUENCE: 12
atatattctg cagtcaacca ggatctg                                    27

<210> SEQ ID NO 13
<211> LENGTH: 31
<212> TYPE: DNA
<213> ORGANISM: Artificial
<220> FEATURE:
<223> OTHER INFORMATION: GAD65 shorter construct forward primer sequence

<400> SEQUENCE: 13
aataattctg agatggcatc tccggcctct g                               31

<210> SEQ ID NO 14
<211> LENGTH: 25
<212> TYPE: DNA
<213> ORGANISM: Artificial
<220> FEATURE:
<223> OTHER INFORMATION: GAD65 shorter construct reverse primer sequence

<400> SEQUENCE: 14
atatatactc gagccgctct ccgcc                                      25

<210> SEQ ID NO 15
<211> LENGTH: 32
<212> TYPE: DNA
<213> ORGANISM: Artificial
<220> FEATURE:
<223> OTHER INFORMATION: GAD67 deletion forward primer sequence

<400> SEQUENCE: 15
aataatctcg agtgtgaaaa cagcgaccgg ga                              32

<210> SEQ ID NO 16
<211> LENGTH: 27
<212> TYPE: DNA
<213> ORGANISM: Artificial
<220> FEATURE:
<223> OTHER INFORMATION: GAD67 deletion reverse primer sequence
```

```
<400> SEQUENCE: 16
atatattctg cagtcaacca ggatctg                                          27

<210> SEQ ID NO 17
<211> LENGTH: 31
<212> TYPE: DNA
<213> ORGANISM: Artificial
<220> FEATURE:
<223> OTHER INFORMATION: GAD65 longer construct forward primer sequence

<400> SEQUENCE: 17
aataatctcg agatggcatc tccggcctct g                                     31

<210> SEQ ID NO 18
<211> LENGTH: 28
<212> TYPE: DNA
<213> ORGANISM: Artificial
<220> FEATURE:
<223> OTHER INFORMATION: GAD65 longer construct reverse primer sequence

<400> SEQUENCE: 18
atatatctcg agggcggcct tccgggcg                                         28
```